US008609661B2

(12) United States Patent
Verkman et al.

(10) Patent No.: US 8,609,661 B2
(45) Date of Patent: Dec. 17, 2013

(54) PYRIMIDO-PYRROLO-QUINOXALINEDIONE INHIBITORS OF CYSTIC FIBROSIS TRANSMEMBRANE CONDUCTANCE REGULATOR PROTEIN AND USES THEREFOR

(75) Inventors: Alan S. Verkman, San Francisco, CA (US); Lukmanee Tradtrantip, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 13/389,898

(22) PCT Filed: Aug. 10, 2010

(86) PCT No.: PCT/US2010/045052
§ 371 (c)(1),
(2), (4) Date: Apr. 30, 2012

(87) PCT Pub. No.: WO2011/019737
PCT Pub. Date: Feb. 17, 2011

(65) Prior Publication Data
US 2012/0208822 A1    Aug. 16, 2012

Related U.S. Application Data

(60) Provisional application No. 61/232,741, filed on Aug. 10, 2009.

(51) Int. Cl.
A61K 31/519     (2006.01)
A61P 1/00       (2006.01)
A61P 1/12       (2006.01)
A61P 13/12      (2006.01)

(52) U.S. Cl.
USPC ........................................................ 514/250

(58) Field of Classification Search
None
See application file for complete search history.

(56) References Cited

U.S. PATENT DOCUMENTS

| | | | |
|---|---|---|---|
| 7,235,573 B2 | 6/2007 | Verkman et al. | |
| 7,414,037 B2 | 8/2008 | Verkman et al. | |
| 2006/0160815 A1* | 7/2006 | Sabatucci et al. | 514/250 |
| 2008/0064666 A1 | 3/2008 | Verkman et al. | |
| 2008/0269206 A1* | 10/2008 | Russell et al. | 514/226.2 |
| 2009/0253799 A1 | 10/2009 | Verkman et al. | |

FOREIGN PATENT DOCUMENTS

| | | |
|---|---|---|
| WO | 98/05642 A1 | 2/1998 |
| WO | 98/28301 A1 | 7/1998 |
| WO | 2004/111014 A1 | 12/2004 |
| WO | 2005/039589 A2 | 5/2005 |
| WO | 2009/076593 A1 | 6/2009 |
| WO | 2009/120803 A2 | 10/2009 |
| WO | 2012/166658 A1 | 12/2012 |

OTHER PUBLICATIONS

Tsupak et al. [3,4]-Annulated pyrroles 1. Poluynuclear heterocyclic systems based on pyrrolo [3,4-d]pyrimidine-2,4-dione. Russian Chemical Bullentin, International Edition, (2006), vol. 55, pp. 2265-2270.*
Azas et al., "Antiparasitic activity of highly conjugated pyrimidine-2,4-dione derivatives," *Il Farmaco* 58:1263-1270, 2003.
Brill et al , "Immunolocalization of ion transport proteins in human autosomal dominant polycystic kidney epithelial cells," *Proc. Natl. Acad. Sci. USA* 93:10206-10211, Sep. 1996.
Caci et al., "Evidence for direct CFTR inhibition by $CFTR_{inh}$-172 based on $Arg^{347}$ mutagenesis," *Biochem. J.* 413:135-142, 2008.
Clarke et al., "Defective Epithelial Chloride Transport in a Gene-Targeted Mouse Model of Cystic Fibrosis," *Science* 257:1125-1128, Aug. 21, 1992.
Cotton et al., "PKD and CF: An Interesting Family Provides Insight Into the Molecular Pathophysiology of Polycystic Kidney Disease," *Am. J. Kidney Dis.* 32(6):1081-1083, 1998.
Davidow et al., "The cystic fibrosis transmembrane conductance regulator mediates transepithelial fluid secretion by human autosomal dominant polycystic kidney disease epithelium in vivo," *Kidney International* 50:208-218, 1996.
Dawson et al., "CFTR: Mechanism of Anion Conduction," *Physiological Reviews* 79(Suppl., No. 1):S47-S75, Jan. 1999.
Edwards et al., "Induction of a glibenclamide-sensitive K-current by modification of a delayed rectifier channel in rat portal vein and insulinoma cells," *Br. J. Pharmacol.* 110:1280-1281, 1993.
Field, "Intestinal ion transport and the pathophysiology of diarrhea," *J. Clin. Invest.* 111(7):931-943, 2003.
Gabriel et al., "Cystic Fibrosis Heterozygote Resistance to Cholera Toxin in the Cystic Fibrosis Mouse Model," *Science* 266:107-109, Oct. 7, 1994.
Gadsby et al., "The ABC protein turned chloride channel whose failure causes cystic fibrosis," *Nature* 440(7083):477-483, Mar. 23, 2006.
Hanaoka et al., "cAMP Regulates Cell Proliferation and Cyst Formation in Autosomal Polycystic Kidney Disease Cells," *J. Am. Soc. Nephrol* 11:1179-1187, 2000.
Kunzelmann et al., "Electrolyte Transport in the Mammalian Colon: Mechanisms and Implications for Disease," *Physiol. Rev.* 82:245-289, 2002.
Li et al., "The relationship between cell proliferation, $Cl^-$ secretion, and renal cyst growth: A study using CFTR inhibitors," *Kidney International* 66:1926-1938, 2004.
Lohi et al., "Upregulation of CFTR expression but not SLC26A3 and SLC9A3 in ulcerative colitis," *Am. J. Physiol. Gastrointest. Liver Physiol.* 283:G567-G575, 2002.
Ma et al., "Thiazolidinone CFTR inhibitor identified by high-throughput screening blocks cholera toxin-induced intestinal fluid secretion," *J. Clin. Invest.* 110(11):1651-1658, 2002.
McCarty, "Permeation through the CFTR chloride channel," *The Journal of Experimental Biology* 203:1947-1962, 2000.
Muanprasat et al., "Discovery of Glycine Hydrazide Pore-occluding CFTR Inhibitors: Mechanism, Structure-Activity Analysis, and in Vivo Efficacy," *J. Gen. Physiol.* 124:125-137, Aug. 2004.
Nagata et al., "Tricyclic Quinoxalinediones: 5,6-Dihydro-1*H*-pyrrolo[1,2,3-*de*]quinoxaline-2,3-diones and 6,7-Dihydro-1*H*,5*H*-pyrido[1,2,3-*de*]quinoxaline-2,3-diones as Potent Antagonists for the Glycine Binding Site of the NMDA Receptor," *J. Med. Chem.* 37:3956-3968, 1994.
Namkung et al., "In Situ Measurement of Airway Surface Liquid [$K^+$] Using a Ratioable $K^+$-sensitive Fluorescent Dye," *The Journal of Biological Chemistry* 284(23):15916-15926, Jun. 5, 2009.

O'Sullivan et al., "Cystic Fibrosis and the Phenotypic Expression of Autosomal Dominant Polycystic Kidney Disease," *American Journal of Kidney Diseases* 32(6):976-983, 1998.

Oels et al., "Reinvestigation of the Synthesis of 3-Dimethylallyl-4-hydroxy-2-quinol-ones. A Novel Route to Tetracyclic Heteroaromatic Compounds," *J. Chem. Soc. Perkin Trans.* 23:2546-2551, 1977.

Routaboul et al., "Discovery of α-Aminoazaheterocycle-Methylglyoxal Adducts as a New Class of High-Affinity Inhibitors of Cystic Fibrosis Transmembrane Conductance Regulator Chloride Channels," *The Journal of Pharmacology and Experimental Therapeutics* 322(3):1023-1035, 2007.

Schultz et al., "Pharmacology of CFTR Chloride Channel Activity," *Physiological Reviews* 79(Suppl., No. 1):S109-S144, Jan. 1999.

Sheppard et al., "Mechanism of glibenclamide inhibition of cystic fibrosis transmembrane conductance regulator Cl− channels expressed in a murine cell line," *Journal of Physiology* 503.2:333-346, 1997.

Sheppard et al., "Structure and Function of the CFTR Chloride Channel," *Physiological Reviews* 79(Suppl. No. 1):S23-S45, Jan. 1999.

Sonawane et al., "α-Aminoazaheterocyclic-Methylglyoxal Adducts Do Not Inhibit Cystic Fibrosis Transmembrane Conductance Regulator Chloride Channel Activity," *The Journal of Pharmacology and Experimental Therapeutics* 325(2):529-535, 2008.

Sonawane et al., "In Vivo Pharmacology and Antidiarrheal Efficacy of a Thiazolidinone CFTR Inhibitor in Rodents," *Journal of Pharmaceutical Sciences* 94(1):134-143, 2005.

Sonawane et al., "Lectin Conjugates as Potent, Nonabsorbable CFTR Inhibitors for Reducing Intestinal Fluid Secretion in Cholera," *Gastroenterology* 132:1234-1244, 2007.

Sonawane et al., "Luminally active, nonabsorbable CFTR inhibitors as potential therapy to reduce intestinal fluid loss in cholera," *The FASEB Journal* 20:130-132, Jan. 2006.

Sonawane et al., "Thiazolidinone CFTR inhibitors with improved water solubility identified by structure-activity analysis," *Bioorganic & Medicinal Chemistry* 16:8187-8195, 2008.

Taddei et al., "Altered channel gating mechanism for CFTR inhibition by a high-affinity thiazolidinone blocker," *FEBS Letters* 558:52-56, 2004.

Thiagarajah et al., "Prevention of Toxin-Induced Intestinal Ion and Fluid Secretion by a Small-Molecule CFTR Inhibitor," *Gastroenterology* 126:511-519, 2004.

Torres et al., "Mechanisms of Disease: autosomal dominant and recessive polycystic kidney diseases," *Nature Clinical Practice—Nephrology* 2(1):40-55, Jan. 2006.

Tsupak et al., "Pyrollopyrimidines. 5. Interaction of 6-amino-1,3-dimethylpyrrolo[3,4-d]-pyrimidin-2,4(1H,3H)-diones with 1,3-diketones," *Khim. Geterotsikl. Soedin.*7:1096-1102, 2003.

Tsupak et al., "[3,4]-Annulated pyrroles 1. Polynuclear heterocyclic systems based on pyrrolo[3,4-d]pyrimidine-2,4-dione," *Russ. Chem. Bull.* 55(12):2265-2270, 2006.

Verkman et al., "Chloride channels as drug targets," *Nat. Rev. Drug Discov.* 8(2):153-171, Feb. 2009.

Xu et al., "Autosomal dominant polycystic kidney disease coexisting with cystic fibrosis," *J. Nephrol.* 19:529-534, 2006.

Zhou et al., "Probing an Open CFTR Pore with Organic Anion Blockers," *J. Gen. Physiol.* 120:647-662, Nov. 2002.

\* cited by examiner

*Primary Examiner* — Bong-Sook Baek
*Assistant Examiner* — Taina D Matos Negron
(74) *Attorney, Agent, or Firm* — Seed IP Law Group PLLC

(57) ABSTRACT

Provided herein are pyrimido-pyrrolo-quinoxalinedione (PPQ) compounds, and compositions comprising these compounds, that inhibit cystic fibrosis transmembrane conductance regulator (CFTR) mediated ion transport and that are useful for treating diseases and disorders associated with aberrantly increased CFTR chloride channel activity. The compounds, and compositions comprising the compounds, described herein are useful for treating diseases, disorders, and sequelae of diseases, disorders, and conditions that are associated with aberrantly increased CFTR activity, for example, polycystic kidney disease. The compounds may be used for inhibiting expansion or preventing formation of cysts in persons who have polycystic kidney disease.

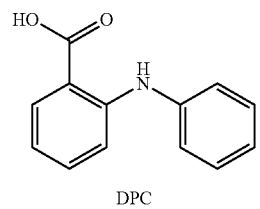

DPC

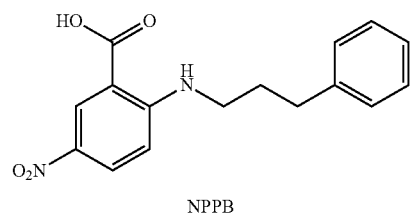

NPPB

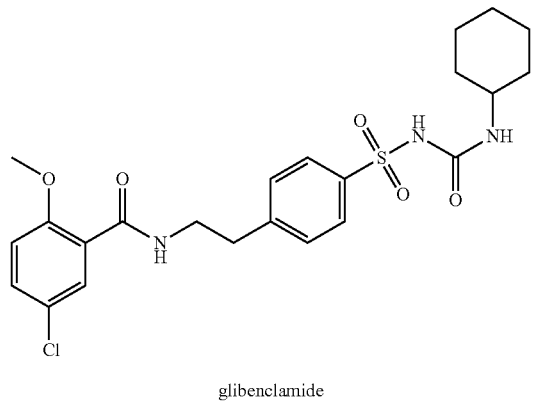

glibenclamide

CFTR$_{inh}$-172

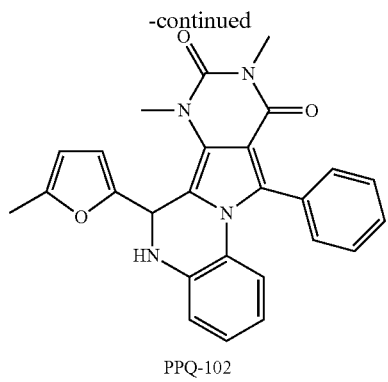
PPQ-102
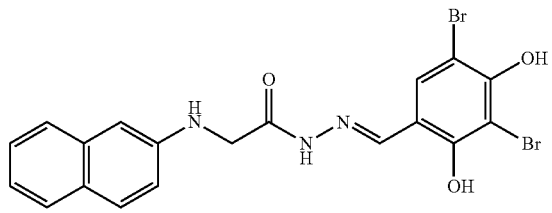
GlyH-101
15 Claims, 10 Drawing Sheets

PYRIMIDO-PYRROLO-QUINOXALINEDIONE INHIBITORS OF CYSTIC FIBROSIS TRANSMEMBRANE CONDUCTANCE REGULATOR PROTEIN AND USES THEREFOR

CROSS-REFERENCE TO RELATED APPLICATION

This application is a U.S. national stage application filed under 35 U.S.C. §371 of International Patent Application PCT/US2010/045052, accorded an international filing date of Aug. 10, 2010, which claims the benefit of U.S. Provisional Application No. 61/232,741 filed Aug. 10, 2009, all of which applications are incorporated herein by reference in their entirety.

STATEMENT OF GOVERNMENT INTEREST

This invention was made with government support under Grant Nos. P30 DK72517, R01 HL73856, R37 DK35124, and DK086125 awarded by the National Institutes of Health. The government has certain rights in the invention.

BACKGROUND

1. Field

Therapeutics are needed for treating diseases and disorders related to aberrant cystic fibrosis transmembrane conductance regulator protein (CFTR)-mediated ion transport, such as polycystic kidney disease, increased intestinal fluid secretion, and secretory diarrhea. Small molecule compounds are described herein that are potent inhibitors of CFTR activity and that may be used for treating such diseases and disorders.

2. Description of the Related Art

The cystic fibrosis transmembrane conductance regulator protein (CFTR) is a cAMP-activated chloride ($Cl^-$) channel expressed in epithelial cells in mammalian airways, intestine, pancreas, and testis (see, e.g., Sheppard et al., *Physiol. Rev.* 79:S23-45 (1999); Gadsby et al., *Nature* 40:477-83 (2006)). Hormones, such as a β-adrenergic agonist, or a toxin, such as cholera toxin, lead to an increase in cAMP, activation of cAMP-dependent protein kinase, and phosphorylation of the CFTR $Cl^-$ channel, which causes the channel to open. An increase in cell $Ca^{2+}$ can also activate different apical membrane channels. Phosphorylation by protein kinase C can either open or shut $Cl^-$ channels in the apical membrane. CFTR is predominantly located in epithelia where it provides a pathway for the movement of $Cl^-$ ions across the apical membrane and a key point at which to regulate the rate of transepithelial salt and water transport.

CFTR chloride channel function is associated with a wide spectrum of disease, including cystic fibrosis (CF) and with some forms of male infertility, polycystic kidney disease, and secretory diarrhea. Cystic fibrosis is a hereditary lethal disease caused by mutations in CFTR (see, e.g., Quinton, *Physiol. Rev.* 79:S3-S22 (1999); Boucher, *Eur. Respir. J.* 23:146-58 (2004)). Observations in human patients with CF and mouse models of CF indicate the functional importance of CFTR in intestinal and pancreatic fluid transport, as well as in male fertility (Grubb et al., *Physiol. Rev.* 79:S193-S214 (1999); Wong, P. Y., *Mol. Hum. Reprod.* 4:107-110 (1997)). CFTR is also expressed in enterocytes in the intestine and in cyst epithelium in polycystic kidney disease (see, e.g., O'Sullivan et al., *Am. J. Kidney Dis.* 32:976-983 (1998); Sullivan et al., *Physiol. Rev.* 78:1165-91 (1998); Strong et al., *J. Clin. Invest.* 93:347-54 (1994); Mall et al., *Gastroenterology* 126:32-41 (2004); Hanaoka et al., *Am. J. Physiol.* 270: C389-C399 (1996); Kunzelmann et al., *Physiol. Rev.* 82:245-289 (2002); Davidow et al., *Kidney Int.* 50:208-18 (1996); Li et al., *Kidney Int.* 66:1926-38 (2004); Al-Awqati, *J. Clin. Invest.* 110:1599-1601 (2002); Thiagarajah et al., *Curr. Opin. Pharmacol.* 3:594-99 (2003)).

Polycystic kidney disease (PKD) is characterized by massive enlargement of fluid-filled cysts of renal tubular origin that compromise normal renal parenchyma and cause renal failure (Arnaout, *Annu Rev Med* 52: 93-123, 2001; Gabow *N Engl J Med* 329: 332-342, 1993; Harris et al., *Mol Genet Metab* 81: 75-85, 2004; Wilson *N Engl J Med* 350: 151-164, 2004; Sweeney et al., *Cell Tissue Res* 326: 671-685, 2006; Chapman *J Am Soc Nephrol* 18: 1399-1407, 2007). Human autosomal dominant PKD (ADPKD) is caused by mutations in one of two genes, PKD1 and PKD2, encoding the interacting proteins polycystin-1 and polycystin-2, respectively (Wilson, supra; Qian et al., *Cell* 87: 979-987, 1996; Wu et al., *Cell* 93: 177-188, 1998; Watnick et al., Torres et al., *Nat Med* 10: 363-364, 2004 *Nat Genet* 25: 143-144, 2000). Cyst growth in PKD involves fluid secretion into the cyst lumen coupled with epithelial cell hyperplasia.

Several CFTR inhibitors have been discovered, although many exhibit weak potency and lack CFTR specificity. The oral hypoglycemic agent glibenclamide inhibits CFTR $Cl^-$ conductance from the intracellular side by an open channel blocking mechanism (Sheppard et al., *J. Physiol.*, 503:333-346 (1997); Zhou et al., *J. Gen. Physiol.* 120:647-62 (2002)) at high micromolar concentrations where it affects other $Cl^-$ and cation channels (Edwards & Weston, 1993; Rabe et al., *Br. J. Pharmacol.* 110:1280-81 (1995); Schultz et al., *Physiol. Rev.* 79:S109-S144 (1999)). Other non-selective anion transport inhibitors, including diphenylamine-2-carboxylate (DPC), 5-nitro-2(3-phenylpropyl-amino)benzoate (NPPB), and flufenamic acid, also inhibit CFTR by occluding the pore at an intracellular site (Dawson et al., *Physiol. Rev.,* 79:S47-S75 (1999); McCarty, *J. Exp. Biol.,* 203:1947-62 (2000)).

High-affinity CFTR inhibitors also have clinical application in the therapy of secretory diarrheas. Cell culture and animal models indicated that intestinal chloride secretion in enterotoxin-mediated secretory diarrheas occurs mainly through CFTR (see, e.g., Clarke et al., *Science* 257:1125-28 (1992); Gabriel et al., *Science* 266:107-109 (1994); Kunzelmann and Mall, *Physiol. Rev.* 82:245-89 (2002); Field, M. *J. Clin. Invest.* 111:931-43 (2003); and Thiagarajah et al., *Gastroenterology* 126:511-519 (2003)).

Diarrheal disease in children is a global health concern: Approximately four billion cases among children occur annually, resulting in at least two million deaths. Travelers' diarrhea affects approximately 6 million people per year. Antibiotics are routinely used to treat diarrhea; however, the antibiotics are ineffective for treating many pathogens, and the use of these drugs contributes to development of antibiotic resistance in other pathogens. Oral replacement of fluid loss is also routinely used to treat diarrhea, but is primarily palliative. Therapy directed at reducing intestinal fluid secretion (anti-secretory therapy') has the potential to overcome limitations of existing therapies.

A need exists for CFTR inhibitors, particularly those that are safe, non-absorbable, highly potent, inexpensive, and chemically stable.

BRIEF SUMMARY

Briefly, provided herein are pyrimido-pyrrolo-quinoxalinedione (PPQ) compounds, and compositions comprising such compounds, that inhibit cystic fibrosis transmembrane conductance regulator (CFTR) mediated ion transport and that are useful for treating diseases and disorders associated with aberrantly increased CFTR chloride channel activity.

The PPQ compounds, which are highly potent CFTR inhibitors, and compositions comprising these compounds, described herein, are useful for treating diseases and disorders treatable by inhibiting CFTR-mediated ion transport. Methods are provided for inhibiting enlargement of kidney cysts or preventing or inhibiting the formation of cysts and thereby treating polycystic kidney disease. Methods of treating diseases and disorders associated with aberrantly increased intestinal fluid secretion, such as secretory diarrhea and Traveler's diarrhea, are also provided.

Thus, provided herein is a pharmaceutical composition comprising a physiologically acceptable excipient and a compound having the following structure (I):

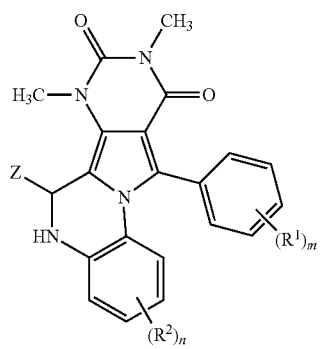

(I)

as an isolated enantiomer or a racemic mixture of enantiomers, or as a pharmaceutically acceptable salt, hydrate, solvate, N-oxide or prodrug thereof, wherein:
m is 1, 2, 3, 4 or 5;
n is 1, 2, 3 or 4;
each $R^1$ is the same or different and independently hydrogen, alkyl, halo, or alkoxy;
each $R^2$ is the same or different and independently hydrogen, alkyl, halo or alkoxy; and
Z is aryl or heteroaryl,
wherein the compound is capable of inhibiting cystic fibrosis transmembrane conductance regulator (CFTR)-mediated ion transport.

Further provided herein is a pharmaceutical composition comprising a physiologically acceptable excipient and a compound having the following substructure (IA):

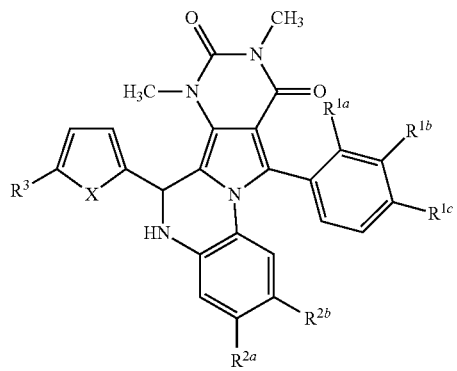

(IA)

as an isolated enantiomer or a racemic mixture of enantiomers, or as a pharmaceutically acceptable salt, hydrate, solvate, N-oxide or prodrug thereof, wherein:

$R^{1a}$, $R^{1b}$, and $R^{1c}$ are each the same or different and independently hydrogen, alkyl, halo, or alkoxy;
$R^{2a}$ and $R^{2b}$ are each the same or different and independently hydrogen, alkyl, halo, or alkoxy;
$R^3$ is hydrogen or alkyl, and
X is —O—, or —S—,
wherein the compound is capable of inhibiting cystic fibrosis transmembrane conductance regulator (CFTR)-mediated ion transport.

Also provided herein is a pharmaceutical composition comprising a physiologically acceptable excipient and a compound having the following substructure (IB):

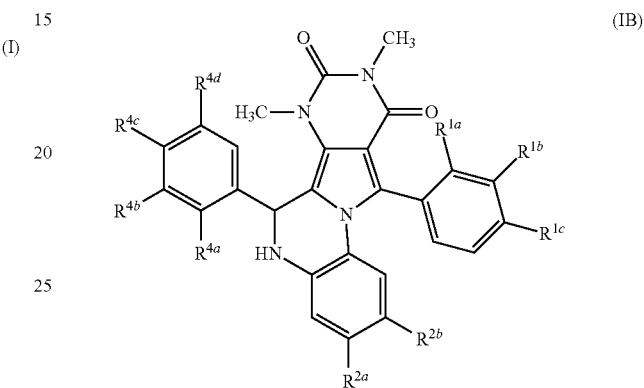

(IB)

as an isolated enantiomer or a racemic mixture of enantiomers, or as a pharmaceutically acceptable salt, hydrate, solvate, N-oxide or prodrug thereof, wherein:
$R^{1a}$, $R^{1b}$, and $R^{1c}$ are each the same or different and independently hydrogen, alkyl, halo, or alkoxy;
$R^{2a}$ and $R^{2b}$ are each the same or different and independently hydrogen, alkyl, halo, or alkoxy; and
$R^{4a}$, $R^{4b}$, $R^{4c}$, and $R^{4d}$ are each the same or different and independently hydrogen, alkyl, alkenyl, halo, alkoxy, nitro, or hydroxy,
wherein the compound is capable of inhibiting cystic fibrosis transmembrane conductance regulator (CFTR)-mediated ion transport.

Further provided herein is a method for inhibiting cystic fibrosis transmembrane conductance regulator (CFTR)-mediated ion transport, said method comprising contacting (a) a cell that comprises CFTR and (b) the composition comprising a physiologically acceptable excipient and a compound of any one of structure (I), substructures (IA) and (IB), and specific structures described above and herein, under conditions and for a time sufficient that permit the CFTR and the compound to interact, thereby inhibiting CFTR-mediated ion transport.

Further provided herein is a method for inhibiting cyst formation or inhibiting cyst enlargement, said method comprising contacting (a) a cell that comprises CFTR and (b) the composition comprising a physiologically acceptable excipient and a compound of any one of structure (I), substructures (IA) and (IB), and specific structures described above and herein, under conditions and for a time sufficient that permit CFTR and the compound to interact, wherein the compound inhibits CFTR-mediated ion transport.

Further provided herein is a method for treating polycystic kidney disease comprising administering to a subject a pharmaceutical composition comprising a physiologically acceptable excipient and a compound of any one of structure (I), substructures (IA) and (IB), and specific structures described above and herein. In such method, the polycystic kidney disease is autosomal dominant polycystic kidney disease or is autosomal recessive polycystic kidney disease.

Further provided herein is a method for treating a disease, condition, or disorder that is treatable by inhibiting cystic fibrosis transmembrane conductance regulator (CFTR)-mediated ion transport, said method comprising administering to a subject the pharmaceutical compositions described herein comprising a pharmaceutically acceptable excipient and a compound of any of structure (I), substructures (IA) and (IB) and specific structures described above and herein, thereby inhibiting CFTR-mediated ion transport. In such a method, the disease, condition, or disorder can be selected from polycystic kidney disease, aberrantly increased intestinal fluid secretion, and secretory diarrhea. More specifically, the secretory diarrhea is (a) caused by an enteric pathogen; (b) induced by an enterotoxin; or (c) a sequelae of ulcerative colitis, irritable bowel syndrome (IBS), AIDS, chemotherapy, or an enteropathogenic infection.

Further provided herein is use of the pharmaceutical composition comprising a physiologically acceptable excipient and a compound of any one of structure (I), substructures (IA) and (IB), and specific structures described above and herein, for treating a disease, condition, or disorder that is selected from polycystic kidney disease, aberrantly increased intestinal fluid secretion, and secretory diarrhea. Also provided herein is a use of a pharmaceutical composition comprising a physiologically acceptable excipient and a compound of any one of structure (I), substructures (IA) and (IB), and specific structures described above and herein, for the manufacture of a medicament for treating a disease, condition, or disorder that is selected from polycystic kidney disease, aberrantly increased intestinal fluid secretion, and secretory diarrhea. In still another embodiment, a pharmaceutical composition comprising a physiologically acceptable excipient and a compound of any one of structure (I), substructures (IA) and (IB), and specific structures described above and herein, is provided for use in treating a disease, condition, or disorder that is selected from polycystic kidney disease, aberrantly increased intestinal fluid secretion, and secretory diarrhea.

As used herein and in the appended claims, the singular forms "a," "and," and "the" include plural referents unless the context clearly dictates otherwise. Thus, for example, reference to "an agent" includes a plurality of such agents, and reference to "a cell" or "the cell" includes reference to one or more cells and equivalents thereof (e.g., plurality of cells) known to those skilled in the art, and so forth. Similarly, reference to "a compound" or "a composition" includes a plurality of such compounds or compositions, and refers to one or more compounds or compositions, respectively, unless the context clearly dictates otherwise. The term "about" when referring to a number or a numerical range means that the number or numerical range referred to is an approximation within experimental variability (or within statistical experimental error), and thus the number or numerical range may vary between 1% and 15% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, may "consist of" or "consist essentially of" the described features.

BRIEF DESCRIPTION OF THE DRAWINGS

FIG. 1A presents the chemical structures of CFTR inhibitors: diphenylamine-2-carboxylate (DPC); 5-nitro-2-(3-phenylpropyl-amino)benzoate (NPPB); glibenclamide; thiazolidinone compound designated $CFTR_{inh}$-172; glycine hydrazide compound designated GlyH-101, and PPQ compound designated PPQ-102 described in greater detail herein. FIG. 1B presents representative data from screening assays. Cell-based screening was performed in 96-well plates containing FRT cells that expressed human CFTR and the YFP (yellow fluorescence protein) halide sensor YFP-H148Q/I152L. CFTR was maximally stimulated by an agonist mixture and CFTR-mediated iodide influx was measured as YFP fluorescence quenching. Fluorescence data are shown from individual wells in the absence of agonists (no activators), and in the presence of agonists for the negative control (DMSO vehicle alone), positive control (10 µM $CFTR_{inh}$-172), and test compounds (at 25 µM) (data for exemplary inactive compounds and active compounds are shown).

FIG. 2A: Summary of structure-activity analysis, listing structural determinants shared by PPQ inhibitors of CFTR chloride conductance. FIG. 2B: Synthesis of PPQ-102 (compound 7) and PPQ-102B (compound 8). Reagents and conditions: (a) $Me_2SO_4$, NaOH, 40° C., 4 h, 43%; (b) PhCOCl, $ZnCl_2$, toluene, reflux, 6 h, 28%; (c) $Br_2$, $CHCl_3$, rt, 2 h, 57%; (d) N-(2-aminophenyl)acetamide, microwave, 170° C., 1 h, 51%; (e) HCl, reflux, 6 h, 67%; (f) 5-Me-furan-2-carbaldehyde, 170° C., 10 min, 43%; (g) $KMnO_4$, $Me_2CO$, 1 h, 40%.

FIG. 3A: Apical membrane current measured in CFTR-expressing FRT cells in the presence of a transepithelial chloride gradient and with amphotericin B permeabilization of the basolateral membrane. CFTR was activated by CPT-cAMP (chlorophenylthio-cAMP) (100 µM), with increasing concentrations of PPQ-102 added as shown. Left: Original recording. Right: Dose-response (S.E. n=4). FIG. 3B: Measurements as in FIG. 3A, but with apigenin (100 µM) or IBMX (100 µM) as agonists. The data are representative of 3 sets of experiments. FIG. 3C: Short-circuit current measured in T84 (left) and human bronchial airway epithelial cells (right). CFTR was maximally activated by 10 µM forskolin and 100 µM IBMX ('forsk'). Current in the absence of inhibitor is indicated as 'control. ' FIG. 3D: Calcium-activated chloride channels were activated by UTP (100 µM) in cystic fibrosis (CFTR-deficient) human bronchial epithelial cells, with PPQ-102 added as indicated. ENaC (epithelial sodium channel) was inhibited by amiloride (10 µM). FIG. 3E: Cellular cAMP assayed in CHO—K1 cells under basal conditions and after addition of 20 µM forskolin (S.E. n=4, differences with PPQ-102, not significant).

FIG. 4A (left): Whole-cell currents measured in CFTR-expressing FRT cells recorded at a holding potential at 0 mV, and pulsing to voltages between ±100 mV in steps of 20 mV in the absence and presence of 500 nM PPQ-102. CFTR was stimulated by 10 µM forskolin. FIG. 4A (right): Current/voltage (I/V) plot of mean currents. The data are representative of 4 sets of measurements. FIG. 4B (left): Single channel recordings in the cell-attached configuration. CFTR was activated by 10 µM forskolin and 100 µM IBMX. Pipette potential was +80 mV. FIG. 4B (right): Effect of 1 µM PPQ-102 on CFTR channel open probability ($P_o$), mean channel open time and mean channel closed time (S.E., n=3-4, *P<0.01). O, open; C, closed.

FIG. 5A: Inhibition of cyst formation. FIG. 5A (left): Transmission light micrographs of kidneys in culture. As indicated, the culture medium contained 0 or 100 μM 8-Br-cAMP and/or 0, 0.5, or 5 μM PPQ-102. FIG. 5A (right): Summary of cyst volumes after 4 days in culture shown as the fractional kidney area occupied by cysts (S.E., 6-8 kidneys, *P<0.001 compared to +8-Br-cAMP, 0 μM PPQ-102). FIG. 5B: Hematoxylin and eosin-staining of kidney paraffin sections after 4 days in culture in the presence of 0 or 100 μM 8-Br-cAMP and the indicated concentrations of PPQ-102. Representative of studies on 3 kidneys for each condition. FIG. 5C: Reversal of pre-formed renal cysts. FIG. 5C (left): Transmission light micrographs of kidneys cultured in 8-Br-cAMP for 3 days, with 5 μM PPQ-102 added at day 3 (two kidneys shown per condition). Micrographs at the right show kidneys at day 5 that were not exposed to PPQ-102. FIG. 5C (right): Summary of cyst volumes at day 5 (S.E., 6 kidneys, *P<0.001).

DETAILED DESCRIPTION

Figure 1A:
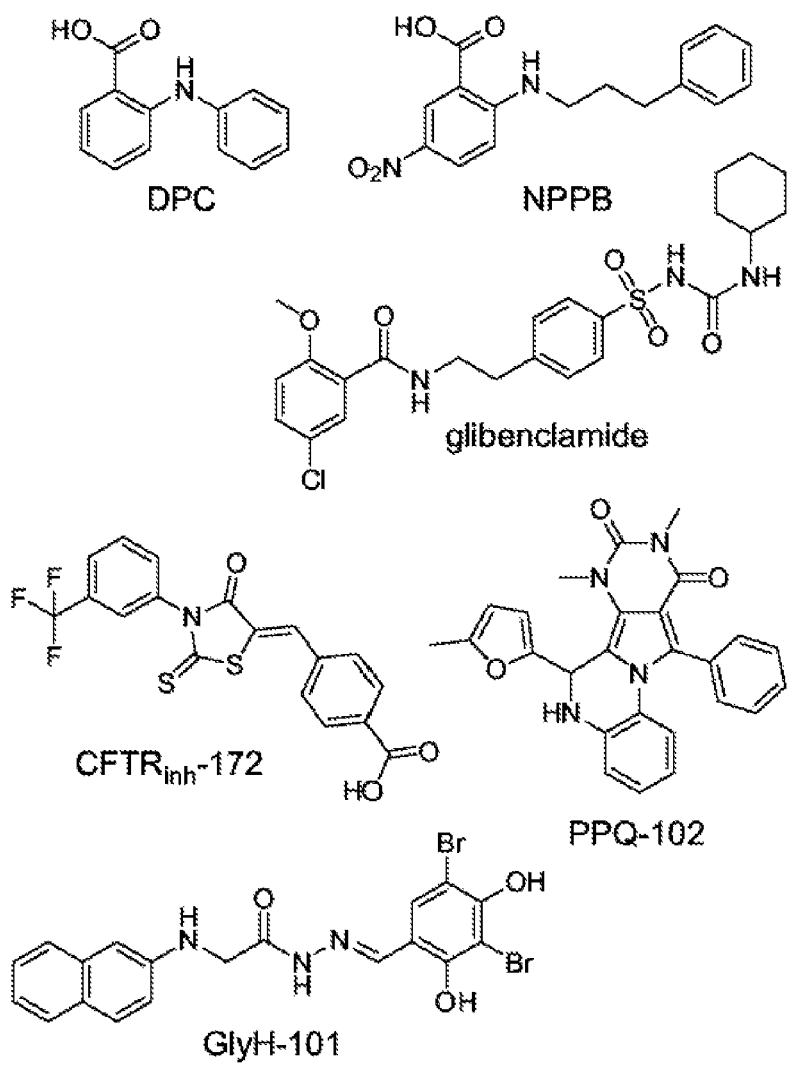
FIGS. 1A and 1B.

Provided herein are pyrimido-pyrrolo-quinoxalinedione (PPQ) compounds that inhibit activity of the cystic fibrosis transmembrane conductance regulator (CFTR) chloride channel. The PPQ compounds described herein are capable of inhibiting CFTR-mediated ion transport (e.g., CFTR-mediated Cl⁻ transport) (i.e., inhibiting CFTR conductance). The compounds and compositions comprising the PPQ compounds are therefore useful for administering to a subject who has or who is at risk of developing a disease, disorder, or condition that is treatable (i.e., administration of the compounds and compositions will provide a therapeutic or prophylactic benefit) by inhibiting CFTR-mediated ion transport.

The PPQ compounds described herein are highly potent CFTR inhibitors that are uncharged and thereby membrane-potential insensitive. CFTR inhibitors are predicted to slow renal cyst expansion in polycystic kidney disease (PKD), where fluid accumulation in renal cysts is CFTR-dependent (see, e.g., Hanaoka et al., *J. Am. Soc. Nephrol.* 2000, 11:1179-1187; Brill et al., *Proc. Natl. Acad. Sci. U.S.A.* 1996, 93:10206-10211; Torres et al., *Nat. Clin. Pract. Nephrol.* 2006, 2:40-55; O'Sullivan et al., *Am. J. Kidney Dis.* 1998, 32:976-983; Xu et al., *J. Nephrol.* 2006, 19:529-534; Cotton et al., *Am. J. Kidney Dis.* 1998, 32:1081-1083; Davidow et al., *Kidney Int.* 1996, 50:208-218; Li et al., *Kidney Int.* 2004, 66:1926-1938) and to reduce intestinal fluid loss in secretory diarrheas (see, e.g., Thiagarajah et al., *Gastroenterol.* 2004, 126:511-519; Sonawane et al., *Gastroenterol.* 2007, 132:1234-1244; Kunzelmann et al., *Physiol. Rev.* 2002, 82:245-289).

Previously identified CFTR inhibitors include glibenclamide, diphenylamine-2-carboxylate (DPC), and 5-nitro-2-(3-phenylpropyl-amino)benzoate (NPPB) (see FIG. 1A); however, these inhibitors are non-selective in their action and have low potency. One study reported strong CFTR inhibition by α-aminoazaheterocyclic-methylglyoxal adducts (see, e.g., Routaboul et al., *J. Pharmacol. Exp. Ther.* 2007, 322:1023-1035), though CFTR inhibition was not subsequently confirmed (see, e.g., Sonawane et al., *J. Pharm. Exper. Ther.* 2008, 325:529-535). Two classes of improved CFTR inhibitors have been previously identified by high-throughput screening (see, e.g., U.S. Pat. Nos. 7,235,573; 7,414,037; U.S. Patent Application Publication No. 2008-0064666; Namkung et al., *J. Biol. Chem.* 2009, 284:15916-926; Sonawane et al., *FASEB J.* 2006, 20:130-132; Sonawane et al., *Bioorg. Med. Chem.* 2008, 16:8187-95; Verkman et al., *Nat. Rev. Drug Disc.* 2009, 8:153-171). The thiazolidinone CFTR$_{inh}$-172 compound (see FIG. 1A) acts from the cytoplasmic side of the plasma membrane to block CFTR chloride conductance with IC$_{50}$~0.3-3 μM depending on cell type and membrane potential (see, e.g., Ma et al., *J. Clin. Invest.* 2002, 110:1651-1658). Patch-clamp analysis indicated a voltage-independent channel block mechanism in which CFTR$_{inh}$-172 stabilizes the channel closed state (see, e.g., Taddei et al., *FEBS Lett.* 2004, 558:52-56); CFTR mutagenesis suggested CFTR$_{inh}$-172 interaction at arginine-347 located near the cytoplasmic entrance of the CFTR pore (see, e.g., Caci et al., *Biochem. J.* 2008, 413:135-142). CFTR$_{inh}$-172 has low toxicity, undergoes renal excretion with minimal metabolism, and accumulates in the intestine by enterohepatic recirculation (Sonawane et al., *J. Pharm. Sci.* 2005, 94:134-143). A second compound class, the glycine hydrazides (e.g., GlyH-101, see FIG. 1A), inhibit CFTR with IC$_{50}$~5 μM (see, e.g., Muanprasat et al., *J. Gen. Physiol.* 2004, 124:125-137; U.S. Pat. No. 7,414,037). Patch-clamp analysis showed inward rectifying chloride current following GlyH-101 application with rapid channel flicking, indicating an external pore occlusion mechanism.

The PPQ compounds described herein provide certain advantages compared to thiazolidinone compounds and glycine hydrazide compounds. Inhibition of CFTR activity by the PPQ compounds described herein is voltage-independent and thus advantageous to maintain CFTR inhibition potency in interior membrane negative potential cells. Accordingly, the PPQ CFTR inhibitors may not be subject to membrane potential-dependent cellular partitioning or a decrease in potency (such as indicated by an increase in IC$_{50}$). The most potent PPQ compounds inhibited CFTR chloride conductance with IC$_{50}$~90 nM. Without wishing to be bound by any particular theory, the PPQ compounds described herein stabilize the CFTR channel closed state, which in combination with the neutral charge of the compounds and relatively slow time course of inhibition, suggests that the compounds act at a site on the cytoplasmic-facing surface of CFTR distinct from its pore. An exemplary PPQ compound prevented cyst expansion and reduced the size of pre-formed cysts in a neonatal kidney organ culture model of polycystic kidney disease. The PPQ compounds are therefore useful for administering to patients who have polycystic kidney disease.

Pyrimido-Pyrrolo-Quinoxalinedione (PPQ) Compounds

The PPQ compounds described herein share a fused tetracyclic core structure, more specifically, a pyrimido[4',5'-3,4]pyrrolo[1,2-a]quinoxaline ring system. The numbering system of the fused ring atoms in the PPQ compounds of structure (I) is shown below:

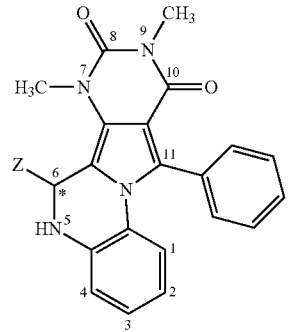

(* indicates a chiral center)

For example, a compound (PPQ105) of the following structure

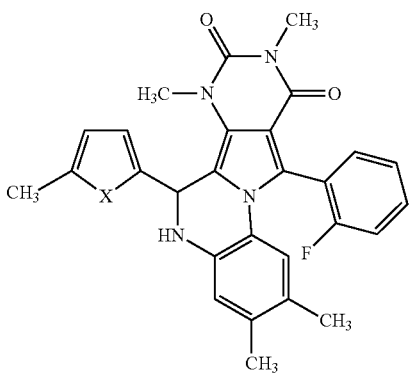

is named herein as 2,3,7,9-Tetramethyl-11-(2-fluorophenyl)-6-(5-methylfuran-2-yl)-5,6-dihydro-pyrimido[4',5'-3,4]pyrrolo[1,2-a]quinoxaline-8,10-(7H,9H)-dione.

Thus, in one embodiment, provided herein is a compound of the following structure (I) and a pharmaceutical composition comprising a physiologically acceptable excipient (i.e., pharmaceutically acceptable or suitable excipient) and the compound of structure (I):

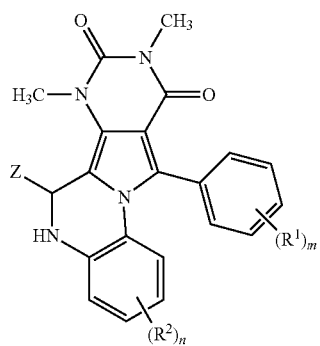

as an isolated enantiomer or a racemic mixture of enantiomers, or as a pharmaceutically acceptable salt, hydrate, solvate, N-oxide or prodrug thereof, wherein:
m is 1, 2, 3, 4 or 5;
n is 1, 2, 3 or 4;
each $R^1$ is the same or different and independently hydrogen, alkyl, halo, or alkoxy;
each $R^2$ is the same or different and independently hydrogen, alkyl, halo or alkoxy; and
Z is aryl or heteroaryl,
wherein the compound is capable of inhibiting cystic fibrosis transmembrane conductance regulator (CFTR)-mediated ion transport.

In certain embodiments, Z is an aryl and is an optionally substituted phenyl. In a more specific embodiment, phenyl is substituted with at least one of alkyl, halo, alkoxy, nitro, or hydroxyl. In other certain embodiments Z is a heteroaryl selected from optionally substituted furanyl, optionally substituted thienyl and optionally substituted 1,3-benzodioxolyl. In a more particular embodiment, Z is furanyl optionally substituted with alkyl. In another particular embodiment, Z is thienyl optionally substituted with alkyl. In another particular embodiment, Z is 1,3-benzodioxol-5-yl.

In a more specific embodiment, Z is a heteroaryl selected from optionally substituted furanyl and optionally substituted thienyl, and the compound of structure (I) can be represented by the following subgenus structure (IA):

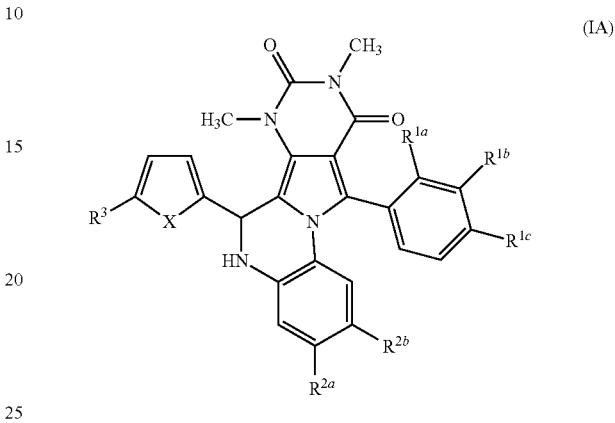

as an isolated enantiomer or a racemic mixture of enantiomers, or as a pharmaceutically acceptable salt, hydrate, solvate, N-oxide or prodrug thereof, wherein:
$R^{1a}$, $R^{1b}$, and $R^{1c}$ are each the same or different and independently hydrogen, alkyl, halo, or alkoxy;
$R^{2a}$ and $R^{2b}$ are each the same or different and independently hydrogen, alkyl, halo, or alkoxy;
$R^3$ is hydrogen or alkyl, and
X is —O—, or —S—,
and wherein the compound is capable of inhibiting cystic fibrosis transmembrane conductance regulator (CFTR)-mediated ion transport.

In certain embodiments, in which X is —O— (i.e., Z is furanyl), $R^{1a}$, $R^{1b}$, and $R^{1c}$ are each the same or different and independently hydrogen, alkyl, halo, or alkoxy; and $R^{2a}$ and $R^{2b}$ are each the same or different and independently hydrogen or alkyl; and $R^3$ is hydrogen or alkyl. In particular embodiments, $R^{2a}$ and $R^{2b}$ are the same and each is hydrogen or each is alkyl. In more particular embodiments, $R^{2a}$ and $R^{2b}$ are the same and each is hydrogen or each is methyl.

In certain embodiments, in which X is —O— (i.e., Z is furanyl), $R^{1a}$, $R^{1b}$, and $R^{1c}$ are each the same or different and independently hydrogen, $C_{1-6}$ alkyl, halo, or $C_{1-6}$ alkoxy; and $R^{2a}$ and $R^{2b}$ are each the same or different and independently hydrogen or $C_{1-6}$ alkyl; and $R^3$ is hydrogen or $C_{1-6}$ alkyl. In particular embodiments, $R^{2a}$ and $R^{2b}$ are the same and each is hydrogen or each is $C_{1-6}$ alkyl. In more particular embodiments, $R^{2a}$ and $R^{2b}$ are the same and each is hydrogen or each is methyl.

In more specific embodiments, in which X is —O— (i.e., Z is furanyl), $R^{1a}$, $R^{1b}$, and $R^{1c}$ are each the same or different and independently hydrogen, methyl, chloro, fluoro, or methoxy; and $R^{2a}$ and $R^{2b}$ are each the same or different and independently hydrogen or methyl; and $R^3$ is hydrogen or methyl. In particular embodiments, $R^{2a}$ and $R^{2b}$ are the same and each is hydrogen or each is methyl.

In certain specific embodiments, the PPQ compounds of substructure (IA) are as follows:

| | | |
|---|---|---|
| PPQ-101 | 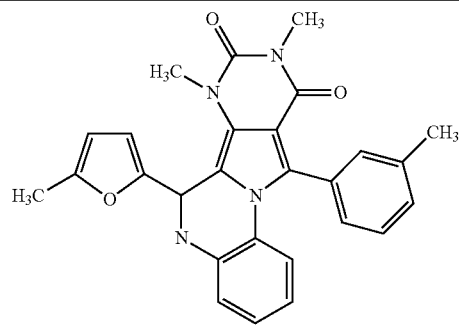 | 7,9-Dimethyl-11-(3-methylphenyl)-6-(5-methylfuran-2-yl)-5,6-dihydro-pyrimido[4',5'-3,4]pyrrolo[1,2-a]quinoxaline-8,10-(7H,9H)-dione |
| PPQ-102 | 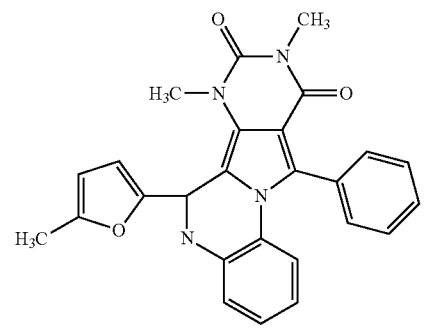 [SMILES: Cc1ccc(C2Nc3ccccc3-n3c(-c4ccccc4)c4c(=O)n(C)c(=O)n(C)c4c32)o1] | 7,9-Dimethyl-11-phenyl-6-(5-methylfuran-2-yl)-5,6-dihydro-pyrimido[4',5'-3,4]pyrrolo[1,2-a]quinoxaline-8,10-(7H,9H)-dione |
| PPQ-103 | 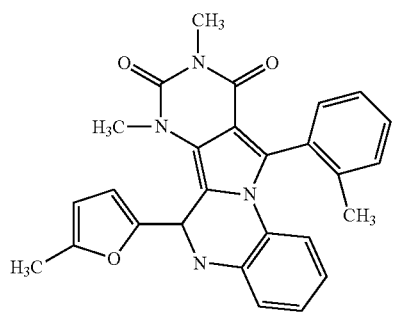 [SMILES: Cc1ccc(C2Nc3ccccc3-n3c(-c4ccccc4C)c4c(=O)n(C)c(=O)n(C)c4c32)o1] | 7,9-Dimethyl-11-(2-methylphenyl)-6-(5-methylfuran-2-yl)-5,6-dihydro-pyrimido[4',5'-3,4]pyrrolo[1,2-a]quinoxaline-8,10-(7H,9H)-dione |
| PPQ-104 | 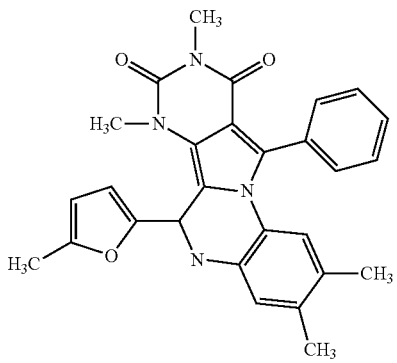 [SMILES: Cc1ccc(C2Nc3cc(C)c(C)cc3-n3c(-c4ccccc4)c4c(=O)n(C)c(=O)n(C)c4c32)o1] | 2,3,7,9-Tetramethyl-11-phenyl-6-(5-methylfuran-2-yl)-5,6-dihydro-pyrimido[4',5'-3,4]pyrrolo[1,2-a]quinoxaline-8,10-(7H,9H)-dione |

-continued

PPQ-105 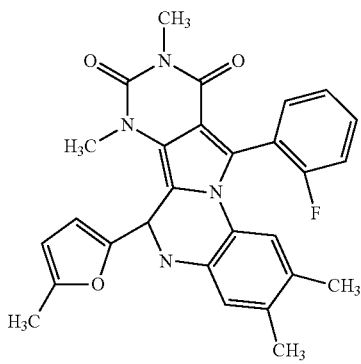 [SMILES: Cc1ccc(C2Nc3cc(C)c(C)cc3-n3c(-c4ccccc4F)c4c(=O)n(C)c(=O)n(C)c4c32)o1] 2,3,7,9-Tetramethyl-11-(2-fluorophenyl)-6-(5-methylfuran-2-yl)-5,6-dihydro-pyrimido[4',5'-3,4]pyrrolo[1,2-a]quinoxaline-8,10-(7H,9H)-dione PPQ-106 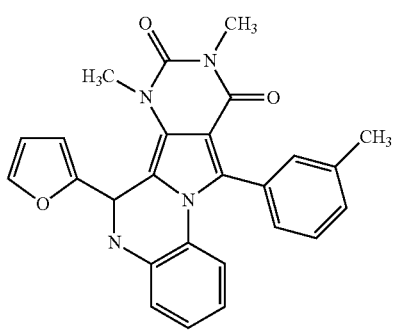 [SMILES: Cc1cccc(-c2c3c(=O)n(C)c(=O)n(C)c3c3n2-c2ccccc2NC3c2ccco2)c1] 7,9-Dimethyl-11-(3-methylphenyl)-6-(furan-2-yl)-5,6-dihydro-pyrimido[4',5'-3,4]pyrrolo[1,2-a]quinoxaline-8,10-(7H,9H)-dione PPQ-107 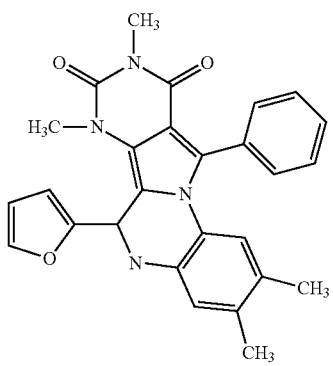 2,3,7,9-Tetramethyl-11-phenyl-6-(furan-2-yl)-5,6-dihydro-pyrimido[4',5'-3,4]pyrrolo[1,2-a]quinoxaline-8,10-(7H,9H)-dione PPQ-108 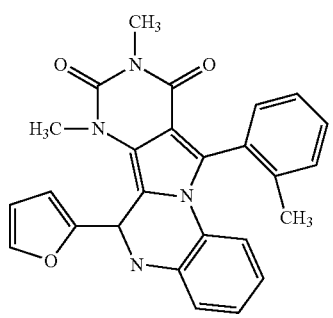 [SMILES: Cc1ccccc1-c1c2c(=O)n(C)c(=O)n(C)c2c2n1-c1ccccc1NC2c1ccco1] 7,9-Dimethyl-11-(2-methylphenyl)-6-(furan-2-yl)-5,6-dihydro-pyrimido[4',5'-3,4]pyrrolo[1,2-a]quinoxaline-8,10-(7H,9H)-dione

| | | |
|---|---|---|
| PPQ-109 | [structure] | 7,9-Dimethyl-11-(4-methoxyphenyl)-6-(5-methylfuran-2-yl)-5,6-dihydro-pyrimido[4',5'-3,4]pyrrolo[1,2-a]quinoxaline-8,10-(7H,9H)-dione |
| PPQ-110 | [structure] | 7,9-Dimethyl-11-(4-methylphenyl)-6-(5-methylfuran-2-yl)-5,6-dihydro-pyrimido[4',5'-3,4]pyrrolo[1,2-a]quinoxaline-8,10-(7H,9H)-dione |
| PPQ-111 | [structure] | 7,9-Dimethyl-11-(4-cholophenyl)-6-(5-methylfuran-2-yl)-5,6-dihydro-pyrimido[4',5'-3,4]pyrrolo[1,2-a]quinoxaline-8,10-(7H,9H)-dione |
| PPQ-112 | [structure] | 7,9-Dimethyl-11-phenyl-6-(5-furan-2-yl)-5,6-dihydro-pyrimido[4',5'-3,4]pyrrolo[1,2-a]quinoxaline-8,10-(7H,9H)-dione |

In other certain embodiments, in which X is —S— (i.e., Z is thienyl), $R^{1a}$, $R^{1b}$, and $R^{1c}$ are each the same or different and independently hydrogen, alkyl, halo, or alkoxy; and $R^{2a}$ and $R^{2b}$ are each the same or different and independently hydrogen or alkyl; and $R^3$ is hydrogen or alkyl. In particular embodiments, $R^{2a}$ and $R^{2b}$ are the same and each is hydrogen or each is alkyl. In more particular embodiments, $R^{2a}$ and $R^{2b}$ are the same and each is hydrogen or each is methyl.

In certain embodiments, in which X is —S— (i.e., Z is thienyl), $R^{1a}$, $R^{1b}$, and $R^{1c}$ are each the same or different and independently hydrogen, $C_{1-6}$ alkyl, halo, or $C_{1-6}$ alkoxy; and $R^{2a}$ and $R^{2b}$ are each the same or different and independently hydrogen or $C_{1-6}$ alkyl; and $R^3$ is hydrogen or $C_{1-6}$ alkyl. In particular embodiments, $R^{2a}$ and $R^{2b}$ are the same and each is hydrogen or each is $C_{1-6}$ alkyl. In more particular embodiments, $R^{2a}$ and $R^{2b}$ are the same and each is hydrogen or each is methyl.

In more specific embodiments, in which X is —S— (i.e., Z is thienyl), $R^{1a}$, $R^{1b}$, and $R^{1c}$ are each the same or different and independently hydrogen, methyl, chloro, fluoro, or methoxy; and $R^{2a}$ and $R^{2b}$ are each the same or different and independently hydrogen or methyl; and $R^3$ is hydrogen or methyl. In particular embodiments, $R^{2a}$ and $R^{2b}$ are the same and each is hydrogen or each is methyl.

In certain specific embodiments, the PPQ compounds of substructure (IA) are as follows:

| | | |
|---|---|---|
| PPQ-113 | 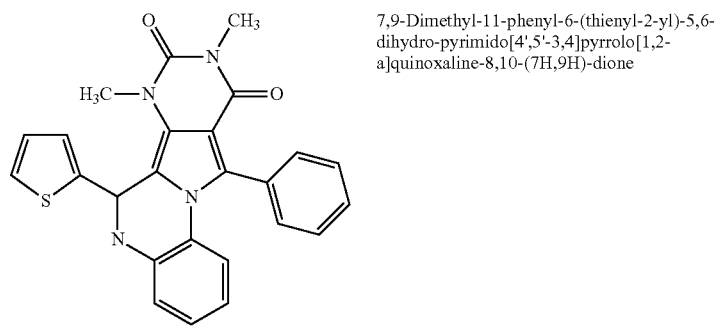 | 7,9-Dimethyl-11-phenyl-6-(thienyl-2-yl)-5,6-dihydro-pyrimido[4',5'-3,4]pyrrolo[1,2-a]quinoxaline-8,10-(7H,9H)-dione |
| PPQ-114 | 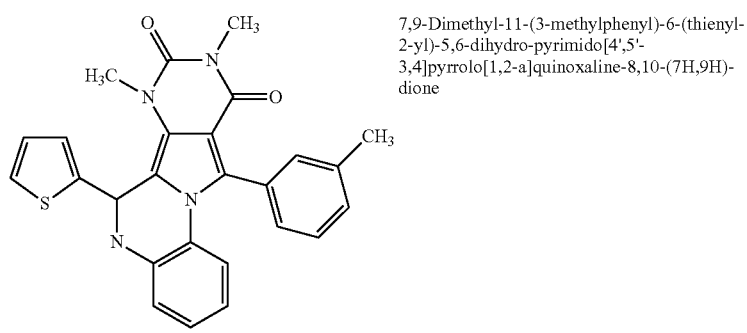 | 7,9-Dimethyl-11-(3-methylphenyl)-6-(thienyl-2-yl)-5,6-dihydro-pyrimido[4',5'-3,4]pyrrolo[1,2-a]quinoxaline-8,10-(7H,9H)-dione |
| PPQ-115 | 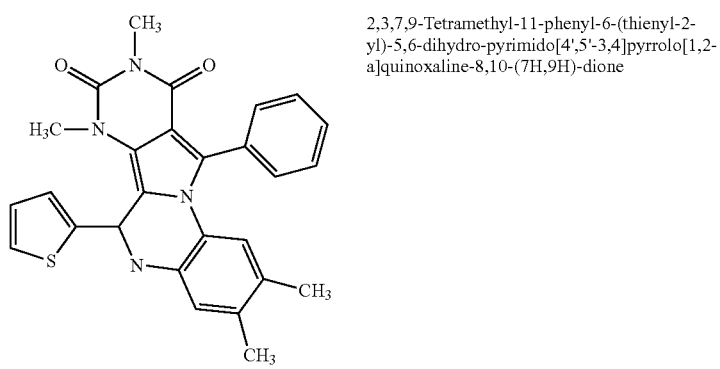 | 2,3,7,9-Tetramethyl-11-phenyl-6-(thienyl-2-yl)-5,6-dihydro-pyrimido[4',5'-3,4]pyrrolo[1,2-a]quinoxaline-8,10-(7H,9H)-dione |
| PPQ-116 | 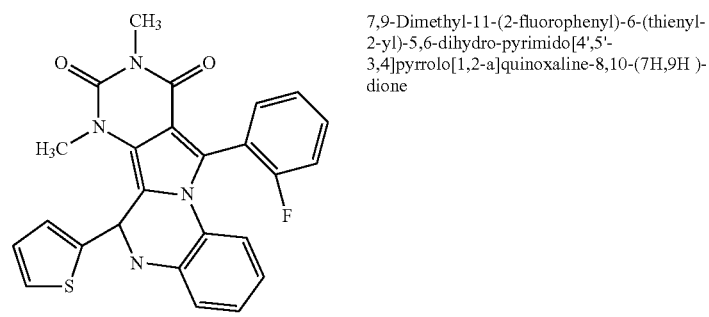 | 7,9-Dimethyl-11-(2-fluorophenyl)-6-(thienyl-2-yl)-5,6-dihydro-pyrimido[4',5'-3,4]pyrrolo[1,2-a]quinoxaline-8,10-(7H,9H)-dione |

| | | |
|---|---|---|
| PPQ-117 | 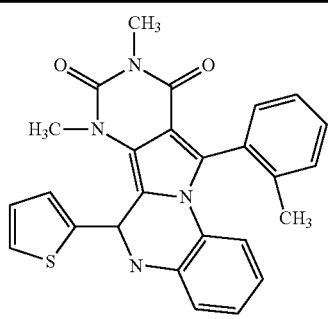 | 7,9-Dimethyl-11-(2-methylphenyl)-6-(thienyl-2-yl)-5,6-dihydro-pyrimido[4',5'-3,4]pyrrolo[1,2-a]quinoxaline-8,10-(7H,9H)-dione |

In another specific embodiment, Z is an optionally substituted phenyl, and the compound of structure (I) can be represented by the following subgenus structure (IB):

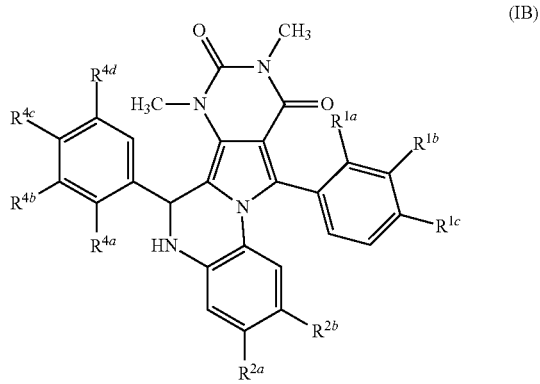

(IB)

as an isolated enantiomer or a racemic mixture of enantiomers, or as a pharmaceutically acceptable salt, hydrate, solvate, N-oxide or prodrug thereof, wherein:

$R^{1a}$, $R^{1b}$, and $R^{1c}$ are each the same or different and independently hydrogen, alkyl, halo, or alkoxy;

$R^{2a}$ and $R^{2b}$ are each the same or different and independently hydrogen, alkyl, halo, or alkoxy; and $R^{4a}$, $R^{4b}$, $R^{4c}$, $R^{4d}$ are each the same or different and independently hydrogen, alkyl, alkenyl, halo, alkoxy, nitro, or hydroxy, and wherein the compound is capable of inhibiting cystic fibrosis transmembrane conductance regulator (CFTR)-mediated ion transport.

In certain embodiments, $R^{1a}$, $R^{1b}$, and $R^{1c}$ are each the same or different and independently hydrogen, alkyl, halo, or alkoxy; $R^{2a}$ and $R^{2b}$ are each the same or different and independently hydrogen or alkyl; and $R^{4a}$, $R^{4b}$, $R^{4c}$, and $R^{4d}$ are each the same or different and independently hydrogen, alkyl, alkenyl, halo, alkoxy, nitro, or hydroxy. In particular embodiments, $R^{2a}$ and $R^{2b}$ are the same and each is hydrogen or each is alkyl. In more particular embodiments, $R^{2a}$ and $R^{2b}$ are the same and each is hydrogen or each is methyl.

In certain embodiments, $R^{1a}$, $R^{1b}$, and $R^{1c}$ are each the same or different and independently hydrogen, $C_{1-6}$ alkyl, halo, or $C_{1-6}$ alkoxy; and $R^{2a}$ and $R^{2b}$ are each the same or different and independently hydrogen or $C_{1-6}$ alkyl; and $R^{4a}$, $R^{4b}$, $R^{4c}$, and $R^{4d}$ are each the same or different and independently hydrogen, $C_{1-6}$ alkyl, halo, $C_{1-6}$ alkoxy, nitro, or hydroxy. In particular embodiments, $R^{2a}$ and $R^{2b}$ are the same and each is hydrogen or each is $C_{1-6}$ alkyl. In more particular embodiments, $R^{2a}$ and $R^{2b}$ are the same and each is hydrogen or each is methyl.

In more specific embodiments, $R^{1a}$, $R^{1b}$, and $R^{1c}$ are each the same or different and independently hydrogen, methyl, chloro, fluoro, or methoxy; and $R^{2a}$ and $R^{2b}$ are each the same or different and independently hydrogen or methyl; and $R^{4a}$, $R^{4b}$, $R^{4c}$, and $R^{4d}$ are each the same or different and independently hydrogen, methyl, chloro, fluoro, methoxy, nitro, or hydroxy. In particular embodiments, $R^{2a}$ and $R^{2b}$ are the same and each is hydrogen or each is methyl.

In certain specific embodiments, the PPQ compounds of substructure (IB) are as follows:

| | | |
|---|---|---|
| PPQ-201 | 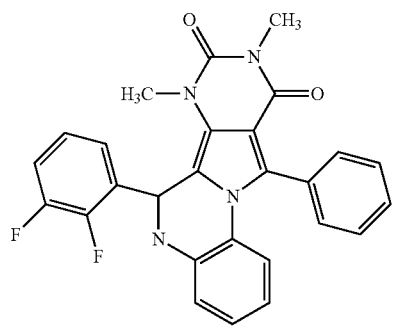 [SMILES: Cn1c(=O)c2c(-c3ccccc3)n3c(c2n(C)c1=O)C(c1cccc(F)c1F)Nc1ccccc1-3] | 7,9-Dimethyl-11-phenyl-6-(2,3-difluorophenyl)-5,6-dihydro-pyrimido[4',5'-3,4]pyrrolo[1,2-a]quinoxaline-8,10-(7H,9H)-dione |

| | | |
|---|---|---|
| PPQ-202 | | 7,9-Dimethyl-11-phenyl-6-(3-nitrophenyl)-5,6-dihydro-pyrimido[4',5'-3,4]pyrrolo[1,2-a]quinoxaline-8,10-(7H,9H)-dione |
| PPQ-203 | | 2,3,7,9-Tetramethyl-11-phenyl-6-(4-hydroxyphenyl)-5,6-dihydro-pyrimido[4',5'-3,4]pyrrolo[1,2-a]quinoxaline-8,10-(7H,9H)-dione |
| PPQ-204 | | 7,9-Dimethyl-11-phenyl-6-(3-methoxyphenyl)-5,6-dihydro-pyrimido[4',5'-3,4]pyrrolo[1,2-a]quinoxaline-8,10-(7H,9H)-dione |
| PPQ-205 | | 7,9-Dimethyl-11-phenyl-6-(2-fluorophenyl)-5,6-dihydro-pyrimido[4',5'-3,4]pyrrolo[1,2-a]quinoxaline-8,10-(7H,9H)-dione |
| PPQ-206 | | 7,9-Dimethyl-11-phenyl-6-phenyl-5,6-dihydro-pyrimido[4',5'-3,4]pyrrolo[1,2-a]quinoxaline-8,10-(7H,9H)-dione |

| | | |
|---|---|---|
| PPQ-207 | 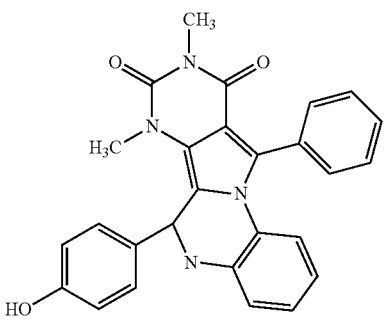 [SMILES: Cn1c(=O)c2c(-c3ccccc3)n3c(c2n(C)c1=O)C(c1ccc(O)cc1)Nc1ccccc1-3] | 7,9-Dimethyl-11-phenyl-6-(4-hydroxyphenyl)-5,6-dihydro-pyrimido[4',5'-3,4]pyrrolo[1,2-a]quinoxaline-8,10-(7H,9H)-dione |
| PPQ-208 | 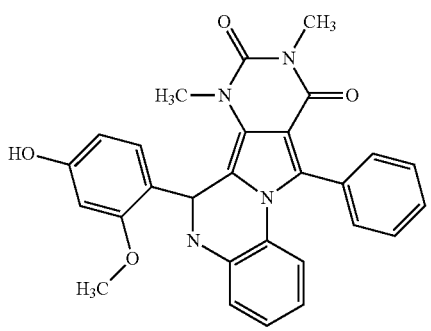 [SMILES: COc1cc(O)ccc1C1Nc2ccccc2-n2c(-c3ccccc3)c3c(=O)n(C)c(=O)n(C)c3c21] | 7,9-Dimethyl-11-phenyl-6-(2-methoxy-4-hydroxyphenyl)-5,6-dihydro-pyrimido[4',5'-3,4]pyrrolo[1,2-a]quinoxaline-8,10-(7H,9H)-dione |
| PPQ-209 | 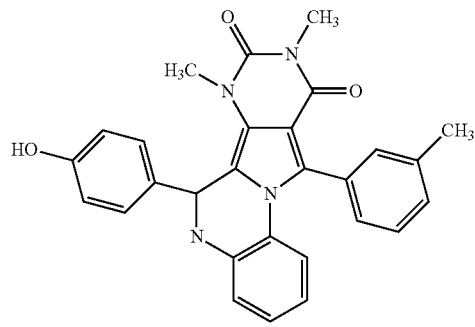 [SMILES: Cc1cccc(-c2c3c(=O)n(C)c(=O)n(C)c3c3n2-c2ccccc2NC3c2ccc(O)cc2)c1] | 7,9-Dimethyl-11-(3-methylphenyl)-6-(4-hydroxyphenyl)-5,6-dihydro-pyrimido[4',5'-3,4]pyrrolo[1,2-a]quinoxaline-8,10-(7H,9H)-dione |
| PPQ-210 | 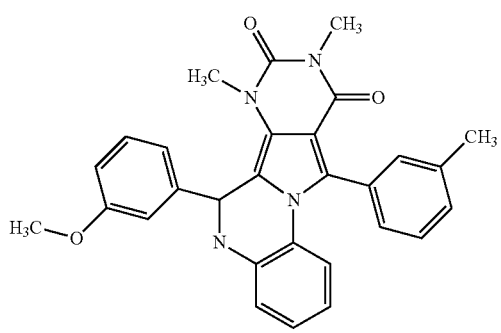 | 7,9-Dimethyl-11-(3-methylphenyl)-6-(3-methoxyphenyl)-5,6-dihydro-pyrimido[4',5'-3,4]pyrrolo[1,2-a]quinoxaline-8,10-(7H,9H)-dione |
| PPQ-211 | 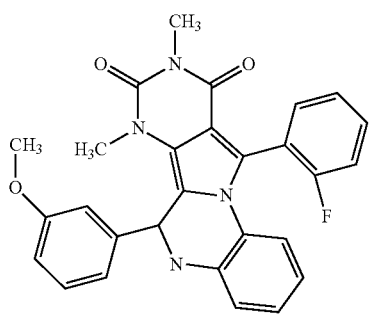 [SMILES: COc1cccc(C2Nc3ccccc3-n3c(-c4ccccc4F)c4c(=O)n(C)c(=O)n(C)c4c32)c1] | 7,9-Dimethyl-11-(2-fluorophenyl)-6-(3-methoxyphenyl)-5,6-dihydro-pyrimido[4',5'-3,4]pyrrolo[1,2-a]quinoxaline-8,10-(7H,9H)-dione |

-continued

| | | |
|---|---|---|
| PPQ-212 | 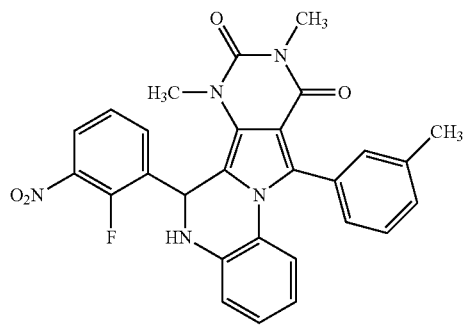 [SMILES: Cc1cccc(-c2c3c(=O)n(C)c(=O)n(C)c3c3n2-c2ccccc2NC3c2cccc([N+](=O)[O-])c2F)c1] | 7,9-Dimethyl-11-(3-methylphenyl)-6-(2-fluoro-3-nitrophenyl)-5,6-dihydro-pyrimido[4',5'-3,4]pyrrolo[1,2-a]quinoxaline-8,10-(7H,9H)-dione |
| PPQ-213 | 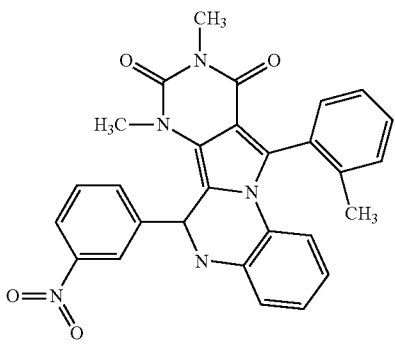 [SMILES: Cc1ccccc1-c1c2c(=O)n(C)c(=O)n(C)c2c2n1-c1ccccc1NC2c1cccc([N+](=O)[O-])c1] | 7,9-Dimethyl-11-(2-methylphenyl)-6-(3-nitrophenyl)-5,6-dihydro-pyrimido[4',5'-3,4]pyrrolo[1,2-a]quinoxaline-8,10-(7H,9H)-dione |
| PPQ-214 | 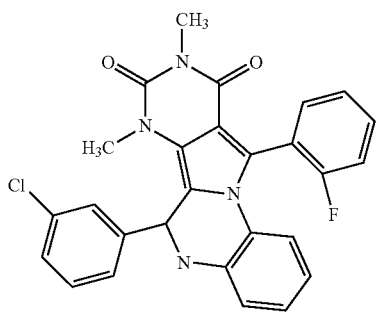 [SMILES: Cn1c(=O)c2c(-c3ccccc3F)n3c(c2n(C)c1=O)C(c1cccc(Cl)c1)Nc1ccccc1-3] | 7,9-Dimethyl-11-(2-fluorophenyl)-6-(3-chlorophenyl)-5,6-dihydro-pyrimido[4',5'-3,4]pyrrolo[1,2-a]quinoxaline-8,10-(7H,9H)-dione |
| PPQ-215 | 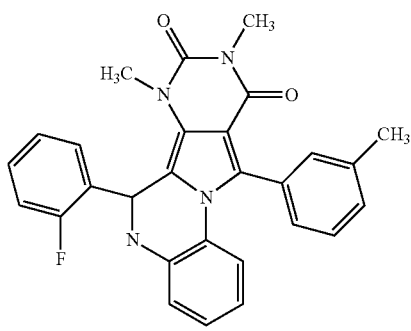 [SMILES: Cc1cccc(-c2c3c(=O)n(C)c(=O)n(C)c3c3n2-c2ccccc2NC3c2ccccc2F)c1] | 7,9-Dimethyl-11-(3-methylphenyl)-6-(2-fluorophenyl)-5,6-dihydro-pyrimido[4',5'-3,4]pyrrolo[1,2-a]quinoxaline-8,10-(7H,9H)-dione |
| PPQ-216 | 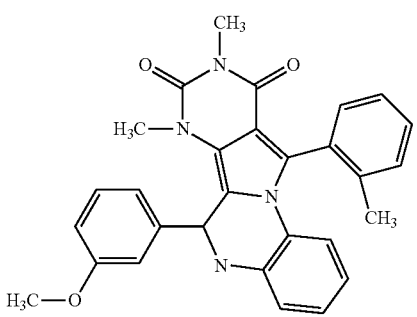 [SMILES: COc1cccc(C2Nc3ccccc3-n3c(-c4ccccc4C)c4c(=O)n(C)c(=O)n(C)c4c32)c1] | 7,9-Dimethyl-11-(2-methylphenyl)-6-(3-methoxyphenyl)-5,6-dihydro-pyrimido[4',5'-3,4]pyrrolo[1,2-a]quinoxaline-8,10-(7H,9H)-dione |

| | | |
|---|---|---|
| PPQ-217 | 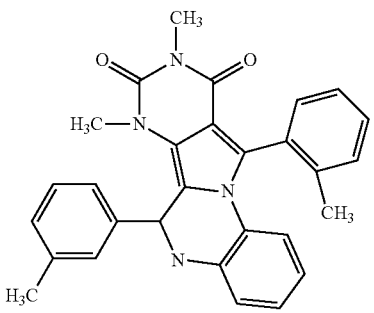 [SMILES: Cc1cccc(C2Nc3ccccc3-n3c(-c4ccccc4C)c4c(=O)n(C)c(=O)n(C)c4c32)c1] | 7,9-Dimethyl-11-(2-methylphenyl)-6-(3-methylphenyl)-5,6-dihydro-pyrimido[4',5'-3,4]pyrrolo[1,2-a]quinoxaline-8,10-(7H,9H)-dione |
| PPQ-218 | 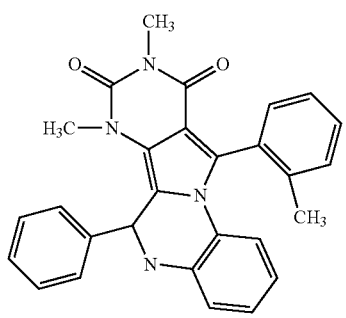 [SMILES: Cc1ccccc1-c1c2c(=O)n(C)c(=O)n(C)c2c2n1-c1ccccc1NC2c1ccccc1] | 7,9-Dimethyl-11-(2-methylphenyl)-6-phenyl-5,6-dihydro-pyrimido[4',5'-3,4]pyrrolo[1,2-a]quinoxaline-8,10-(7H,9H)-dione |
| PPQ-219 | 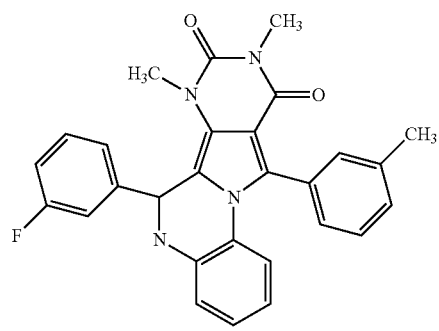 [SMILES: Cc1cccc(-c2c3c(=O)n(C)c(=O)n(C)c3c3n2-c2ccccc2NC3c2cccc(F)c2)c1] | 7,9-Dimethyl-11-(3-methylphenyl)-6-(3-fluorophenyl)-5,6-dihydro-pyrimido[4',5'-3,4]pyrrolo[1,2-a]quinoxaline-8,10-(7H,9H)-dione |
| PPQ-220 | 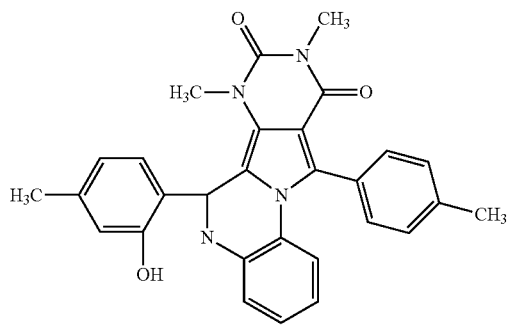 | 7,9-Dimethyl-11-(4-methylphenyl)-6-(2-hydroxy-4-methylphenyl)-5,6-dihydro-pyrimido[4',5'-3,4]pyrrolo[1,2-a]quinoxaline-8,10-(7H,9H)-dione |
| PPQ-221 | 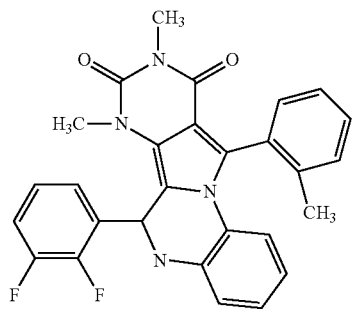 [SMILES: Cc1ccccc1-c1c2c(=O)n(C)c(=O)n(C)c2c2n1-c1ccccc1NC2c1cccc(F)c1F] | 7,9-Dimethyl-11-(2-methylphenyl)-6-(2,3-difluorophenyl)-5,6-dihydro-pyrimido[4',5'-3,4]pyrrolo[1,2-a]quinoxaline-8,10-(7H,9H)-dione |

| | | |
|---|---|---|
| PPQ-222 | 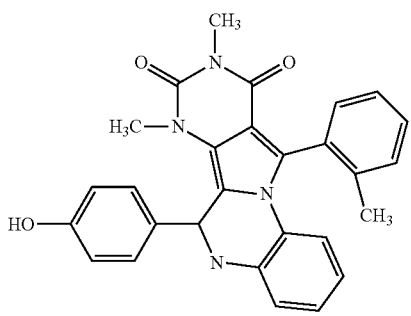 [SMILES: Cc1ccccc1-c1c2c(=O)n(C)c(=O)n(C)c2c2n1-c1ccccc1NC2c1ccc(O)cc1] | 7,9-Dimethyl-11-(2-methylphenyl)-6-(4-hydroxyphenyl)-5,6-dihydro-pyrimido[4',5'-3,4]pyrrolo[1,2-a]quinoxaline-8,10-(7H,9H)-dione |
| PPQ-223 | 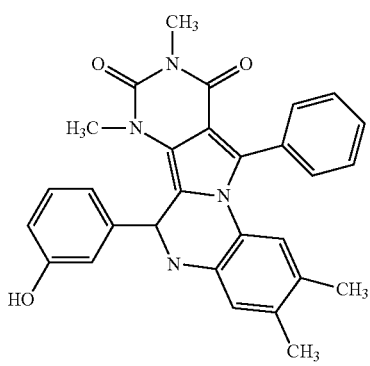 [SMILES: Cc1cc2c(cc1C)-n1c(-c3ccccc3)c3c(=O)n(C)c(=O)n(C)c3c1C(c1cccc(O)c1)N2] | 2,3,7,9-Tetramethyl-11-phenyl-6-(3-hydroxyphenyl)-5,6-dihydro-pyrimido[4',5'-3,4]pyrrolo[1,2-a]quinoxaline-8,10-(7H,9H)-dione |
| PPQ-224 | 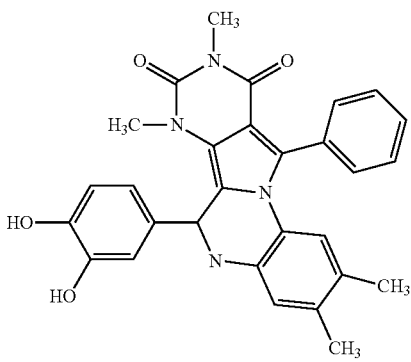 [SMILES: Cc1cc2c(cc1C)-n1c(-c3ccccc3)c3c(=O)n(C)c(=O)n(C)c3c1C(c1ccc(O)c(O)c1)N2] | 2,3,7,9-Tetramethyl-11-phenyl-6-(3,4-dihydroxyphenyl)-5,6-dihydro-pyrimido[4',5'-3,4]pyrrolo[1,2-a]quinoxaline-8,10-(7H,9H)-dione |
| PPQ-225 | 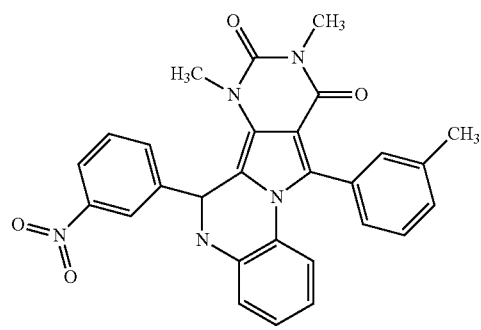 [SMILES: Cc1cccc(-c2c3c(=O)n(C)c(=O)n(C)c3c3n2-c2ccccc2NC3c2cccc([N+](=O)[O-])c2)c1] | 7,9-Dimethyl-11-(3-methylphenyl)-6-(3-nitrophenyl)-5,6-dihydro-pyrimido[4',5'-3,4]pyrrolo[1,2-a]quinoxaline-8,10-(7H,9H)-dione |

-continued

PPQ-226 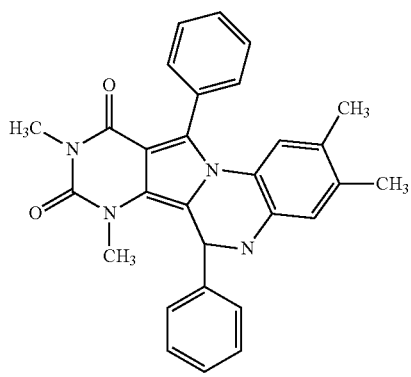 [SMILES: Cc1cc2c(cc1C)-n1c(-c3ccccc3)c3c(=O)n(C)c(=O)n(C)c3c1C(c1ccccc1)N2] 2,3,7,9-Tetramethyl-11-phenyl-6-phenyl-5,6-dihydro-pyrimido[4',5'-3,4]pyrrolo[1,2-a]quinoxaline-8,10-(7H,9H)-dione PPQ-227 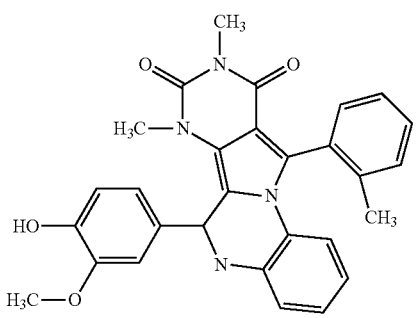 [SMILES: COc1cc(C2Nc3ccccc3-n3c(-c4ccccc4C)c4c(=O)n(C)c(=O)n(C)c4c32)ccc1O] 7,9-Dimethyl-11-(2-methylphenyl)-6-(3-methoxy-4-hydroxyphenyl)-5,6-dihydro-pyrimido[4',5'-3,4]pyrrolo[1,2-a]quinoxaline-8,10-(7H,9H)-dione PPQ-228 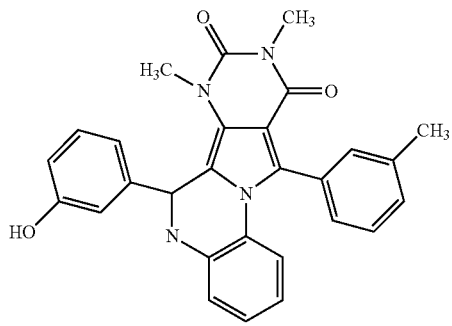 [SMILES: Cc1cccc(-c2c3c(=O)n(C)c(=O)n(C)c3c3n2-c2ccccc2NC3c2cccc(O)c2)c1] 7,9-Dimethyl-11-(3-methylphenyl)-6-(3-hydroxyphenyl)-5,6-dihydro-pyrimido[4',5'-3,4]pyrrolo[1,2-a]quinoxaline-8,10-(7H,9H)-dione PPQ-229 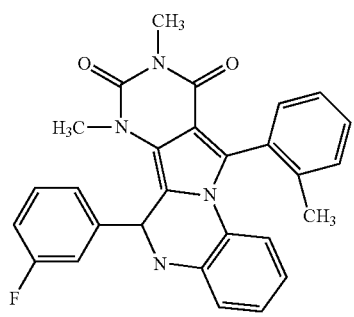 [SMILES: Cc1ccccc1-c1c2c(=O)n(C)c(=O)n(C)c2c2n1-c1ccccc1NC2c1cccc(F)c1] 7,9-Dimethyl-11-(2-methylphenyl)-6-(3-fluorophenyl)-5,6-dihydro-pyrimido[4',5'-3,4]pyrrolo[1,2-a]quinoxaline-8,10-(7H,9H)-dione PPQ-230 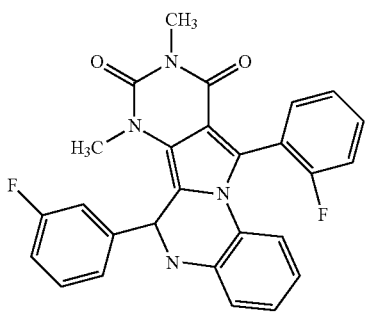 [SMILES: Cn1c(=O)c2c(-c3ccccc3F)n3c(c2n(C)c1=O)C(c1cccc(F)c1)Nc1ccccc1-3] 7,9-Dimethyl-11-(2-fluorophenyl)-6-(3-fluorophenyl)-5,6-dihydro-pyrimido[4',5'-3,4]pyrrolo[1,2-a]quinoxaline-8,10-(7H,9H)-dione -continued PPQ-231 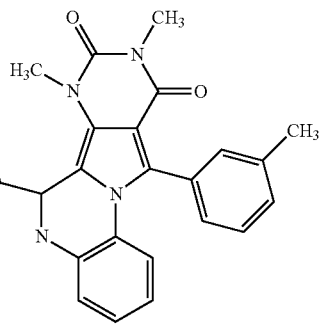 7,9-Dimethyl-11-(3-methylphenyl)-6-(2-ethoxyphenyl)-5,6-dihydro-pyrimido[4',5'-3,4]pyrrolo[1,2-a]quinoxaline-8,10-(7H,9H)-dione PPQ-232 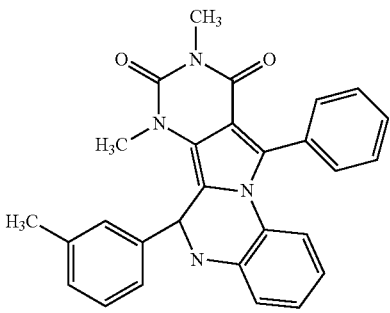 [SMILES: Cc1cccc(C2Nc3ccccc3-n3c(-c4ccccc4)c4c(=O)n(C)c(=O)n(C)c4c32)c1] 7,9-Dimethyl-11-phenyl-6-(3-methylphenyl)-5,6-dihydro-pyrimido[4',5'-3,4]pyrrolo[1,2-a]quinoxaline-8,10-(7H,9H)-dione PPQ-233 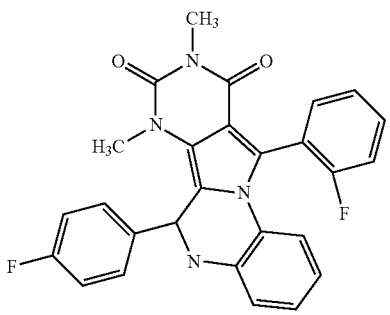 7,9-Dimethyl-11-(2-fluorophenyl)-6-(4-fluorophenyl)-5,6-dihydro-pyrimido[4',5'-3,4]pyrrolo[1,2-a]quinoxaline-8,10-(7H,9H)-dione PPQ-234 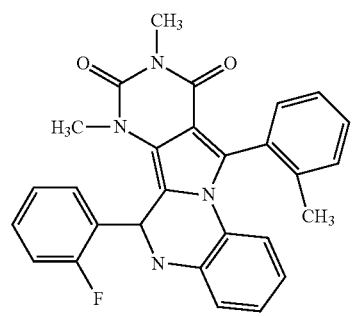 [SMILES: Cc1ccccc1-c1c2c(=O)n(C)c(=O)n(C)c2c2n1-c1ccccc1NC2c1ccccc1F] 7,9-Dimethyl-11-(2-methylphenyl)-6-(2-fluorophenyl)-5,6-dihydro-pyrimido[4',5'-3,4]pyrrolo[1,2-a]quinoxaline-8,10-(7H,9H)-dione PPQ-235 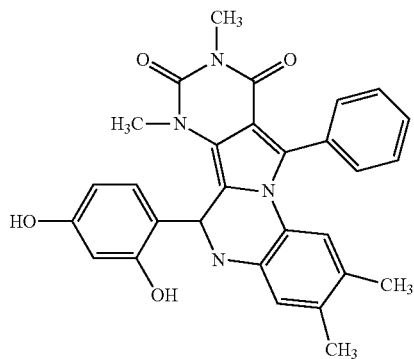 [SMILES: Cc1cc2c(cc1C)-n1c(-c3ccccc3)c3c(=O)n(C)c(=O)n(C)c3c1C(c1ccc(O)cc1O)N2] 2,3,7,9-Tetramethyl-11-phenyl-6-(2,4-dihydroxyphenyl)-5,6-dihydro-pyrimido[4',5'-3,4]pyrrolo[1,2-a]quinoxaline-8,10-(7H,9H)-dione PPQ-236 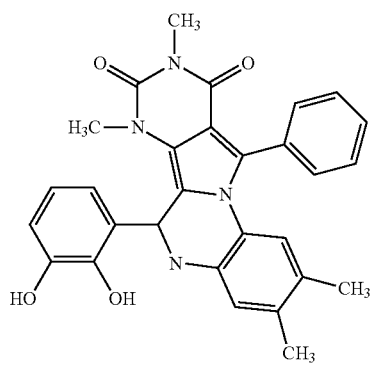 [SMILES: Cc1cc2c(cc1C)-n1c(-c3ccccc3)c3c(=O)n(C)c(=O)n(C)c3c1C(c1cccc(O)c1O)N2] 2,3,7,9-Tetramethyl-11-phenyl-6-(2,3-dihydroxyphenyl)-5,6-dihydro-pyrimido[4',5'-3,4]pyrrolo[1,2-a]quinoxaline-8,10-(7H,9H)-dione PPQ-237 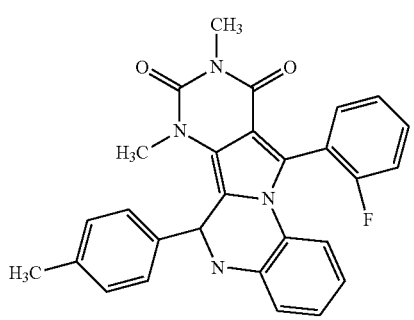 [SMILES: Cc1ccc(C2Nc3ccccc3-n3c(-c4ccccc4F)c4c(=O)n(C)c(=O)n(C)c4c32)cc1] 7,9-Dimethyl-11-(2-fluorophenyl)-6-(4-methylphenyl)-5,6-dihydro-pyrimido[4',5'-3,4]pyrrolo[1,2-a]quinoxaline-8,10-(7H,9H)-dione PPQ-238 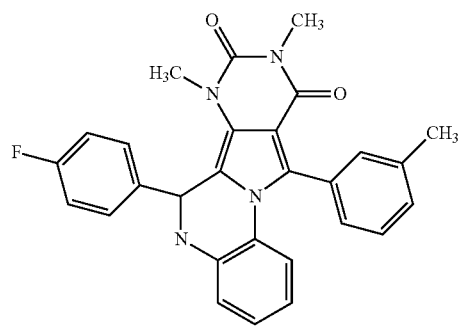 [SMILES: Cc1cccc(-c2c3c(=O)n(C)c(=O)n(C)c3c3n2-c2ccccc2NC3c2ccc(F)cc2)c1] 7,9-Dimethyl-11-(3-methylphenyl)-6-(4-fluorophenyl)-5,6-dihydro-pyrimido[4',5'-3,4]pyrrolo[1,2-a]quinoxaline-8,10-(7H,9H)-dione PPQ-239 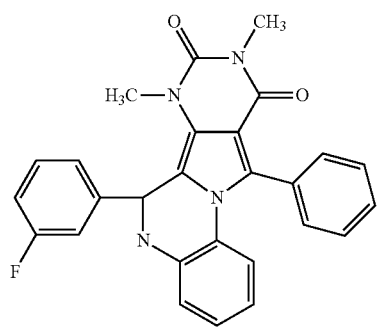 [SMILES: Cn1c(=O)c2c(-c3ccccc3)n3c(c2n(C)c1=O)C(c1cccc(F)c1)Nc1ccccc1-3] 7,9-Dimethyl-11-phenyl-6-(3-fluorophenyl)-5,6-dihydro-pyrimido[4',5'-3,4]pyrrolo[1,2-a]quinoxaline-8,10-(7H,9H)-dione

| | | |
|---|---|---|
| PPQ-240 | 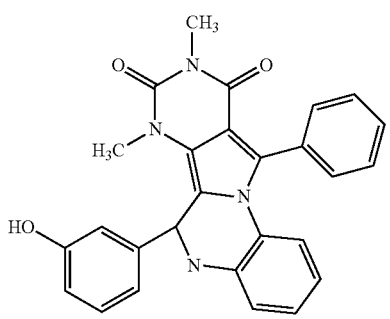 [SMILES: Cn1c(=O)c2c(-c3ccccc3)n3c(c2n(C)c1=O)C(c1cccc(O)c1)Nc1ccccc1-3] | 7,9-Dimethyl-11-phenyl-6-(3-hydroxyphenyl)-5,6-dihydro-pyrimido[4',5'-3,4]pyrrolo[1,2-a]quinoxaline-8,10-(7H,9H)-dione |
| PPQ-241 | 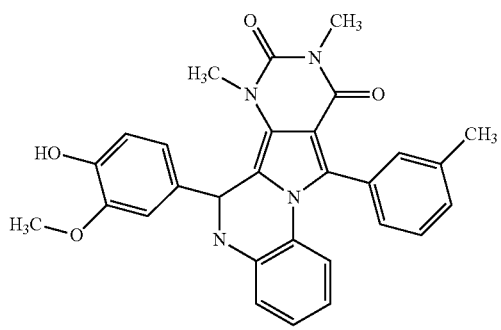 | 7,9-Dimethyl-11-(3-methylphenyl)-6-(3-methoxy-4-hydroxyphenyl)-5,6-dihydro-pyrimido[4',5'-3,4]pyrrolo[1,2-a]quinoxaline-8,10-(7H,9H)-dione |
| PPQ-242 | 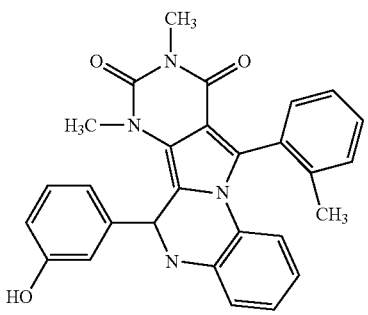 [SMILES: Cc1ccccc1-c1c2c(=O)n(C)c(=O)n(C)c2c2n1-c1ccccc1NC2c1cccc(O)c1] | 7,9-Dimethyl-11-(2-methylphenyl)-6-(3-hydroxyphenyl)-5,6-dihydro-pyrimido[4',5'-3,4]pyrrolo[1,2-a]quinoxaline-8,10-(7H,9H)-dione |
| PPQ-243 | 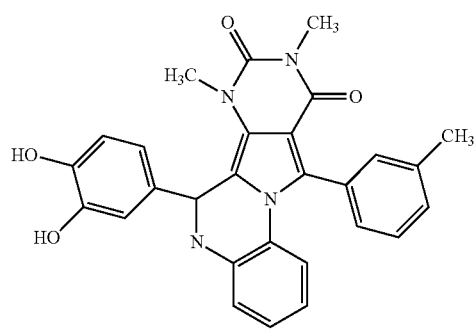 [SMILES: Cc1cccc(-c2c3c(=O)n(C)c(=O)n(C)c3c3n2-c2ccccc2NC3c2ccc(O)c(O)c2)c1] | 7,9-Dimethyl-11-(3-methylphenyl)-6-(3,4-dihydroxyphenyl)-5,6-dihydro-pyrimido[4',5'-3,4]pyrrolo[1,2-a]quinoxaline-8,10-(7H,9H)-dione |
| PPQ-244 | 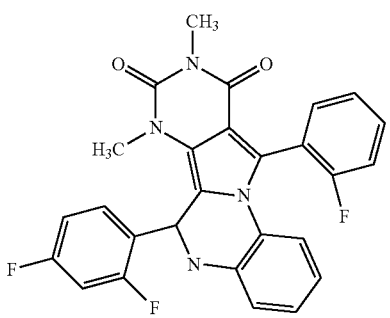 [SMILES: Cn1c(=O)c2c(-c3ccccc3F)n3c(c2n(C)c1=O)C(c1ccc(F)cc1F)Nc1ccccc1-3] | 7,9-Dimethyl-11-(2-fluorophenyl)-6-(2,4-difluorophenyl)-5,6-dihydro-pyrimido[4',5'-3,4]pyrrolo[1,2-a]quinoxaline-8,10-(7H,9H)-dione |

PPQ-245 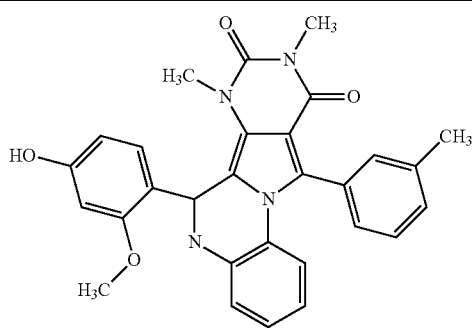 7,9-Dimethyl-11-(3-methylphenyl)-6-(2-methoxy-4-hydroxyphenyl)-5,6-dihydro-pyrimido[4',5'-3,4]pyrrolo[1,2-a]quinoxaline-8,10-(7H,9H)-dione PPQ-246 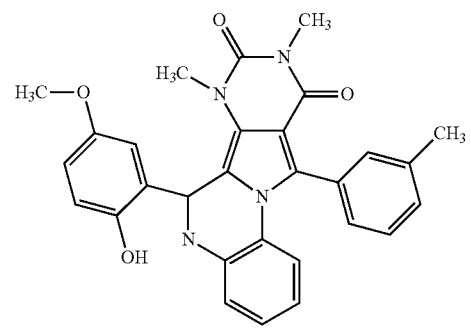 7,9-Dimethyl-11-(3-methylphenyl)-6-(2-hydroxy-5-methoxylphenyl)-5,6-dihydro-pyrimido[4',5'-3,4]pyrrolo[1,2-a]quinoxaline-8,10-(7H,9H)-dione PPQ-247 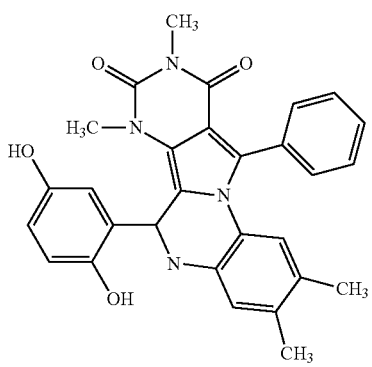 [SMILES: Cc1cc2c(cc1C)-n1c(-c3ccccc3)c3c(=O)n(C)c(=O)n(C)c3c1C(c1cc(O)ccc1O)N2] 2,3,7,9-Tetramethyl-11-phenyl-6-(2,5-dihydroxyphenyl)-5,6-dihydro-pyrimido[4',5'-3,4]pyrrolo[1,2-a]quinoxaline-8,10-(7H,9H)-dione PPQ-248 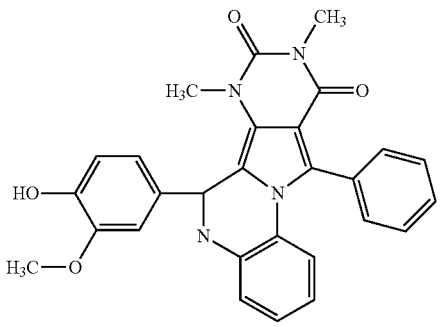 [SMILES: COc1cc(C2Nc3ccccc3-n3c(-c4ccccc4)c4c(=O)n(C)c(=O)n(C)c4c32)ccc1O] 7,9-Dimethyl-11-phenyl-6-(3-methoxy-4-hydroxyphenyl)-5,6-dihydro-pyrimido[4',5'-3,4]pyrrolo[1,2-a]quinoxaline-8,10-(7H,9H)-dione

| | | |
|---|---|---|
| PPQ-249 | 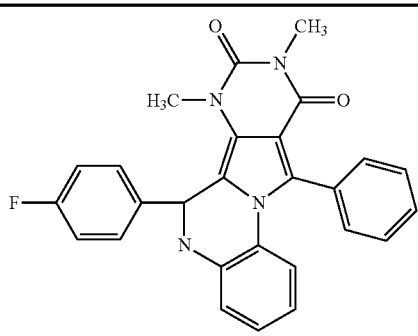 | 7,9-Dimethyl-11-phenyl-6-(4-fluorophenyl)-5,6-dihydro-pyrimido[4',5'-3,4]pyrrolo[1,2-a]quinoxaline-8,10-(7H,9H)-dione |
| PPQ-250 | 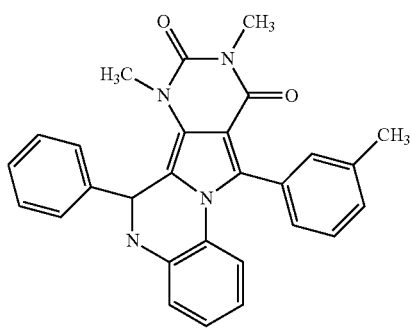 [SMILES: Cc1cccc(-c2c3c(=O)n(C)c(=O)n(C)c3c3n2-c2ccccc2NC3c2ccccc2)c1] | 7,9-Dimethyl-11-(3-methylphenyl)-6-phenyl-5,6-dihydro-pyrimido[4',5'-3,4]pyrrolo[1,2-a]quinoxaline-8,10-(7H,9H)-dione |
| PPQ-251 | 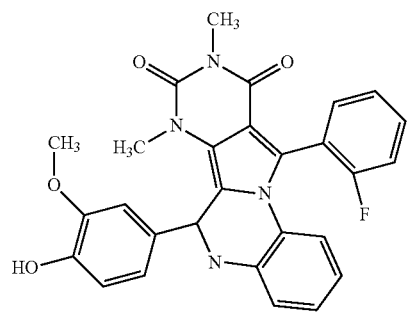 [SMILES: COc1cc(C2Nc3ccccc3-n3c(-c4ccccc4F)c4c(=O)n(C)c(=O)n(C)c4c32)ccc1O] | 7,9-Dimethyl-11-(2-fluorophenyl)-6-(3-methoxy-4-hydroxyphenyl)-5,6-dihydro-pyrimido[4',5'-3,4]pyrrolo[1,2-a]quinoxaline-8,10-(7H,9H)-dione |
| PPQ-252 | 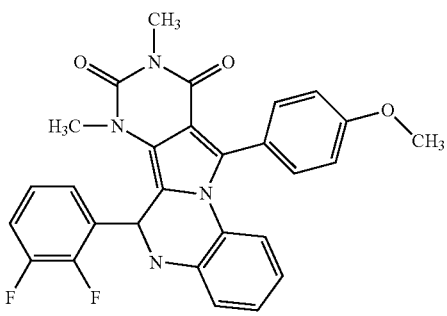 [SMILES: COc1ccc(-c2c3c(=O)n(C)c(=O)n(C)c3c3n2-c2ccccc2NC3c2cccc(F)c2F)cc1] | 7,9-Dimethyl-11-(4-methoxyphenyl)-6-(2,3-difluorophenyl)-5,6-dihydro-pyrimido[4',5'-3,4]pyrrolo[1,2-a]quinoxaline-8,10-(7H,9H)-dione |

In a further embodiment, a compound of structure (I) is provided wherein Z is an optionally substituted 1,3-benzodioxolyl, each $R^1$ is the same or different and independently hydrogen, alkyl, halo, or alkoxy; and each $R^2$ is the same or different and independently hydrogen or alkyl.

In particular embodiments, m is 1, and n is 0. In other embodiments, m is 1 and n is 2.

In other certain embodiments, a compound of structure (I) is provided in which Z is an optionally substituted 1,3-benzodioxolyl, each $R^1$ is the same or different and independently hydrogen, $C_{1-6}$ alkyl, halo, or $C_{1-6}$ alkoxy; and each $R^2$ is the same or different and independently hydrogen or $C_{1-6}$ alkyl. In particular embodiments, m is 1, and $R^1$ is $C_{1-6}$ alkyl.

In more specific embodiments, a compound of structure (I) is provided in which Z is an optionally substituted 1,3-benzodioxolyl, each R¹ is the same or different and independently hydrogen, methyl, chloro, fluoro, or methoxy; and each R² is the same or different and independently hydrogen or methyl. In particular embodiments, m is 1, n is 0, and R¹ is methyl. In other embodiments, m is 0 and n is 0.

In certain specific embodiments, the PPQ compounds of structure (I) are as follows:

atoms that are to be found in the indicated chemical group. For example; $C_{1-6}$ alkyl describes an alkyl group, as defined below, having a total of 1 to 6 carbon atoms. The total number of carbons in the shorthand notation does not include carbons that may exist in substituents of the group described. In addition to the foregoing, as used herein, unless specified to the contrary, the following terms have the meaning indicated.

PPQ-301

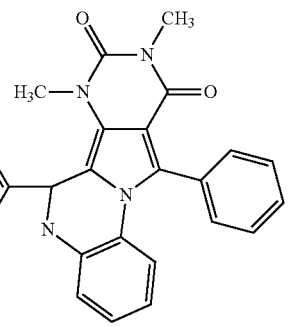

7,9-Dimethyl-11-phenyl-6-(1,3-benzodioxol-5-yl)-5,6-dihydro-pyrimido[4',5'-3,4]pyrrolo[1,2-a]quinoxaline-8,10-(7H,9H)-dione

PPQ-302

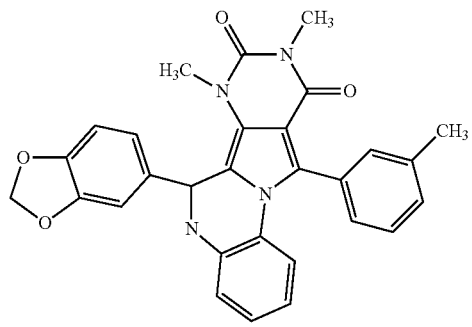 [SMILES: Cc1cccc(-c2c3c(=O)n(C)c(=O)n(C)c3c3n2-c2ccccc2NC3c2ccc3c(c2)OCO3)c1]

7,9-Dimethyl-11-(3-methylphenyl)-6-(1,3-benzodioxol-5-yl)-5,6-dihydro-pyrimido[4',5'-3,4]pyrrolo[1,2-a]quinoxaline-8,10-(7H,9H)-dione The above-described PPQ compounds and compositions comprising the compounds are capable of inhibiting (i.e., slowing, retarding, decreasing, reducing) CFTR-mediated ion transport (i.e., inhibiting in a statistically significant, clinically significant, and/or biologically significant manner), for example, inhibiting CFTR-mediated chloride ion (i.e., Cl⁻) transport. In other embodiments provided herein, the PPQ compounds and compositions comprising the PPQ compounds described above and herein may be used in methods for treating a disease, condition, or disorder that is treatable by inhibiting CFTR-mediated ion transport. Exemplary diseases, conditions, and disorders include but are not limited to polycystic kidney disease (PKD) (including autosomal dominant PDK and autosomal recessive PKD), aberrantly increased intestinal fluid secretion, and secretory diarrhea. In particular embodiments, the PPQ compounds and compositions comprising the PPQ compounds may be used in methods for inhibiting (i.e., preventing, delaying, slowing) cyst formation (i.e., reducing the likelihood of occurrence of one or more cysts forming) and/or inhibiting cyst enlargement or expansion (i.e., slowing, reducing, preventing, retarding, reversing, decreasing cyst enlargement or expansion), particularly inhibiting cyst formation or inhibiting cyst enlargement in one or both kidneys of a human or non-human animal. Inhibiting cyst enlargement or expansion may thus reduce or decrease the volume of one or more fluid-filled cysts. Each of these methods and uses is described in greater detail herein.

Chemistry Definitions

Certain chemical groups named herein are preceded by a shorthand notation indicating the total number of carbon "Alkyl" means a straight chain or branched, noncyclic or cyclic, unsaturated or saturated aliphatic hydrocarbon containing from 1 to 12 carbon atoms, while the terms "lower alkyl" and "$C_{1-6}$ alkyl" have the same meaning as alkyl but contain from 1 to 6 carbon atoms. Representative saturated straight chain alkyls include methyl, ethyl, n-propyl, n-butyl, n-pentyl, n-hexyl, and the like, while saturated branched alkyls include isopropyl, sec-butyl, isobutyl, tert-butyl, isopentyl, and the like. Representative saturated cyclic alkyls include cyclopropyl, cyclobutyl, cyclopentyl, cyclohexyl, —CH₂cyclopropyl, —CH₂cyclobutyl, —CH₂cyclopentyl, —CH₂cyclohexyl, and the like; unsaturated cyclic alkyls include cyclopentenyl and cyclohexenyl, and the like. Cyclic alkyls, also referred to as "homocyclic rings," include di- and poly-homocyclic rings such as decalin and adamantyl. Unsaturated alkyls contain at least one double or triple bond between adjacent carbon atoms (referred to as an "alkenyl" or "alkynyl," respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; representative straight chain and branched alkynyls include acetylenyl, propynyl, 1-butynyl, 2-butynyl, 1-pentynyl, 2-pentynyl, 3-methyl-1 butynyl, and the like. Unless otherwise specified, it is understood that within the context of the current disclosure, the term "alkyl" can be optionally substituted, i.e., "optionally substituted alkyl" encompasses unsubstituted alkyl and substituted alkyl as defined herein.

As used herein, the term "substituted" in the context of alkyl, alkenyl, aryl, heteroaryl, and alkoxy means that at least one hydrogen atom of the alky, aryl, and heteroaryl moiety is replaced with a substituent. In the instance of an oxo substituent ("=O") two hydrogen atoms are replaced. A "substituent" as used within the context of this disclosure includes oxo, halogen, hydroxy, cyano, nitro, amino, alkylamino, dialkylamino, alkyl, alkoxy, thioalkyl, haloalkyl, substituted alkyl, heteroalkyl, aryl, substituted aryl, arylalkyl, substituted arylalkyl, heteroaryl, substituted heteroaryl, heteroarylalkyl, substituted heteroarylalkyl, heterocycle, substituted heterocycle, heterocyclealkyl, substituted heterocyclealkyl, —NR$_a$R$_b$, —NR$_a$C(=O)OR$_b$, —NR$_a$C(=O)NR$_a$R$_b$, —NR$_a$C(=O)OR$_b$—NR$_a$S(=O)$_2$R$_b$, —OR$_a$, —C(=O)R$_a$—C(=O)OR$_a$, —C(=O)NR$_a$R$_b$, —OCH$_2$C(=O)NR$_a$R$_b$, —OC(=O)NR$_a$R$_b$, —SH, —SR$_a$, —SOR$_a$, —S(=O)$_2$NR$_a$R$_b$, —S(=O)$_2$R$_a$, —SR$_a$C(=O)NR$_a$R$_b$, —OS(=O)$_2$R$_a$ and —S(=O)$_2$OR$_a$, wherein R$_a$ and R$_b$ are the same or different and independently hydrogen, alkyl, haloalkyl, substituted alkyl, alkoxy, aryl, substituted aryl, arylalkyl, substituted arylalkyl, heteroaryl, substituted heteroaryl, heteroarylalkyl, substituted heteroarylalkyl, heterocycle, substituted heterocycle, heterocyclealkyl or substituted heterocyclealkyl.

Representative substituents include (but are not limited to) alkoxy (i.e., alkyl-O—, e.g., methoxy, ethoxy, propoxy, butoxy, pentoxy), aryloxy (e.g., phenoxy, chlorophenoxy, tolyloxy, methoxyphenoxy, benzyloxy, alkyloxycarbonylphenoxy, alkyloxycarbonyloxy, acyloxyphenoxy), acyloxy (e.g., propionyloxy, benzoyloxy, acetoxy), carbamoyloxy, carboxy, mercapto, alkylthio, acylthio, arylthio (e.g., phenylthio, chlorophenylthio, alkylphenylthio, alkoxyphenylthio, benzylthio, alkyloxycarbonyl-phenylthio), amino (e.g., amino, mono- and di-C$_{1-3}$ alkanylamino, methylphenylamino, methylbenzylamino, C$_{1-3}$ alkanylamido, acylamino, carbamamido, ureido, guanidino, nitro and cyano). Moreover, any substituent may have from 1-5 further substituents attached thereto.

"Alkenyl" refers to a straight or branched hydrocarbon chain radical group consisting solely of carbon and hydrogen atoms, containing at least one double bond, and having from two to twelve carbon atoms. In certain embodiments, an alkenyl may comprise two to eight carbon atoms. In other embodiments, an alkenyl may comprise two to four carbon atoms. The alkenyl is connected to the rest of the molecule by a single bond, for example, ethenyl (i.e., vinyl), prop-1-enyl (i.e., allyl), but-1-enyl, pent-1-enyl, penta-1,4-dienyl, and the like. Unless otherwise specified, it is understood that within the context of the current disclosure, the term "alkenyl" can be optionally substituted, i.e., "optionally substituted alkenyl" encompasses unsubstituted alkyl and substituted alkenyl as defined herein.

"Aryl" refers to aromatic monocyclic or multicyclic hydrocarbon ring system consisting only of hydrogen and carbon and containing from six to eighteen carbon atoms, where the ring system may be partially or fully saturated. Aryl groups include, but are not limited to, groups such as fluorenyl, phenyl and naphthyl. Unless otherwise specified, it is understood that within the context of the current disclosure, the term "aryl" can be optionally substituted, i.e., "optionally substituted aryl" encompasses unsubstituted aryl and substituted aryl (e.g., substituted phenyl) as defined herein.

"Heteroaryl" means an aromatic heterocycle ring of 5- to 10 members and having at least one heteroatom selected from nitrogen, oxygen and sulfur, and containing at least 1 carbon atom, including monocyclic, bicyclic and tricyclic ring systems. A fused heteroaryl (e.g., a bicyclic heteroaryl) contains at least one aromatic ring, which may be a benzo ring (e.g., benzofuranyl, 1,3-benzodioxolyl or indolyl). Representative heteroaryls are furanyl, benzofuranyl, thienyl, benzothienyl, 1,3-benzodioxolyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl. Unless otherwise specified, it is understood that within the context of the current disclosure, the term "heteroaryl" can be optionally substituted, i.e., "optionally substituted heteroaryl" encompasses unsubstituted heteroaryl and substituted heteroaryl (e.g., substituted furanyl) as defined herein.

"Heterocycle" (also referred to herein as a "heterocyclic ring") means a 4- to 7-membered monocyclic, or 7- to 10-membered bicyclic, heterocyclic ring which is either saturated, unsaturated, or aromatic, and which contains from 1 to 4 heteroatoms independently selected from nitrogen, oxygen and sulfur, and wherein the nitrogen and sulfur heteroatoms may be optionally oxidized, and the nitrogen heteroatom may be optionally quaternized, including bicyclic rings in which any of the above heterocycles are fused to a benzene ring. The heterocycle may be attached via any heteroatom or carbon atom. Heterocycles include heteroaryls as defined above. Thus, in addition to the heteroaryls listed above, heterocycles also include morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

"Halogen" or "halo" means fluoro, chloro, bromo, and iodo.

"Alkoxy" refers to the radical: —O-alkyl, such as methoxy, ethoxy, and the like. C$_{1-6}$ alkoxy means that the alkyl moiety is C$_{1-6}$ alkyl.

With regard to stereoisomers, the compounds of structure (I), as well as any sub-structure herein (e.g., IA and IB), may have one or more chiral centers (for example, at the 6 position of the pyrimido[4',5'-3,4]pyrrolo[1,2-a]quinoxaline ring system). Thus, the compounds may occur in any isomeric form, including racemates, racemic mixtures, and as individual enantiomers or diastereomers. Furthermore, some of the crystalline forms of any compound described herein may exist as polymorphs, which are also included and contemplated by the present disclosure. In addition, some of the compounds may form solvates with water or other organic solvents. Such solvates are similarly included within the scope of compounds and compositions described herein.

In general, the compounds used in the reactions described herein may be made according to organic synthesis techniques known to those skilled in this art, starting from commercially available chemicals and/or from compounds described in the chemical literature. "Commercially available chemicals" may be obtained from standard commercial sources including Acros Organics (Pittsburgh Pa.), Aldrich Chemical (Milwaukee Wis., including Sigma Chemical and Fluka), Apin Chemicals Ltd. (Milton Park UK), Avocado Research (Lancashire U.K.), BDH Inc. (Toronto, Canada), Bionet (Cornwall, U.K.), Chemservice Inc. (West Chester Pa.), Crescent Chemical Co. (Hauppauge N.Y.), Eastman Organic Chemicals, Eastman Kodak Company (Rochester N.Y.), Fisher Scientific Co. (Pittsburgh Pa.), Fisons Chemicals (Leicestershire UK), Frontier Scientific (Logan Utah), ICN Biomedicals, Inc. (Costa Mesa Calif.), Key Organics (Cornwall U.K.), Lancaster Synthesis (Windham N.H.), Maybridge Chemical Co. Ltd. (Cornwall U.K.), Parish Chemical Co. (Orem Utah), Pfaltz & Bauer, Inc. (Waterbury Conn.), Polyorganix (Houston Tex.), Pierce Chemical Co.

(Rockford Ill.), Riedel de Haen AG (Hanover, Germany), Spectrum Quality Product, Inc. (New Brunswick, N.J.), TCI America (Portland Oreg.), Trans World Chemicals, Inc. (Rockville Md.), and Wako Chemicals USA, Inc. (Richmond Va.).

Methods known to one of ordinary skill in the art may be identified through various reference books and databases. Suitable reference books and treatise that detail the synthesis of reactants useful in the preparation of compounds of the present disclosure, or provide references to articles that describe the preparation, include for example, "Synthetic Organic Chemistry," John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure," 4th Ed., Wiley-Interscience, New York, 1992. Additional suitable reference books and treatise that detail the synthesis of reactants useful in the preparation of compounds of the present disclosure, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Quin, L. D. et al. "A Guide to Organophosphorus Chemistry" (2000) Wiley-Interscience, ISBN: 0-471-31824-8; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

Specific and analogous reactants may also be identified through the indices of known chemicals prepared by the Chemical Abstract Service of the American Chemical Society, which are available in most public and university libraries, as well as through on-line databases (the American Chemical Society, Washington, D.C., may be contacted for more details). Chemicals that are known but not commercially available in catalogs may be prepared by custom chemical synthesis houses, where many of the standard chemical supply houses (e.g., those listed above) provide custom synthesis services. A reference for the preparation and selection of pharmaceutical salts of the present disclosure is P. H. Stahl & C. G. Wermuth "Handbook of Pharmaceutical Salts," Verlag Helvetica Chimica Acta, Zurich, 2002.

Preparation of the PPQ Compounds

The following Reaction Schemes illustrate methods to make compounds of this disclosure, i.e., compounds of structures (I), (IA) and (IB)

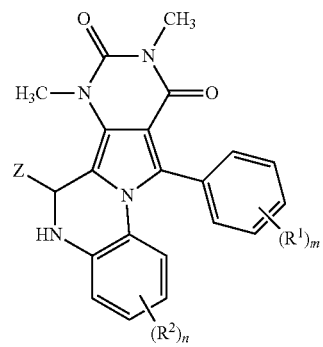

where $R^1$, $R^2$, $R^3$, $R^{1a}$, $R^{1b}$, $R^{1c}$, $R^{2a}$, $R^{2b}$, $R^4$, $R^{4b}$, $R^{4c}$, $R^{4d}$ and Z are described above in the Brief Summary, as an isolated enantiomer or a racemic mixture thereof, or a pharmaceutically acceptable salt thereof. It is understood that in the following Reaction Schemes, combinations of substituents and/or variables of the depicted structures are permissible only if such contributions result in stable compounds.

Reacton Scheme I

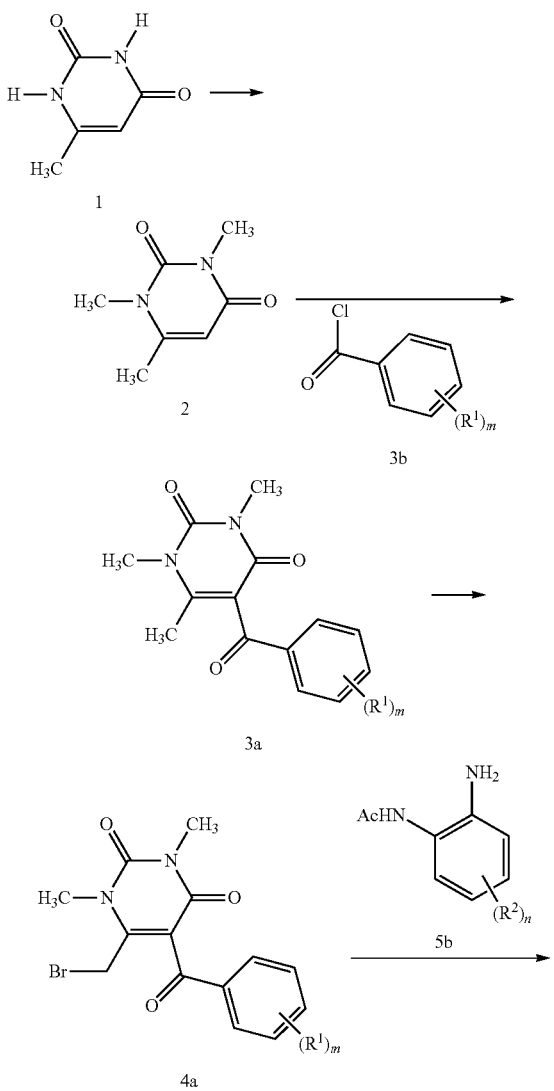

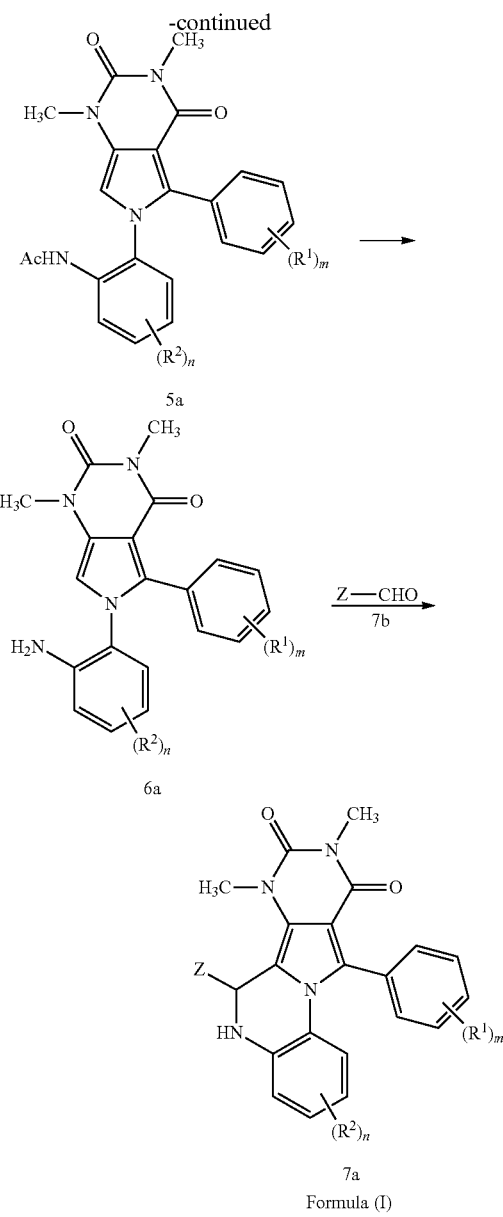

Formula (I)

Generally speaking, commercially available 6-methyluracil (1) can be first methylated to provide 1,3,6-trimethyluracil (2). Suitable methylating agents include dimethylsulfate, iodomethane, etc. Thereafter, 1,3,6-trimethyluracil (2) is further acylated to provide 3a via, e.g., a Friedel-Crafts mechanism, in the presence of an appropriately substituted benzoyl chloride (3b) and a Lewis acid catalyst (e.g., ZnCl). Compound (3a) can then be brominated to provide compound (4a). Reaction of compound (4a) and an appropriately substituted N-(2-aminophenyl)acetamide (5b) provides a ring-condensed product (5a). Following deprotection of the amino group of (5a) through conventional methods (e.g., hydrolysis), a deprotected compound (6a) can be combined with Z—CHO (7b) to produce a ring-condensed product (7a), i.e., Structure (I).

Methods of Using and Characterizing PPQ Compounds and Compositions Comprising PPQ Compounds As described in greater detail herein, pharmaceutical compositions are provided herein, wherein the pharmaceutical composition comprises a pharmaceutically suitable excipient (i.e., a pharmaceutically acceptable excipient or a physiologically suitable or acceptable excipient) and at least one of the PPQ compounds of any one of the structures, substructures, and specific structures described herein, including a compound of structure I, substructures (IA), (IB) and specific structures. The PPQ compounds of structure I, substructures (IA), (IB) and specific structures described herein that are capable of inhibiting CFTR activity (i.e., inhibiting, reducing, decreasing, blocking transport of chloride ion in the CFTR channel or pore in a statistically, clinically and/or biologically significant manner) in a cell may be used for treating diseases, disorders, and conditions that are treatable by inhibiting CFTR activity and include diseases, disorder, and conditions that result from or are related to aberrantly increased CFTR activity. Accordingly, methods of inhibiting ion transport by CFTR are provided herein.

Also as described herein, the PPQ compounds of structure I (and substructures thereof) that are CFTR inhibitors are useful in the treatment of a CFTR-mediated or -associated condition, i.e., any condition, disorder, or disease, that results from activity of CFTR, such as CFTR-mediated ion transport. The condition, disorder, or disease may result from aberrantly increased CFTR activity, particularly aberrantly increased CFTR-mediated ion transport. These conditions, disorders, and diseases, are amenable to treatment by inhibition of CFTR activity, e.g., inhibition of CFTR-mediated ion, such as chloride ion, transport.

Accordingly, methods are provided for treating a disease, disorder, or condition that is treatable by inhibiting CFTR-mediated ion transport. In certain embodiments, methods are provided for inhibiting cyst formation and/or cyst enlargement, particularly kidney cyst formation or enlargement. These methods are described in greater detail below and herein.

The PPQ compounds of structure I, substructures (IA), (IB) and specific structures as described herein are capable of blocking or impeding the CFTR pore or channel and inhibiting ion transport (e.g., inhibiting chloride ion (Cl⁻) transport (also referred to as inhibiting chloride ion conductance)) by CFTR located in the outer cell membrane of a cell. Provided herein are methods of inhibiting ion transport by CFTR, which methods comprise contacting a cell that has CFTR located in its outer membrane with any one or more of the PPQ compounds described herein, thus permitting CFTR and the compound or compounds to interact. Interaction of a PPQ compound described herein results in binding to CFTR, thereby inhibiting chloride ion transport.

In one embodiment, a method is provided for inhibiting (i.e., preventing, retarding, slowing) cyst formation and/or for inhibiting (i.e., preventing, retarding, slowing) or reducing cyst enlargement, or reducing the size and/or volume of one or more cysts, which method comprises contacting (a) a cell that comprises CFTR and (b) at least one compound of structure I or of any substructures (IA), (IB) and specific structures as described herein, under conditions and for a time sufficient for CFTR and the compound to interact, wherein the compound inhibits ion (e.g., chloride ion) transport by CFTR, (i.e., the PPQ compound inhibits CFTR-mediated ion transport in a statistically significant, clinically significant, and/or biologically significant manner). In particular embodiments, the cyst formation or cyst enlargement that is inhibited is kidney cyst formation or kidney cyst enlargement (i.e., cyst formation or cyst enlargement in at least one kidney is inhibited).

Inhibiting kidney cyst formation and/or cyst enlargement by the PPQ compounds described herein is useful for treating a patient who has been diagnosed with or who is at risk of developing polycystic kidney disease. Accordingly, methods are provided herein for treating polycystic kidney disease, which methods comprise administering to a subject in need thereof (a) a pharmaceutically suitable excipient and (b) at least one of the compounds of structure I, substructures (IA), (IB) and specific structures as described herein (i.e., a pharmaceutical composition as described herein). In a specific embodiment, polycystic kidney disease is autosomal dominant polycystic kidney disease. In another specific embodiment, polycystic kidney disease is autosomal recessive polycystic kidney disease.

In another embodiment, a method for treating a disease, disorder, or condition that is treatable by inhibiting CFTR-mediated ion transport includes a disease, disorder, or condition that is associated with aberrantly increased CFTR-mediated ion transport. Accordingly, in a specific embodiment, a method is provided for treating a disease, condition, or disorder associated with aberrantly increased ion transport by cystic fibrosis transmembrane conductance regulator (CFTR), wherein the method comprises administering to a subject in need thereof a pharmaceutically suitable excipient and at least one of the compounds of structure I, substructures (IA), (IB) (i.e., a pharmaceutical composition as described herein), wherein ion transport mediated by CFTR is inhibited. In a specific embodiment, the disease, condition, or disorder is aberrantly increased intestinal fluid secretion, which may be acute aberrantly increased intestinal fluid secretion.

In another embodiment, the PPQ compounds of structure I (and substructures thereof) are used in the treatment of conditions associated with aberrantly increased intestinal fluid secretion, particularly acute aberrantly increased intestinal fluid secretion, including secretory diarrhea. Diarrhea amenable to treatment using any one of the PPQ compounds described herein can result from exposure to a variety of agents or pathogens, including those that cause an enteropathogenic infection. In a more specific embodiment, secretory diarrhea is caused by an enteric pathogen. Exemplary enteric pathogens include without limitation, *Vibrio cholerae*, *Escherichia coli*, (particularly enterotoxigenic *E. coli* (ETEC)), *Shigella, Salmonella, Campylobacter* (Including *Campylobacter jejuni*), *Clostridium difficile*, parasites (e.g., *Giardia* (e.g., *Giardia lamblia*), *Entamoeba histolytica, Cryptosporidium, Cyclospora*), or diarrheal viruses (e.g., rotavirus). Secretory diarrhea resulting from an increased intestinal fluid secretion mediated by CFTR may also be a disorder or sequelae associated with food poisoning, or exposure to a toxin including but not limited to a bacterial enterotoxin such as cholera toxin (*V. cholera*), a *E. coli* toxin, a *Salmonella* toxin, a *Campylobacter* toxin, or a *Shigella* toxin, or any other bacterial toxin that causes aberrantly increased intestinal fluid secretion.

Other secretory diarrheas that may be treated by administering any one or more of the PPQ compounds of structure I (and substructures thereof) described herein include diarrhea associated with or that is a sequelae of AIDS, diarrhea that is a condition related to the effects of anti-AIDS medications such as protease inhibitors, diarrhea that is a condition of or is related to administration of chemotherapeutic compounds, inflammatory gastrointestinal disorders, such as ulcerative colitis, inflammatory bowel disease (IBD), Crohn's disease, diverticulosis, and the like. Intestinal inflammation modulates the expression of three major mediators of intestinal salt transport and may contribute to diarrhea in ulcerative colitis both by increasing transepithelial Cl⁻ secretion and by inhibiting the epithelial NaCl absorption (see, e.g., Lohi et al., *Am. J. Physiol. Gastrointest. Liver Physiol.* 283:G567-75 (2002)).

Thus, one or more of the PPQ compounds of structure I and substructures thereof (e.g., (IA) and (IB)), and specific structures as described herein may be administered in an amount effective to inhibit CFTR ion transport and, thus, decrease intestinal fluid secretion.

As understood by a person skilled in the medical art, the terms, "treat" and "treatment," refer to medical management of a disease, disorder, or condition of a subject (i.e., patient) (see, e.g., Stedman's Medical Dictionary). In general, an appropriate dose and treatment regimen provide the PPQ compound in an amount sufficient to provide therapeutic and/or prophylactic benefit. Therapeutic and/or prophylactic benefit includes, for example, an improved clinical outcome, both therapeutic treatment and prophylactic or preventative measures, wherein the object is to prevent or slow or retard (lessen) an undesired physiological change or disorder, or to prevent or slow or retard (lessen) the expansion or severity of such disorder. As discussed herein, beneficial or desired clinical results from treating a subject include, but are not limited to, abatement, lessening, or alleviation of symptoms that result from or are associated the disease, condition, or disorder to be treated; decreased occurrence of symptoms; improved quality of life; longer disease-free status (i.e., decreasing the likelihood or the propensity that a subject will present symptoms on the basis of which a diagnosis of a disease is made); diminishment of extent of disease; stabilized (i.e., not worsening) state of disease; delay or slowing of disease progression; amelioration or palliation of the disease state; and remission (whether partial or total), whether detectable or undetectable; and/or overall survival. "Treatment" can also mean prolonging survival when compared to expected survival if a subject were not receiving treatment. Subjects in need of treatment include those who already have the condition or disorder as well as subjects prone to have or at risk of developing the disease, condition, or disorder, and those in which the disease, condition, or disorder is to be prevented (i.e., decreasing the likelihood of occurrence of the disease, disorder, or condition).

Other embodiments provided herein include use of at least one of the PPQ compounds of structure I, substructures (IA), (IB) and specific structures as described herein for treating any one of the diseases or disorders described herein (e.g., polycystic kidney disease, aberrantly increased intestinal fluid secretion, secretory diarrhea) that is treatable by inhibiting ion transport (e.g., chloride ion transport) by CFTR. In one embodiment, a use is provided for the preparation of a medicament for treating any one of the diseases, conditions or disorders described herein (e.g., polycystic kidney disease, aberrantly increased intestinal fluid secretion, secretory diarrhea) that is treatable by inhibiting ion transport (e.g., chloride ion transport) by CFTR.

In other embodiments, methods are provided for treating a disease, disorder, or condition described herein (including but not limited to PCKD, secretory diarrhea or other condition associated with aberrantly increased intestinal fluid secretion). Such methods comprise administering a pharmaceutical composition that comprises at least one PPQ compound and a pharmaceutically suitable (i.e., pharmaceutically acceptable, or physiologically suitable or acceptable) excipient in combination, either in the same composition or in a separate (or second) composition, at least one thiazolidinone compound and/or at least one glycine hydrazide compound that inhibit CFTR-mediated ion transport (see, e.g., U.S. Pat. Nos. 7,235,573; 7,414,037; U.S. Patent Application Publication No. 2008-0064666; International Patent Application Publication No. WO 2008/079897; U.S. patent application Ser. No. 12/418,147; International Patent Application No.

PCT/US2009/038292, which are hereby incorporated by references in their entireties) for treating any one of the diseases or disorders described herein that is treatable by inhibiting ion transport (e.g., chloride ion transport) by CFTR. When a first composition comprising at least one PPQ compound and a second composition comprising at least one thiazolidinone compound and/or at least one glycine hydrazide compound is administered to a subject in need thereof, the first composition may be administered prior to, concurrently with, or subsequent to administration of the second composition.

In particular embodiments of the methods described herein, the subject is a human or non-human animal. A subject in need of the treatments described herein may exhibit symptoms or sequelae of a disease, disorder, or condition described herein or may be at risk of developing the disease, disorder, or condition. Non-human animals that may be treated include mammals, for example, non-human primates (e.g., monkey, chimpanzee, gorilla, and the like), rodents (e.g., rats, mice, gerbils, hamsters, ferrets, rabbits), lagomorphs, swine (e.g., pig, miniature pig), equine, canine, feline, bovine, and other domestic, farm, and zoo animals.

In another embodiment, a method is provided for inhibiting ion transport by a cystic fibrosis transmembrane conductance regulator (CFTR) comprising contacting (a) a cell that comprises CFTR and (b) at least one of the compounds of structure I, substructures (IA), (IB) and specific structures described herein, under conditions and for a time sufficient that permit CFTR and the compound to interact, thereby inhibiting ion transport (e.g., chloride ion transport) by CFTR, that is, inhibiting CFTR-mediated ion transport.

In another embodiment, a method is provided for treating secretory diarrhea comprising administering to a subject in need thereof a pharmaceutically acceptable excipient and at least one of the compounds of structure I, substructures (IA), (IB), and specific structures described herein (i.e., a pharmaceutical composition as described herein). In a particular embodiment, the subject is a human or non-human animal.

The pharmaceutical compositions and methods of using the PPQ compounds and compositions comprising these compounds are described in greater detail herein.

Methods for Characterizing and Using the PPQ Compounds

Also provided herein are methods that are useful, for example, for characterizing the potency of PPQ compounds (and derivatives and analogs thereof) to inhibit CFTR-mediated ion transport (particularly CFTR-mediated chloride ion transport); for monitoring the level (i.e., for example, concentration level, mass level, or $IC_{50}$ level) of a PPQ compound that has been administered to a subject; and examining disease pathogenesis in cystic fibrosis by blocking or inhibiting CFTR function as models for cystic fibrosis disease, such as in ex vivo tissues (e.g., human tissues) and in animals.

In certain embodiments, these methods may be performed in vitro, such as with using a biological sample as described herein that comprises, for example, cells obtained from a tissue, body fluid, or culture-adapted cell line, or other biological source as described in detail herein below. The step of contacting refers to combining, mixing, or in some manner familiar to persons skilled in the art, which permits the compound and the cell to interact such that any effect of the compound on CFTR activity (e.g., the capability of a PPQ compound to inhibit CFTR ion transport or the level to which the compound inhibits CFTR ion transport) can be measured according to methods described herein and routinely practiced in the art. Methods described herein for inhibiting ion transport by CFTR are understood to be performed under conditions and for a time sufficient that permit the CFTR and the compound to interact. Additional PPQ compounds may be identified and/or characterized by such a method of inhibiting ion transport by CFTR, performed with isolated cells in vitro. Conditions for a particular assay include temperature, buffers (including salts, cations, media), and other components that maintain the integrity of the cell and the compound, which a person skilled in the art will be familiar and/or which can be readily determined. A person skilled in the art also readily appreciates that appropriate controls can be designed and included when performing the in vitro methods and in vivo methods described herein.

In secretory epithelia, fluid secretion occurs by primary chloride exit across the cell apical membrane, which secondarily drives transepithelial sodium and water secretion (see, e.g., Barrett et al., *Annu. Rev. Physiol.* 62:535-72 (2000)). In renal cells, lumenal fluid accumulation causes progressive cyst expansion directly by net water influx into the cyst lumen, and indirectly by stretching cyst wall epithelial cells to promote their division and thinning (Ye et al., *N. Engl. J. Med.* 329:310-13 (1993); Sullivan et al., *Physiol. Rev.* 78:1165-91 (1998); Tanner et al., *J. Am. Soc. Nephrol.* 6:1230-41 (1995)). Without wishing to be bound by any particular theory, CFTR inhibition interferes with fluid secretion at the apical chloride exit step.

Methods for characterizing a PPQ compound, for determining an effective concentration to achieve a therapeutic benefit, for monitoring the level of a PPQ compound in a biological sample, and for other purposes as described herein and apparent to a person skilled in the art, may be performed using techniques and procedures described herein and routinely practiced by a person skilled in the art. Exemplary methods include, but are not limited to, fluorescence cell-based assays of CFTR inhibition (see, e.g., Galietta et al., *J. Physiol.* 281:C1734-C1742 (2001)), short circuit apical chloride ion current measurements and patch-clamp analysis (see, e.g., Muanprasat et al., *J. Gen. Physiol.* 124:125-37 (2004); Ma et al., *J. Clin. Invest.* 110:1651-58 (2002); see also, e.g., Carmeliet, *Verh. K. Acad. Geneeskd. Belg.* 55:5-26 (1993); Hamill et al., *Pflugers Arch.* 391:85-100 (1981)).

Methods that may be used to characterize a PPQ compound, including those described herein, and to determine effectiveness of the compound for reducing, inhibiting, or preventing cyst enlargement and/or preventing or inhibiting cyst formation, and which compound is therefore useful for treating a subject who has or who is at risk of developing PKD, include methods described in the art and herein. The PPQ compounds may be analyzed in models using embryonic or neonatal kidney organ cultures, for example (see, e.g., Yang et al., *J. Am. Soc. Nephrol.* 19:1300-1310 (2008); Magenheimer et al., *J. Am. Soc. Nephrol.* 17:3424-37 (2006)). Without wishing to be bound by any particular theory, certain scientific observations support use of CFTR inhibitors to slow cyst growth in autosomal dominant PKD (ADPKD): (a) CFTR is expressed strongly in epithelial cells lining cysts in ADPKD; (b) cystic fibrosis (CFTR-deficient) mice are resistant to cyst formation; (c) CFTR inhibitors block cyst formation in cell/organ culture and in vivo models; and (d) in some families affected with ADPKD and cystic fibrosis, individuals with both ADPKD and CF have less severe renal disease than those with ADPKD only (see, e.g., O'Sullivan et al., *Am. J. Kidney Dis.* 1998, 32:976-983; Cotton et al., *Am. J. Kidney Dis.* 1998, 32:1081-1083). Intact kidney models to study cystogenesis are useful for recapitulating native kidney anatomy and cellular phenotype (see, e.g., Magenheimer et al., *J. Am. Soc. Nephrol.* 2006, 17:3424-3437).

An additional example of a cell culture model for determining whether a compound inhibits cyst formation or enlargement includes an MDCK cell (Madin-Darby Canine Kidney Epithelial Cell) model of PKD (Li et al., *Kidney Int* 66:1926-1938 (2004); see also, e.g., Neufeld et al., *Kidney Int.* 41:1222-36 (1992); Mangoo-Karim et al., *Proc. Natl. Acad. Sci. USA* 86:6007-6011 (1989); Mangoo-Karim et al., *FASEB J.* 3:2629-32 (1989); Grantham et al., *Trans. Assoc. Am. Physic.* 102:158-62 (1989); Mohamed et al., *Biochem J*322: 259-265 (1997)). See also, e.g., Murcia et al., *Kidney Int.* 55:1187-97 (1999); Igarishi et al., *J. Am. Soc. Nephrol.* 13:2384-88 (2002)). Accordingly, provided herein are methods for identifying and/or characterizing PPQ compounds of structure I (and substructures thereof) by determining the capability of the compound to inhibit cyst enlargement or prevent or inhibit cyst formation in an in vitro cell culture model.

The MDCK cell line may also be used in methods and techniques for determining that a compound lacks cytotoxicity, for example, by evaluating cell viability (e.g., by any one of numerous cell staining methods and microscopy methods routinely practiced in the art), cell proliferation (e.g., by determining the level of incorporation of nucleotide analogs and other methods for measuring division of cells), and/or apoptosis by using any one of a number of techniques and methods known in the art and described herein. Other methods for determining or quantifying the capability of a compound described herein to inhibit or reverse cyst enlargement or expansion and/or to inhibit or prevent cyst formation and/or to reduce the number of cysts formed include an embryonic kidney organ culture model, which is practiced in the art and described herein (see, e.g., Magenheimer et al., *J. Am. Soc. Nephrol.* 17: 3424-37 (2006); Steenhard et al., *J. Am. Soc. Nephrol.* 16:1623-1631 (2005); Yang et al., *J. Am. Soc. Nephrol.* 19:1300-1310 (2008)). In such an embryonic kidney culture model, organotypic growth and differentiation of renal tissue can be monitored in defined media in the absence of any effect or influence by circulating hormones and glomerular filtration (Magenheimer et al., supra; Gupta et al., *Kidney Int.* 63:365-376 (2003)). In metanephric organ culture, the early mouse kidney tubule has an intrinsic capacity to secrete fluid by a CFTR-dependent mechanism in response to cAMP (Magenheimer et al., supra).

Persons skilled in the art may also use animal models to characterize a PPQ compound, including those described herein, and to determine effectiveness of the compound for reducing, inhibiting, reversing, or preventing cyst enlargement and/or preventing or inhibiting cyst formation thereby reducing the number of cysts formed, and to determine the usefulness of such compounds for treating a subject who has or who is at risk of developing PKD. By way of example, Pkd1$^{flox}$ mice and Ksp-Cre transgenic mice in a C57BL/6 background may be generated as described and practiced in the art (see, e.g., Shibazaki et al., *J. Am. Soc. Nephrol.* 13:10-11 (2004) (abstract); Shao et al., *J. Am. Soc. Nephrol.* 13:1837-46 (2002)). Ksp-Cre mice express Cre recombinase under the control of the Ksp-cadherin promoter (see, e.g., Shao et al., supra). Pkd1$^{flox/-}$; Ksp-Cre mice may be generated by cross-breeding Pkd1$^{flox/flox}$ mice with Pkd1$^{+/-}$:Ksp-Cre mice. The effect of a test compound may be determined by quantifying cyst size and growth in metanephroi and kidney sections, histological analyses of tissues and cells, and delay or prevention of renal failure and death (see, e.g., Shibazaki et al., supra).

The PPQ compounds may also be analyzed in animal models that are art-accepted animal models for increased intestinal fluid secretion. By way of example, a closed intestinal loop model of cholera, suckling mouse model of cholera, and in vivo imaging of gastrointestinal transit may be used for characterizing the PPQ compounds described herein (see, e.g., Takeda et al., *Infect. Immun.* 19:752-54 (1978); see also, e.g., Spira et al., *Infect. Immun.* 32:739-747 (1981)).

Methods of inhibiting CFTR-mediated ion transport include in vitro methods that comprise contacting a cell with any one or more of the PPQ compounds of structure I (and substructures thereof) as described herein, under conditions and for a time sufficient for CFTR present in the outer membrane of the cell and the compound to interact. Cells (or cell lines) that may be used in such methods are cells that expresses CFTR and have channels or pores formed by CFTR in the cell membrane. Exemplary cells and cell lines include without limitation a Fischer rat thyroid (FRT) cell (including a FRT cell that co-expresses human or other animal wildtype CFTR and the halide indicator YFP-H148Q or other comparable yellow fluorescent protein); a cultured human bronchial epithelial cell; and a gastrointestinal cell (such as T84 human intestinal epithelial cells)) that comprises CFTR in the outer membrane of the cell. Such methods are useful for identifying analogs of the PPQ compounds (i.e., species of structure I including species of substructures (IA) and (IB)) described herein and for characterizing the PPQ compounds described herein.

In certain embodiments, the cell is contacted in an in vitro assay, and the cell may be obtained from a subject or from a biological sample. A biological sample may be a blood sample (from which serum or plasma may be prepared and cells isolated), biopsy specimen, body fluids (e.g., lung lavage, ascites, mucosal washings, synovial fluid), bone marrow, lymph nodes, tissue explant (e.g., kidney cells), organ culture (e.g., kidney), or any other tissue or cell preparation from a subject or a biological source. A sample may further refer to a tissue or cell preparation in which the morphological integrity or physical state has been disrupted, for example, by dissection, dissociation, solubilization, fractionation, homogenization, biochemical or chemical extraction, pulverization, lyophilization, sonication, or any other means for processing a sample derived from a subject or biological source. The subject or biological source may be a human or non-human animal, a primary cell culture (e.g., immune cells, virus infected cells), or culture adapted cell line, including but not limited to, genetically engineered cell lines that may contain chromosomally integrated or episomal recombinant nucleic acid sequences, immortalized or immortalizable cell lines, somatic cell hybrid cell lines, differentiated or differentiatable cell lines, transformed cell lines, and the like.

Pharmaceutical Compositions and Methods of Using Pharmaceutical Compositions

Also provided herein are pharmaceutical compositions comprising any one or more of the PPQ compounds of structure I (and substructures thereof). The compounds described herein may be formulated in a pharmaceutical composition for use in treatment or preventive (or prophylactic) treatment (e.g., reducing the likelihood of occurrence of cyst formation), of polycystic kidney disease (PKD), which includes autosomal dominant PKD (ADPKD) and autosomal recessive PKD (ARPKD). In other embodiments, a pharmaceutical composition comprising at least one PPQ compound may be formulated for use in treatment or preventive treatment (i.e., for reducing the likelihood of occurrence) of a disease, condition, or disorder manifested by increased intestinal fluid secretion, such as secretory diarrhea.

In pharmaceutical dosage forms, any one or more of the PPQ compounds of structure I, substructures (IA), (IB) and specific structures described herein may be administered in the form of a pharmaceutically acceptable derivative, such as a salt, or they may also be used alone or in appropriate association, as well as in combination, with other pharmaceutically active compounds. The methods and excipients described herein are merely exemplary and are in no way limiting.

Optimal doses may generally be determined using experimental models and/or clinical trials. The optimal dose may depend upon the body mass, weight, or blood volume of the subject. In general, the amount of a PPQ compound of structure I (and substructures thereof) described herein, that is present in a dose, ranges from about 0.01 µg to about 1000 µg per kg weight of the host. The use of the minimum dose that is sufficient to provide effective therapy is usually preferred. Subjects may generally be monitored for therapeutic effectiveness using assays suitable for the condition being treated or prevented, which assays will be familiar to those having ordinary skill in the art and are described herein. The level of a compound that is administered to a subject may be monitored by determining the level of the compound in a biological fluid, for example, in the blood, blood fraction (e.g., serum), and/or in the urine, and/or other biological sample from the subject. Any method practiced in the art to detect the compound may be used to measure the level of compound during the course of a therapeutic regimen.

The dose of a composition comprising at least one of the PPQ compounds described herein for treating PCKD may depend upon the subject's condition, that is, stage of the disease, renal function, severity of symptoms caused by enlarged cysts, general health status, as well as age, gender, and weight, and other factors apparent to a person skilled in the medical art. Similarly, the dose of the PPQ compound for treating a disease or disorder associated with aberrantly increased CFTR function, including but not limited to intestinal fluid secretion, secretory diarrhea, such as a toxin-induced diarrhea, or secretory diarrhea associated with or a sequelae of an enteropathogenic infection, Traveler's diarrhea, ulcerative colitis, irritable bowel syndrome (IBS), AIDS, chemotherapy and other diseases or conditions described herein may be determined according to parameters understood by a person skilled in the medical art. Accordingly, the appropriate dose may depend upon the subject's condition, that is, stage of the disease, general health status, as well as age, gender, and weight, and other factors considered by a person skilled in the medical art.

Pharmaceutical compositions may be administered in a manner appropriate to the disease or disorder to be treated as determined by persons skilled in the medical arts. An appropriate dose and a suitable duration and frequency of administration will be determined by such factors as the condition of the patient, the type and severity of the patient's disease, the particular form of the active ingredient, and the method of administration. In general, an appropriate dose (or effective dose) and treatment regimen provides the composition(s) comprising at least one PPQ compound in an amount sufficient to provide therapeutic and/or prophylactic benefit (for example, an improved clinical outcome, such as more frequent complete or partial remissions, or longer disease-free and/or overall survival, or a lessening of symptom severity or other benefit as described in detail above). When a subject is treated for aberrantly increased intestinal fluid secretion, clinical assessment of the level of dehydration and/or electrolyte imbalance may be performed to determine the level of effectiveness of a compound and whether dose or other administration parameters (such as frequency of administration or route of administration) should be adjusted.

Polycystic kidney disease (PKD) (or PCKD) and polycystic renal disease are used interchangeably, and refer to a group of disorders characterized by a large number of cysts distributed throughout enlarged kidneys. The resultant cyst development leads to impairment of kidney function and can eventually cause kidney failure. PDK includes autosomal dominant polycystic kidney disease (ADPKD) and recessive autosomal recessive polycystic kidney disease (ADPKD), in all stages of development, regardless of the underlying etiology or cause. Effectiveness of a treatment for PKD may be monitored by one or more of several methods practiced in the medical art including, for example, by monitoring renal function by standard measurements, and by radiologic investigations that are performed with ultrasounds, computerized tomography (CT), or magnetic resonance imaging, which are useful for evaluating renal cyst morphology and volume and estimating the amount of residual renal parenchyma.

To evaluate and to monitor the effectiveness of any one of the PPQ compounds described herein to treat PKD or a related disease or condition, one or more of several clinical assay methods may be performed that are familiar to a person skilled in the clinical art. For example, a clinical method called a urea clearance test may be performed. A blood sample is obtained from a subject to whom the compound is being administered so that the amount of urea in the bloodstream can be determined. In addition, a first urine sample is collected from the subject and at least one hour later, a second urine sample is collected. The amount of urea quantified in the urine indicates the amount of urea that is filtered, or cleared by the kidneys into the urine. Another clinical assay method measures urine osmolality (i.e., the amount of dissolved solute particles in the urine). Inability of the kidneys to concentrate the urine in response to restricted fluid intake, or to dilute the urine in response to increased fluid intake during osmolality testing may indicate decreased kidney function.

Urea is a by-product of protein metabolism and is formed in the liver. Urea is then filtered from the blood and excreted in the urine by the kidneys. The BUN (blood urea nitrogen) test measures the amount of nitrogen contained in the urea. High BUN levels may indicate kidney dysfunction, but because blood urea nitrogen is also affected by protein intake and liver function, the test is usually performed in conjunction with determination of blood creatinine, which is considered a more specific indicator of kidney function. Low clearance values for creatinine and urea indicate diminished ability of the kidneys to filter these waste products from the blood and excrete them in the urine. As clearance levels decrease, blood levels of creatinine and urea nitrogen increase. An abnormally elevated blood creatinine, a more specific and sensitive indicator of kidney disease than the BUN, is diagnostic of impaired kidney function.

The pharmaceutical compositions described herein that comprise at least one PPQ compound may be administered to a subject in need by any one of several routes that effectively deliver an effective amount of the compound. Such administrative routes include, for example, oral, parenteral, enteral, rectal, intranasal, buccal, sublingual, intramuscular, and transdermal. By way of example, at least one or more of the compounds may be administered to a mucosal surface of the gastrointestinal tract (e.g., by an enteral route, which includes administration directly to the tract via a tube inserted into the nose, stomach, or small intestine) or to a mucosal surface of the oral or nasal cavities, or (e.g., intranasal, buccal, sublingual, and the like). These administrative methods and additional methods are discussed in greater detail herein.

A pharmaceutical composition may be a sterile aqueous or non-aqueous solution, suspension or emulsion, which additionally comprises a physiologically acceptable excipient (pharmaceutically acceptable or suitable excipient or carrier) (i.e., a non-toxic material that does not interfere with the activity of the active ingredient). Such compositions may be in the form of a solid, liquid, or gas (aerosol). Alternatively, compositions described herein may be formulated as a lyophilizate, or compounds may be encapsulated within liposomes using technology known in the art. Pharmaceutical compositions may also contain other components, which may be biologically active or inactive. Such components include, but are not limited to, buffers (e.g., neutral buffered saline or phosphate buffered saline), carbohydrates (e.g., glucose, mannose, sucrose or dextrans), mannitol, proteins, polypeptides or amino acids such as glycine, antioxidants, chelating agents such as EDTA or glutathione, stabilizers, dyes, flavoring agents, and suspending agents and/or preservatives.

Any suitable excipient or carrier known to those of ordinary skill in the art for use in pharmaceutical compositions may be employed in the compositions described herein. Excipients for therapeutic use are well known, and are described, for example, in *Remington: The Science and Practice of Pharmacy* (Gennaro, 21$^{st}$ Ed. Mack Pub. Co., Easton, Pa. (2005)). In general, the type of excipient is selected based on the mode of administration. Pharmaceutical compositions may be formulated for any appropriate manner of administration, including, for example, topical, oral, nasal, intrathecal, rectal, vaginal, intraocular, subconjunctival, sublingual or parenteral administration, including subcutaneous, intravenous, intramuscular, intrasternal, intracavernous, intrameatal or intraurethral injection or infusion. For parenteral administration, the carrier preferably comprises water, saline, alcohol, a fat, a wax or a buffer. For oral administration, any of the above excipients or a solid excipient or carrier, such as mannitol, lactose, starch, magnesium stearate, sodium saccharine, talcum, cellulose, kaolin, glycerin, starch dextrins, sodium alginate, carboxymethylcellulose, ethyl cellulose, glucose, sucrose and/or magnesium carbonate, may be employed.

A pharmaceutical composition (e.g., for oral administration or delivery by injection) may be in the form of a liquid. A liquid pharmaceutical composition may include, for example, one or more of the following: a sterile diluent such as water for injection, saline solution, preferably physiological saline, Ringer's solution, isotonic sodium chloride, fixed oils that may serve as the solvent or suspending medium, polyethylene glycols, glycerin, propylene glycol or other solvents; antibacterial agents; antioxidants; chelating agents; buffers and agents for the adjustment of tonicity such as sodium chloride or dextrose. A parenteral preparation can be enclosed in ampoules, disposable syringes or multiple dose vials made of glass or plastic. The use of physiological saline is preferred, and an injectable pharmaceutical composition is preferably sterile.

A composition comprising any one of the compounds of structure (I) and substructures (IA) and (IB) described herein may be formulated for sustained or slow release. Such compositions may generally be prepared using well known technology and administered by, for example, oral, rectal or subcutaneous implantation, or by implantation at the desired target site. Sustained-release formulations may contain a compound dispersed in a carrier matrix and/or contained within a reservoir surrounded by a rate controlling membrane. Excipients for use within such formulations are biocompatible, and may also be biodegradable; preferably the formulation provides a relatively constant level of active component release. The amount of active compound contained within a sustained release formulation depends upon the site of implantation, the rate and expected duration of release, and the nature of the condition to be treated or prevented.

For oral formulations, a PPQ compound of structure (I) and substructures (IA) and (IB) can be used alone or in combination with appropriate additives to make tablets, powders, granules or capsules, for example, with conventional additives, such as lactose, mannitol, corn starch or potato starch; with binders, such as starch, gelatin, natural sugars such as glucose or beta-lactose, corn sweeteners, natural and synthetic gums such as acacia, tragacanth, or sodium alginate, carboxymethylcellulose, polyethylene glycol, waxes, crystalline cellulose, cellulose derivatives, and acacia; with disintegrators, such as corn starch, potato starch or sodium carboxymethylcellulose, methyl cellulose, agar, bentonite, or xanthan gum; with lubricants, such as talc, sodium oleate, magnesium stearate sodium stearate, sodium benzoate, sodium acetate, or sodium chloride; and if desired, with diluents, buffering agents, moistening agents, preservatives, coloring agents, and flavoring agents. The compounds may be formulated with a buffering agent to provide for protection of the compound from low pH of the gastric environment and/or an enteric coating. The PPQ compounds of structure I (and substructures thereof) may be formulated for oral delivery with a flavoring agent, e.g., in a liquid, solid or semi-solid formulation and/or with an enteric coating.

Oral formulations may be provided as gelatin capsules, which may contain the active compound along with powdered carriers, such as lactose, starch, cellulose derivatives, magnesium stearate, stearic acid, and the like. Similar carriers and diluents may be used to make compressed tablets. Tablets and capsules can be manufactured as sustained release products to provide for continuous release of active ingredients over a period of time. Compressed tablets can be sugar coated or film coated to mask any unpleasant taste and protect the tablet from the atmosphere, or enteric coated for selective disintegration in the gastrointestinal tract. Liquid dosage forms for oral administration may contain coloring and/or flavoring agents to increase acceptance of the compound by the subject.

The PPQ compounds of structure I (and substructures thereof) described herein can be made into suppositories by mixing with a variety of bases such as emulsifying bases or water-soluble bases. The compounds described herein can be administered rectally via a suppository. The suppository can include vehicles such as cocoa butter, carbowaxes and polyethylene glycols, which melt at body temperature, yet are solidified at room temperature.

The PPQ compounds of structure I (and substructures thereof) described herein may be used in aerosol formulation to be administered via inhalation. The compounds may be formulated into pressurized acceptable propellants such as dichlorodifluoromethane, propane, nitrogen and the like.

Any one or more of the PPQ compounds of structure I (and substructures thereof) described herein may be administered topically (e.g., by transdermal administration). Topical formulations may be in the form of a transdermal patch, ointment, paste, lotion, cream, gel, and the like. Topical formulations may include one or more of a penetrating agent, thickener, diluent, emulsifier, dispersing aid, or binder. When a PPQ compound is formulated for transdermal delivery, the compound may be formulated with or for use with a penetration enhancer. Penetration enhancers, which include chemical penetration enhancers and physical penetration enhancers, facilitate delivery of the compound through the skin, and may also be referred to as "permeation enhancers" interchangeably. Physical penetration enhancers include, for example, electrophoretic techniques such as iontophoresis, use of ultrasound (or "phonophoresis"), and the like. Chemical penetration enhancers are agents administered either prior to, with, or immediately following compound administration, which increase the permeability of the skin, particularly the stratum corneum, to provide for enhanced penetration of the drug through the skin. Additional chemical and physical penetration enhancers are described in, for example, Transdermal Delivery of Drugs, A. F. Kydonieus (ED) 1987 CRL Press; Percutaneous Penetration Enhancers, eds. Smith et al. (CRC Press, 1995); Lenneruas et al., *J. Pharm. Pharmacol.* 2002; 54(4):499-508; Karande et al., *Pharm. Res.* 2002; 19(5):655-60; Vaddi et al., *Int. J. Pharm.* 2002 July; 91(7):1639-51; Ventura et al., *J. Drug Target* 2001; 9(5):379-93; Shokri et al., *Int. J. Pharm.* 2001; 228(1-2):99-107; Suzuki et al., *Biol. Pharm. Bull.* 2001; 24(6):698-700; Alberti et al., *J. Control Release* 2001; 71(3):319-27; Goldstein et al., *Urology* 2001; 57(2):301-5; Kiijavainen et al., *Eur. J. Pharm. Sci.* 2000; 10(2):97-102; and Tenjarla et al., *Int. J. Pharm.* 1999; 192(2):147-58.

When a PPQ compound of structure I (and substructures thereof) is formulated with a chemical penetration enhancer, the penetration enhancer is selected for compatibility with the compound, and is present in an amount sufficient to facilitate delivery of the compound through skin of a subject, e.g., for delivery of the compound to the systemic circulation. The PPQ compounds of structure I (and substructures thereof) may be provided in a drug delivery patch, e.g., a transmucosal or transdermal patch, and can be formulated with a penetration enhancer. The patch generally includes a backing layer, which is impermeable to the compound and other formulation components, a matrix in contact with one side of the backing layer, which matrix provides for sustained release, which may be controlled release, of the compound, and an adhesive layer, which is on the same side of the backing layer as the matrix. The matrix can be selected as is suitable for the route of administration, and can be, for example, a polymeric or hydrogel matrix.

In one embodiment, the PPQ compounds of structure I (and substructures thereof) are delivered to the gastrointestinal tract of the subject to provide for decreased fluid secretion. Suitable formulations for this embodiment include any formulation that provides for delivery of the compound to the gastrointestinal surface, particularly an intestinal tract surface.

For use in the methods described herein, one or more of the PPQ compounds of structure I (and substructures thereof) described herein may be formulated with other pharmaceutically active agents or compounds, including other CFTR-inhibiting agents and compounds or agents and compounds that block intestinal chloride channels (e.g., a glycine hydrazide compound or thiazolidinone compound as discussed herein). Similarly, one or more of the PPQ compounds of structure I (and substructures thereof) described herein may be formulated with other pharmaceutically active agents or compounds, including other CFTR-inhibiting agents and compounds, or other agents and compounds that are administered to a subject for treating PKD.

Kits with unit doses of the PPQ compounds of structure I (and substructures thereof) described herein, usually in oral or injectable doses, are provided. Such kits may include a container containing the unit dose, an informational package insert describing the use and attendant benefits of the drugs in treating pathological condition of interest, and optionally an appliance or device for delivery of the composition.

Also provided herein are methods of manufacturing the pharmaceutical compositions described herein that comprise at least one of the PPQ compounds of structure I, substructures (IA), (IB) and specific structures as described herein. In one embodiment, the method of manufacture comprises synthesis of the compound. Synthesis of one of more of the compounds described herein may be performed according to methods described herein and practiced in the art. In another method of manufacture, the method comprises comprise formulating (i.e., combining, mixing) at least one of the compounds disclosed herein with a pharmaceutically suitable excipient. These methods are performed under conditions that permit formulation and/or maintenance of the desired state (i.e., liquid or solid, for example) of each of the compound and excipient. A method of manufacture may comprise one or more of the steps of synthesizing the at least one compound, formulating the compound with at least one pharmaceutically suitable excipient to form a pharmaceutical composition, and dispensing the formulated pharmaceutical composition in an appropriate vessel (i.e., a vessel appropriate for storage and/or distribution of the pharmaceutical composition).

Other embodiments and uses will be apparent to one skilled in the art in light of the present disclosures. The following examples are provided merely as illustrative of various embodiments and shall not be construed to limit the invention in any way.

EXAMPLES

Example 1

Synthesis of PPQ-102

Synthesis procedures (General)—$^1$H and $^{13}$C NMR spectra were obtained in deuterated dimethyl sulfoxide (DMSO-$d_6$) using a 400-MHz Varian Spectrometer referenced to DMSO. Mass spectrometry was performed using a Waters LC/MS system (Alliance HT 2790+ZQ, HPLC: Waters model 2690, Milford, Mass.). Flash chromatography was performed using EM silica gel (230-400 mesh), and thin-layer chromatography was performed using Merk silica gel 60 F254 plates (Darmstadt, Germany). Microwave reactions were performed in a Biotage Initiator™ (Biotage, Uppsala, Sweden) (0.5-2 mL vials) with target temperature reached within 30 s at ~55 watts. Melting points are uncorrected. Purity to >98% was confirmed by LCMS.

Figure 2A:
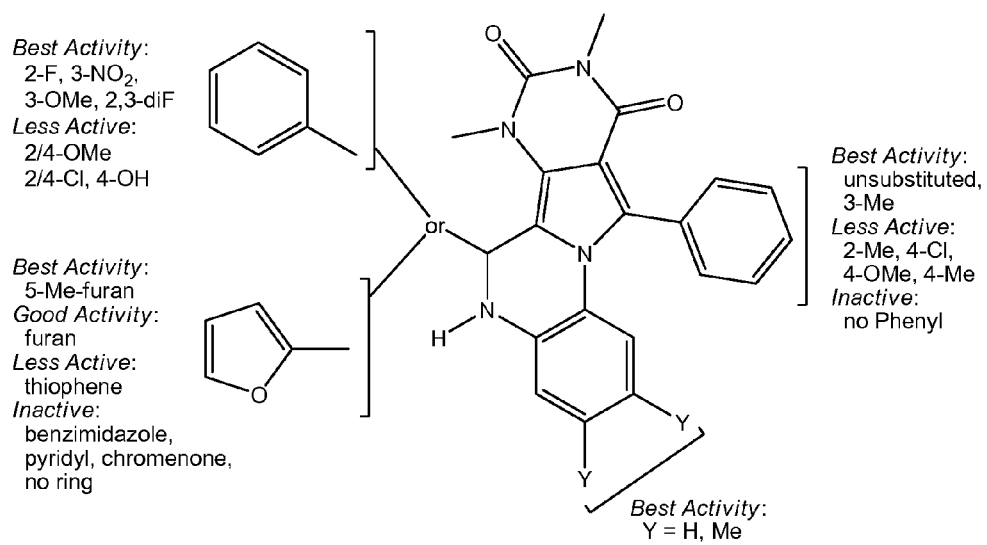
FIGS. 2A and 2B present a summary of structure-activity analysis and synthesis of PPQ-102, respectively.
Figure 2B:
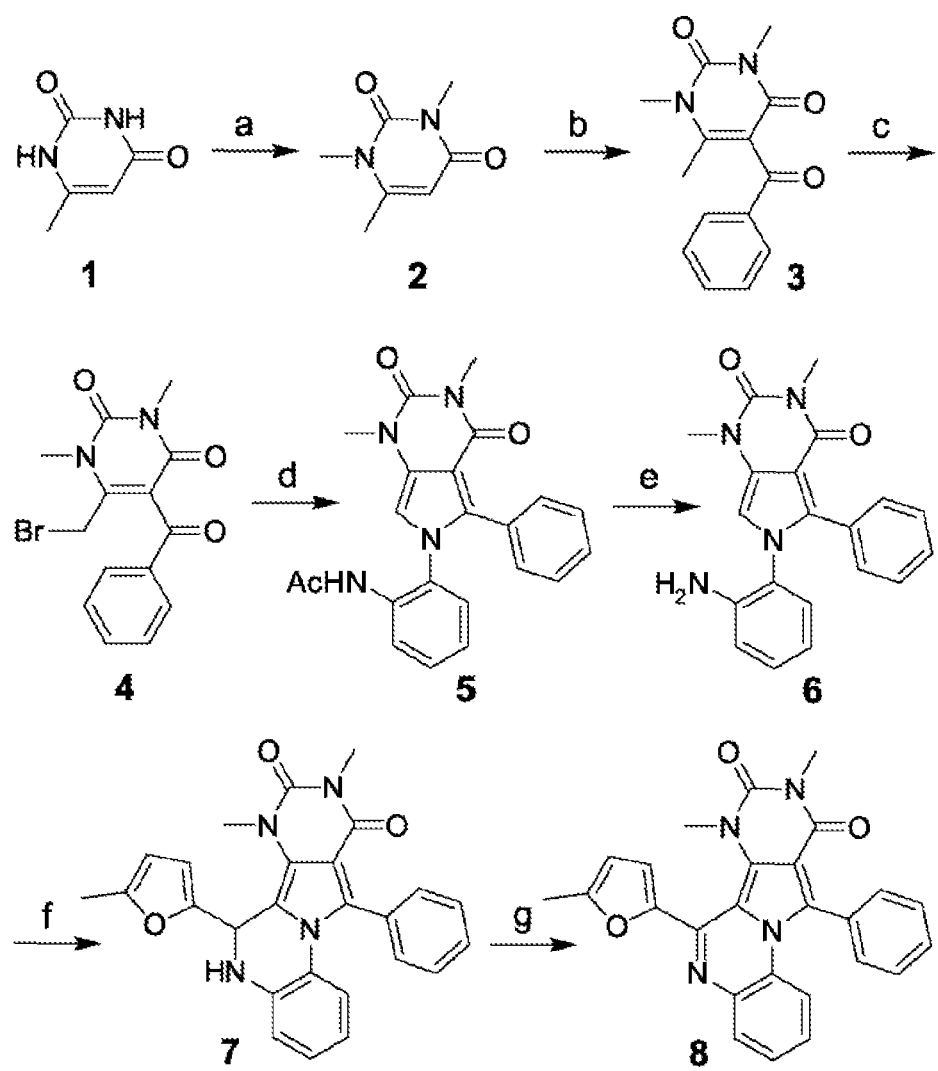

Synthesis of PPQ-102—Synthesis of PPQ-102 was achieved in six steps as illustrated in FIG. 2B. Commercially available 6-methyluracil 1 was methylated using dimethylsulfate to produce 1,3,6-trimethyluracil 2, which upon Friedel-Crafts acylation using zinc chloride as a catalyst yielded 5-benzoyl-1,3,6-trimethylpyrimidine-2,4(1H,3H)-dione 3 as a white powder. Bromination of 3 followed by reaction with N-(2-aminophenyl)acetamide generated amino-protected intermediate 5. The acetamido function of 5 was hydrolyzed and resultant intermediate 6 was cyclocondensed with 5-methylfurfural to yield yellowish-white racemic PPQ-102 7. Aromatic compound 8, which lacks a stereocenter, was prepared from 7 by oxidation with potassium permanganate.

Reagents and conditions for reactions shown in FIG. 2B: (a) $Me_2SO_4$, NaOH, 40° C., 4 h, 43%; (b) PhCOCl, $ZnCl_2$, toluene, reflux, 6 h, 28%; (c) $Br_2$, $CHCl_3$, rt, 2 h, 57%; (d) N-(2-aminophenyl)acetamide, microwave, 170° C., 1 h, 51%; (e) HCl, reflux, 6 h, 67%; (f) 5-Me-furan-2-carbaldehyde, 170° C., 10 min, 43%; (g) $KMnO_4$, $Me_2CO$, 1 h, 40%. Synthesis of PPQ-102 and intermediates is described in greater detail below.

1,3,6-Trimethyl-1H,3H-pyrimidine-2,4-dione (2). (See, e.g., Azas et al., *Farmaco.* 58:1263-1270 (2003)). Dimethylsulfate (106 g, 80 ml, 844 mmol) was added dropwise to a solution of 2,4-dihydroxy-6-methylpyrimidine (30 g, 238 mmol) in 280 mL of 4 N NaOH at 40° C. After stirring for 4 h at 40° C., the reaction mixture was neutralized with careful addition of acetic acid and extracted 3 times with 100 mL of ethyl acetate. Combined organics were dried over MgSO$_4$ and concentrated in vacuo to yield a white solid. Recrystallization from ethanol yielded 2 (15.8 g, 43%): mp 113-114° C.; $^1$H NMR (DMSO-d$_6$): δ 5.58 (s, 1H), 3.26 (s, 3H), 3.09 (s, 3H,), 2.19 (s, 3H,); MS (ES+) (m/z): [M+1]+ calculated for C$_7$H$_{11}$N$_2$O$_2$, 155.17. found 155.93. This compound matched the analytical data as reported (see, e.g., Azas et al., *Farmaco.* 58:1263-1270 (2003)).

5-Benzoyl-1,3,6-trimethylpyrimidine-2,4(1H,3H)-dione (3). A mixture of 1,3,6-trimethyl-compound 2 (12.3 g, 80 mmol), benzoyl chloride (11.5 g, 9.5 mL, 82 mmol) and anhydrous zinc chloride (10.8 g, 79 mmol) in toluene (100 mL) was heated to reflux for 6 h. The mixture was poured over ice (200 g), and the separated toluene layer was concentrated in vacuo. The crude residue was purified by flash chromatography to yield 3 (5.8 g, 28%): mp 132-134° C.; MS (ES+) (m/z): [M+1]+ calculated for C$_{14}$H$_{15}$N$_2$O$_3$, 259.28. found 259.09. This compound matched analytical data as reported (see, e.g., Tsupak et al., *Khimiya Geterotsiklicheskikh Soedinenii.* 7:1096-1102 (2003)).

5-Benzoyl-6-(bromomethyl)-1,3-dimethylpyrimidine-2,4 (1H,3H)-dione (4). (See, e.g., Tsupak et al., *Khimiya Geterotsiklicheskikh Soedinenii.* 7:1096-1102 (2003); Tsupak et al., *Russ. Chem. Bull.* 55:2265-2270 (2006)). To a solution of 3 (2.61 g, 10.1 mmol) in chloroform (13 mL) was added bromine (1.62 g, 0.52 mL, 20.3 mmol in 3 mL chloroform) dropwise over 30 min at room temperature. The reaction mixture was further stirred for 1 min at room temperature before concentrated in vacuo. The crude reaction mixture was purified by flash chromatography to yield 4 (1.96 g, 57%); mp 164-167° C.; MS (ES+) (m/z): [M+1]+ calculated for C$_{14}$H$_{14}$BrN$_2$O$_3$, 338.18. found 337.15, 338.93. This compound matched analytical data as reported (see, e.g., Tsupak et al., *Khimiya Geterotsiklicheskikh Soedinenii.*, supra; Tsupak et al., *Russ. Chem. Bull.*, supra).

N-(2-(1,3-dimethyl-2,4-dioxo-5-phenyl-3,4-dihydro-1H-pyrrolo[3,4-d]pyrimidin-6(2H)-yl)phenyl)acetamide (5). A mixture of N-(2-aminophenyl)acetamide (315 mg, 2.1 mmol), bromo-compound 4 (680 mg, 2 mmol), triethylamine (200 mg, 280 µL, 2 mmol), and ethanol (2 mL) was microwave-heated at 170° C. for 1 h (2-5 mL vial, pressure 13 bar). The shiny white crystalline mass was filtered, washed, and recrystallized from ethanol to give 5 (392 mg, 51% yield): mp>250° C.; $^1$H NMR (DMSO-d$_6$): δ 9.17 (s, 1H), 7.69 (d, 1H, pyrrole CH, J=8.06 Hz), 7.33-7.14 (m, 6H), 7.10-6.94 (m, 3H), 3.31 (s, 3H), 3.17 (s, 3H), 1.87 (s, 3H). MS (ES+) (m/z): [M+1]+ calculated for C$_{22}$H$_{21}$N$_4$O$_3$, 389.43. found 389.19.

6-(2-Aminophenyl)-1,3-dimethyl-5-phenyl-1H-pyrrolo [3,4-d]pyrimidine-2,4(3H,6H)-dione (6). Acetamide compound 5 (200 mg, 0.5 mmol) was refluxed in hydrochloric acid (4 N, 10 mL) for 6 h. The reaction mixture was evaporated under vacuum, and the residue was dissolved in water and neutralized to give 6 (120 mg, 67%) as a white precipitate: mp>300° C.; $^1$H NMR (DMSO-d$_6$): δ 7.32-7.26 (m, 2H), 7.23-7.15 (m, 3H), 7.00 (t, 1H, J=7.32 Hz), 6.87 (s, 1H), 6.80 (d, 1H, J=7.69), 6.70 (d, 1H, J=8.06 Hz), 6.41 (t, 1H, J=7.32 Hz), 5.00 (s, 2H), 3.29 (s, 3H), 3.16 (s, 3H); MS (ES+) (m/z): [M+1]+ calculated for C$_{20}$H$_{19}$N$_4$O$_2$, 347.39. found 347.10.

7,9-Dimethyl-11-phenyl-6-(5-methylfuran-2-yl)-5,6-dihydro-pyrimido[4',5'-3,4]pyrrolo[1,2-a]quinoxaline-8,10-(7H,9H)-dione (PPQ-102, 7). A mixture of 5-methylfuran-2-carbaldehyde (32 mg, 29 µl, 0.29 mmol), compound 6 (101 mg, 0.29 mmol), and ethanol (1 mL) were heated in a microwave reactor at 170° C. for 10 min. A white product was isolated, washed and recrystallized from ethanol to afford 51 mg of 7 (42% yield); m.p.>300° C.; $^1$H NMR (DMSO-d$_6$): δ 7.41 (broad m, 4H), 6.95 (d, 2H, J=8.42 Hz), 6.90-6.83 (m, 2H), 6.29 (d, 2H, J=2.93 Hz), 6.08 (d, 1H, J=2.19 Hz), 5.80 (d, 1H, J=2.93 Hz), 5.69 (d, 1H, J=2.93 Hz), 3.50 (s, 3H), 3.12 (s, 3H), 2.11 (s, 3H). $^{13}$C NMR (DMSO): 159.2, 153.1, 151.9, 151.9, 139.2, 131.5, 129.6, 129.4, 128.8, 126.9, 124.3, 122.8, 120.6, 118.2, 117.6, 111.9, 108.9, 107.1, 105.2, 47.8, 32.3, 28.2, 13.9. HRMS (ES+) (m/z): [M+1]+ calculated for C$_{26}$H$_{23}$N$_4$O$_3$, 439.1765. found, 439.1771.

N-(2-(1,3-dimethyl-2,4-dioxo-5-phenyl-3,4-dihydro-1H-pyrrolo[3,4-d]pyrimidin-6(2H)-yl)phenyl)-5-methylfuran-2-carboxamide (8). To a solution of 7 (12 mg, 27 µmol in 2 mL acetone) was added dropwise a saturated solution of potassium permanganate (13 mg, 80 µmol, 200 µL). The reaction mixture was stirred for 1 h at room temperature and filtered. The residue was processed by standard methods (see, e.g., Oels et al., *J. Chem. Soc. Perkin Trans.* 23:2546-2551 (1977)), and the acetone solution was evaporated to yield 8 (5 mg, 40%). MS (ES+) (m/z): [M+1]+ calculated for C$_{26}$H$_{21}$N$_4$O$_3$, 437.47. found, 437.12.

Example 2

Biological Methods

A. Cell lines and compounds—Fischer rat thyroid (FRT) cells co-expressing human wildtype CFTR and the halide indicator YFP-H148Q/I152L were generated as described (see, e.g., Ma et al., *J. Clin. Invest.* 110:1651-1658 (2002)). Cells were plated in 96-well black-walled microplates (Corning Costar) at a density of 20,000 cells per well in Coon's modified F12 medium supplemented with 5% fetal calf serum, 2 mM L-glutamine, 100 U/mL penicillin, and 100 µg/ml streptomycin. Assays were performed at 48 h after plating the cells when the cells were just confluent. For some experiments, measurements were made using T84 human intestinal epithelial cells and for other experiments, measurements were obtained using primary cultures of human bronchial epithelial cells, which were obtained and grown essentially as previously described (see, e.g., 3 and 27).

The compound collections used for screening to identify CFTR inhibitors included approximately 105,000 synthetic small molecules from ChemDiv (San Diego, Calif.) and Asinex (San Diego, Calif.), and approximately 7500 purified natural compounds from Analyticon (Potsdam, Germany), Timtek (Newark, N.J.), and Biomol (Plymouth Meeting, Pa.). Compounds were maintained as DMSO stock solutions. Structure-activity analysis was performed using analogs purchased from ChemDiv and Asinex.

B. Compound Screening—Assays were performed using an automated screening platform (Beckman) equipped with FLUOStar fluorescence platereaders (BMG Lab Technologies, Offenburg, Germany) as described (see Ma et al., supra). Each well of a 96-well plate containing FRT cells was washed 3 times in PBS (300 µL/wash), leaving 50 µL PBS. Ten µL of a CFTR-activating cocktail (5 µM forskolin, 100 µM IBMX, 25 µM apigenin in PBS) were added, and after 5 min, test compounds (0.5 µL of 1 mM DMSO solution) were added to each well at 25 µM final compound concentration. After 15 min, 96-well plates were transferred to a plate reader for fluorescence assay. Each well was assayed individually for CFTR-mediated iodide influx by recording fluorescence continuously (200 ms per point) for 2 s (baseline) and then for 10 s after rapid addition of 160 µL of isosmolar PBS in which 137 mM chloride was replaced by iodide. The initial rate of iodide influx was computed from fluorescence data by nonlinear regression. Each plate contained negative (DMSO vehicle) and positive (10 µM $CFTR_{inh}$-172) controls.

C. Short-Circuit Current Measurements—Snapwell inserts containing CFTR-expressing FRT cells (stably expressing human wildtype CFTR), T84 cells, or human bronchial epithelial cells were mounted in Ussing chambers. For FRT cells the hemichambers were filled with 5 mL of 75 mM NaCl and 75 mM Na gluconate (apical), and 150 mM NaCl (basolateral) (pH 7.3), and the basolateral membrane was permeabilized with 250 µg/mL amphotericin B. For bronchial epithelial cells and T84 cells, both hemichambers contained a Krebs-bicarbonate solution. Hemichambers were continuously bubbled with air (FRT cells) or 5% $CO_2$ in air (bronchial and T84 cells) and maintained at 37° C. Short-circuit current was recorded continuously using a DVC-1000 voltage clamp (World Precision Instruments, Sarasota, Fla.) using Ag/AgCl electrodes and 3 M KCl agar bridges.

D. Patch-Clamp Analysis—Whole cell recordings were performed using FRT cells stably expressing human wildtype CFTR. The pipette solution contained 140 mM N-methyl D-glucamine chloride (NMDG-Cl), 5 mM EGTA, 1 mM $MgCl_2$, 1 mM Tris-ATP, and 10 mM HEPES (pH 7.2), and the bath solution contained 140 mM N-methyl D-glucamine chloride, 1 mM $CaCl_2$, 1 mM $MgCl_2$, 10 mM glucose and 10 mM HEPES (pH 7.4). Experiments were performed at room temperature (22-25° C.). Pipettes were pulled from borosilicate glass and had resistances of 3-5 Mohm after fire polishing. Seal resistances were typically between 3 and 10 Gohm. After establishing the whole-cell configuration, CFTR was activated by adding forskolin and 3-isobutyl-1-methylxanthine (IBMX). Whole cell currents were elicited by applying hyperpolarizing and depolarizing voltage pulses from a holding potential of 0 mV to potentials between −100 mV and +100 mV in steps of 20 mV. Current was filtered at 5 kHz and digitized and analyzed using an AxoScope 10.0 system and a Digidata® 1440A AC/DC converter (Molecular Devices, Sunnyvale, Calif.). The single channel characteristics of CFTR were analyzed in the cell-attached configuration using fire-polished pipettes with a resistance of 10-15 Mohm. The pipette solution contained (in mM): 140 NMDG-Cl, 1 $CaCl_2$, 1 $MgCl_2$, 5 glucose and 10 HEPES (pH 7.4), and the bath solution contained 140 KCl, 1 $CaCl_2$, 1 $MgCl_2$, 5 glucose and 10 HEPES (pH 7.4). Recordings were performed at room temperature using an Axopatch-200B (Axon Instruments, Foster City, Calif.). The voltage and current data were low-pass filtered at 1 kHz and stored for later analysis. Single channel data were digitally filtered at 25 Hz, and analyzed using Clampfit 10.0 software (Axon Instruments).

E. Embryonic Organ Culture Model of PKD—Mouse embryos were obtained at embryonic day 13.5 (E13.5). Metanephroi were dissected and placed on transparent Falcon 0.4-mm diameter porous cell culture inserts as described (see, e.g., Sonawane et al., Chem. Biol. 15:718-728 (2008)). To the culture inserts was added DMEM/Ham's F-12 nutrient medium supplemented with 2 mM L-glutamine, 10 mM HEPES, 5 µg/mL insulin, 5 µg/mL transferrin, 2.8 nM selenium, 25 ng/ml prostaglandin E, 32 pg/ml T3, 250 U/ml penicillin and 250 µg/ml streptomycin. Kidneys were maintained in a 37° C. humidified $CO_2$ incubator for up to 8 days. Culture medium containing 100 µM 8-Br-cAMP, with or without CFTR inhibitor, was replaced (in the lower chamber) every 12 h. In some studies CFTR inhibitor was added at 3 days after 8-Br-cAMP to test its efficacy in reversing pre-formed cysts. Kidneys were photographed using a Nikon inverted microscope (Nikon TE 2000-S) equipped with 2× objective lens, 520 nm bandpass filter, and high-resolution CCD camera. Percentage cyst area was calculated as total cyst area divided by total kidney area.

Example 3

Identification of PPQ Compounds as CFTR Inhibitors

Collections of synthetic and natural compounds were screened according to the screening procedures described in Example 2. A cell-based fluorescence assay was used in which CFTR inhibitors were identified by reduced iodide influx in FRT cells co-expressing human CFTR and a YFP halide sensor. CFTR was maximally activated by a mixture of agonists having different activating mechanisms. Inhibition of iodide influx was observed as reduced YFP fluorescence quenching in response to rapid iodide addition to each well of 96-well plates. Based on prior knowledge that a small percent of active CFTR inhibitors are identified from random screening of compounds, primary screening was performed at 25 µM test compounds that were pre-incubated for 15 min prior to measuring fluorescence.

Figure 1B:
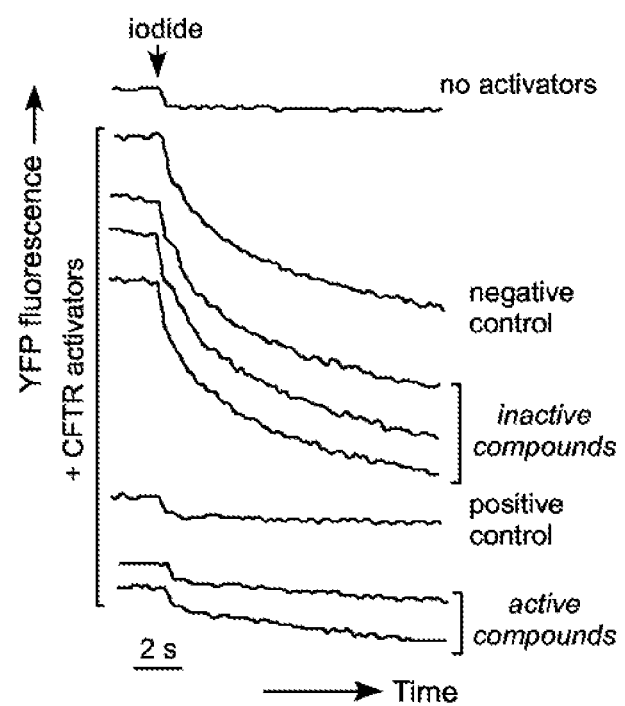

FIG. 1B shows exemplary YFP fluorescence data in negative control (vehicle-only) wells, positive control (10 µM $CFTR_{inh}$-172) wells, and in wells containing test compounds. Representative data for two active compounds are presented. Fifty-four compounds exhibited greater than 50% CFTR inhibition at 25 µM. These fifty-four compounds were included in a second screening assay; electrophysiological measurements indicated that three compounds exhibited greater than 50% CFTR inhibition at 5 µM. Several active compounds that were identified in the screening were related to previously identified CFTR inhibitors. A new class of inhibitors, pyrimido-pyrrolo-quinoxalinedione (PPQ) compounds, was also identified. The structure of the PPQ analog with greatest CFTR inhibition potency (PPQ-102) is shown in FIG. 1A. Unlike previously identified CFTR inhibitors, PPQ compounds are uncharged at physiological pH.

Example 4

Structure-Activity Analysis of PPQ Compounds Identified in Screening Assay

Structure-activity analysis was undertaken to identify the most potent PPQ-class CFTR inhibitors for further characterization and biological testing. Of 347 commercially available PPQ analogs that were screened using the fluorescence screening assay, 54 compounds inhibited CFTR-mediated iodide influx by greater than 50% at 25 µM. Table 1 summarizes CFTR inhibition data for exemplary PPQ compounds that inhibit CFTR. FIG. 2A summarizes CFTR inhibitory activity of PPQ compounds with respect to the effect of various substituents of the PPQ compounds. PPQ analogs having a 5-methyl furanyl moiety (PPQ-101 to PPQ-105) showed greater inhibition potencies than unsubstituted furanyl and thiophene analogs (Group 1, Table 1). Compounds comprising other heterocycles such as 1H-benzimidazole-2-yl and chromenone in place of furan were inactive. Analogs containing phenyls, PPQ-201 to PPQ-203, PPQ-209 and PPQ-210 (Group 2, Table 1) were moderately less potent than the furan analogs PPQ-101 and PPQ-102. In summary, as indicated in Table 1 and FIG. 2A, PPQ compounds exhibiting the greatest CFTR inhibition activity had a 5-methyl furan ring, 3-methylphenyl moiety, and the pyrimido[4',5'-3,4]pyrrolo[1,2-a]quinoxaline template. The furan moiety in many of the active compounds could be replaced with the relatively stable phenyl moiety with minimal loss of activity. All active analogs had a phenyl ring (substituted or unsubstituted) at the 2-position of pyrrole. Methyl substituents on this phenyl ring increased CFTR inhibition potency, as observed for PPQ-101, 102, 103 and PPQ-215, 202, 213. Aromatization of PPQ-102 to PPQ-102b (compound 8, see FIG. 2B), which removes the stereocenter, which results in a planar structure, abolished CFTR inhibition activity.

TABLE 1

CFTR inhibition by PPQ Compounds (IA)

X is O, $R^3$ is methyl, $R^{1c}$ is H (IB)

$R^{4d}$ and $R^{1c}$ are H

TABLE 1-continued

CFTR inhibition by PPQ Compounds

| Group 1 | $R^{2a}=R^{2b}$ | $R^{1a}$ | $R^{1b}$ | % inhibition at 25/5 μM | $IC_{50}^{app}$ (μM) |
|---|---|---|---|---|---|
| PPQ-101 | H | H | $CH_3$ | 98/82 | 0.7 |
| PPQ-102 | H | H | H | 97/87 | 0.8 |
| PPQ-103 | H | $CH_3$ | H | 97/86 | 0.8 |
| PPQ-104 | $CH_3$ | H | H | 90/84 | 0.8 |
| PPQ-105 | $CH_3$ | F | H | 87/80 | 1.5 |

| Group 2 | $R^{4a}$ | $R^{4b}$ | $R^{4c}$ | $R^{2a}=R^{2b}$ | $R^{1a}$ | $R^{1b}$ | | |
|---|---|---|---|---|---|---|---|---|
| PPQ-201 | F | F | H | H | H | H | 93/72 | 1.2 |
| PPQ-202 | H | $NO_2$ | H | H | H | H | 90/60 | 1.2 |
| PPQ-203 | H | H | OH | $CH_3$ | H | H | 99/80 | 1.5 |
| PPQ-204 | H | $OCH_3$ | H | H | H | H | 86/63 | 1.7 |
| PPQ-205 | F | H | H | H | H | H | 81/61 | 2 |
| PPQ-206 | H | H | H | H | H | H | 92/61 | 2.5 |
| PPQ-207 | H | H | OH | H | H | H | 86/64 | 4.5 |
| PPQ-208 | $OCH_3$ | H | OH | H | H | H | 56/5 | 100 |
| PPQ-209 | H | H | OH | H | H | $CH_3$ | 94/71 | 1.7 |
| PPQ-210 | H | $OCH_3$ | H | H | H | $CH_3$ | 98/73 | 1.7 |
| PPQ-211 | H | $OCH_3$ | H | H | F | H | 97/62 | 2 |
| PPQ-212 | F | $NO_2$ | H | H | H | $CH_3$ | 94/61 | 2 |
| PPQ-213 | H | $NO_2$ | H | H | $CH_3$ | H | 96/64 | 2 |
| PPQ-214 | H | Cl | H | H | F | H | 98/70 | 2.5 |
| PPQ-215 | F | H | H | H | H | $CH_3$ | 80/67 | 2.5 |
| PPQ-216 | H | $OCH_3$ | H | H | $CH_3$ | H | 94/62 | 3 |
| PPQ-217 | H | $CH_3$ | H | H | $CH_3$ | H | 100/46 | 3 |
| PPQ-218 | H | H | H | H | $CH_3$ | H | 97/51 | 5 |
| PPQ-219 | H | F | H | H | H | $CH_3$ | 93/53 | 8 |

$IC_{50}^{app}$ is an apparent $IC_{50}$ determined from concentration-inhibition data from the fluorescence platereader assay.

PPQ compounds of structure I, substructures (IA), (IB) were tested and the percent inhibition data from the screening are shown in Table 2 below.

TABLE 2

| PPQ Compound | % Inhibition at 25 μM | % Inhibition at 5 μM | PPQ # |
|---|---|---|---|
| | >95 | >95 | PPQ-101 |

TABLE 2-continued
| PPQ Compound | % Inhibition at 25 μM | % Inhibition at 5 μM | PPQ # |
|---|---|---|---|
| 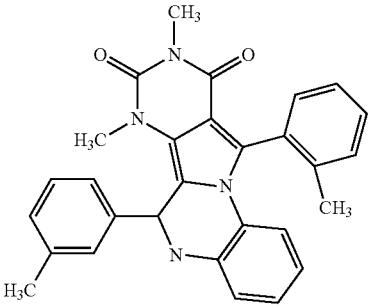 [SMILES: Cc1cccc(C2Nc3ccccc3-n3c(-c4ccccc4C)c4c(=O)n(C)c(=O)n(C)c4c32)c1] | >95 | 46 | PPQ-217 |
| 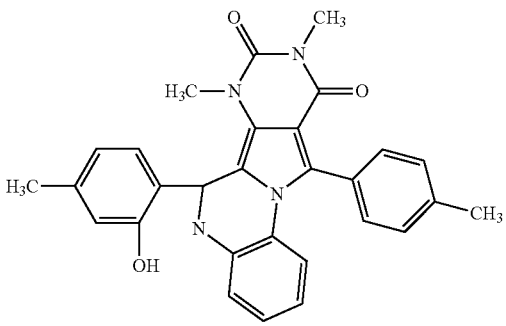 | >95 | <10 | PPQ-220 |
| 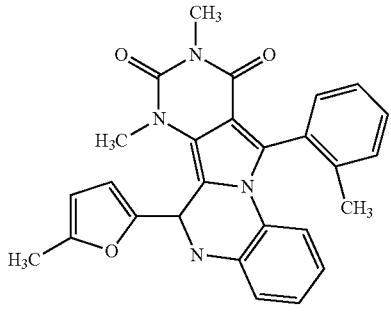 [SMILES: Cc1ccc(C2Nc3ccccc3-n3c(-c4ccccc4C)c4c(=O)n(C)c(=O)n(C)c4c32)o1] | >95 | 63 | PPQ-103 |
| 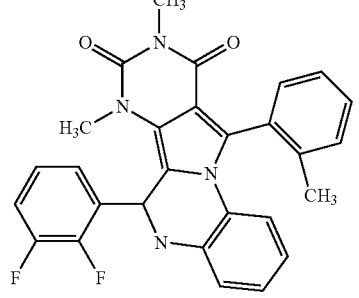 | >95 | 50 | PPQ-221 |

TABLE 2-continued

| PPQ Compound | % Inhibition at 25 μM | % Inhibition at 5 μM | PPQ # |
|---|---|---|---|
| | >95 | 80 | PPQ-203 |
| | >95 | 73 | PPQ-210 |
| | >95 | 70 | PPQ-214 |
| | >95 | 62 | PPQ-216 |

TABLE 2-continued

| PPQ Compound | % Inhibition at 25 μM | % Inhibition at 5 μM | PPQ # |
|---|---|---|---|
| (structure) | 84 | 32 | PPQ-222 |
| (structure) | 92 | 36 | PPQ-223 |
| (structure) | 82 | 24 | PPQ-224 |
| (structure) | 82 | 28 | PPQ-233 |

TABLE 2-continued

| PPQ Compound | % Inhibition at 25 μM | % Inhibition at 5 μM | PPQ # |
|---|---|---|---|
| | 81 | 61 | PPQ-205 |
| | 81 | 53 | PPQ-234 |
| | 80 | 12 | PPQ-235 |
| | 80 | 14 | PPQ-236 |

TABLE 2-continued

| PPQ Compound | % Inhibition at 25 μM | % Inhibition at 5 μM | PPQ # |
|---|---|---|---|
| (structure) | 80 | 67 | PPQ-215 |
| (structure) | 79 | 29 | PPQ-114 |
| (structure) | 61 | 14 | PPQ-115 |
| (structure) | 68 | 12 | PPQ-109 |

TABLE 2-continued

| PPQ Compound | % Inhibition at 25 μM | % Inhibition at 5 μM | PPQ # |
|---|---|---|---|
| | 58 | 20 | PPQ-237 |
| | 58 | 28 | PPQ-301 |
| | 57 | 21 | PPQ-110 |
| | 57 | 22 | PPQ-238 |

TABLE 2-continued

| PPQ Compound | % Inhibition at 25 μM | % Inhibition at 5 μM | PPQ # |
|---|---|---|---|
| (structure) | 56 | 32 | PPQ-244 |
| (structure) | 56 | 13 | PPQ-208 |
| (structure) | 55 | 20 | PPQ-245 |
| (structure) | 54 | 11 | PPQ-112 |

TABLE 2-continued

| PPQ Compound | % Inhibition at 25 μM | % Inhibition at 5 μM | PPQ # |
|---|---|---|---|
| (structure) | 38 | <10 | |
| (structure) | 41 | <10 | |
| (structure) | 38 | <10 | |
| (structure) | 37 | <10 | |

TABLE 2-continued

| PPQ Compound | % Inhibition at 25 μM | % Inhibition at 5 μM | PPQ # |
|---|---|---|---|
| | 36 | <10 | |
| | 35 | <10 | |
| | 58 | 13 | PPQ-247 |
| | 50 | <10 | PPQ-246 |

TABLE 2-continued
| PPQ Compound | % Inhibition at 25 μM | % Inhibition at 5 μM | PPQ # |
|---|---|---|---|
| 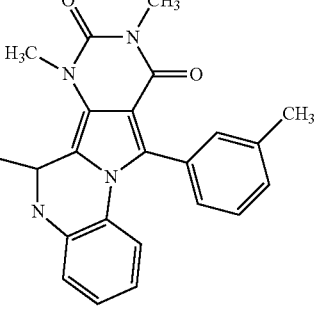 | 72 | 12 | PPQ-243 |
| 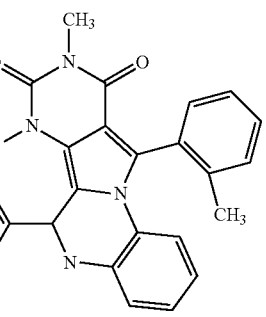 | 74 | 15 | PPQ-242 |
| 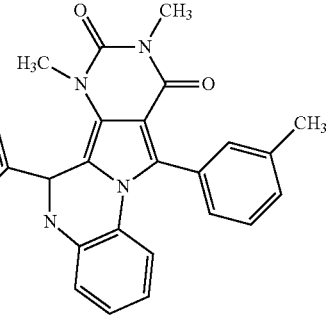 | 74 | 16 | PPQ-241 |
| 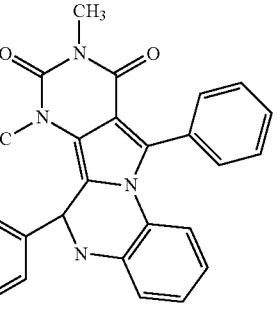 | 74 | 30 | PPQ-240 |
| 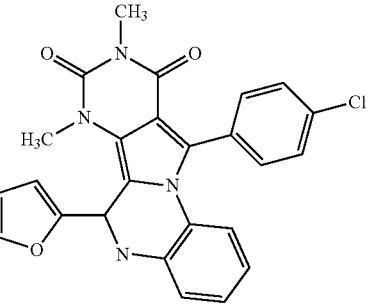 | 75 | 31 | PPQ-111 |

TABLE 2-continued
| PPQ Compound | % Inhibition at 25 μM | % Inhibition at 5 μM | PPQ # |
|---|---|---|---|
| 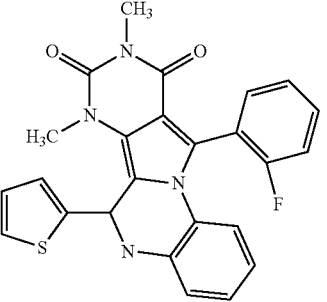 [SMILES: Cn1c(=O)c2c(-c3ccccc3F)n3c(c2n(C)c1=O)C(c1cccs1)Nc1ccccc1-3] | 76 | 47 | PPQ-116 |
| 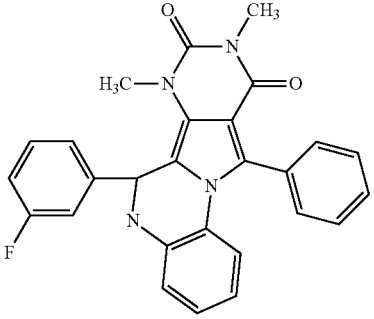 [SMILES: Cn1c(=O)c2c(-c3ccccc3)n3c(c2n(C)c1=O)C(c1cccc(F)c1)Nc1ccccc1-3] | 76 | 45 | PPQ-239 |
| 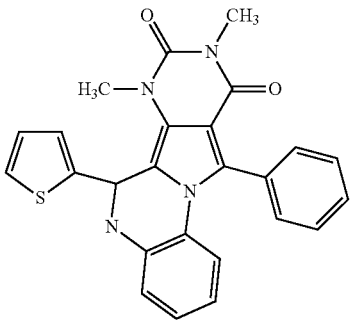 [SMILES: Cn1c(=O)c2c(-c3ccccc3)n3c(c2n(C)c1=O)C(c1cccs1)Nc1ccccc1-3] | 77 | 34 | PPQ-113 |
| 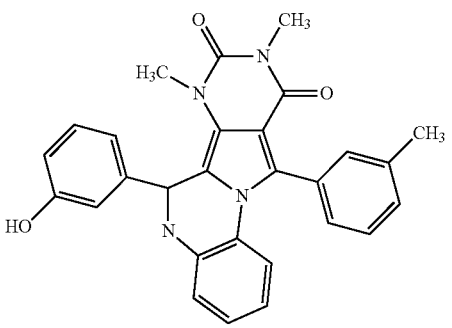 [SMILES: Cc1cccc(-c2c3c(=O)n(C)c(=O)n(C)c3c3n2-c2ccccc2NC3c2cccc(O)c2)c1] | 83 | 30 | PPQ-228 |

TABLE 2-continued

| PPQ Compound | % Inhibition at 25 μM | % Inhibition at 5 μM | PPQ # |
|---|---|---|---|
| | 78 | 10 | PPQ-227 |
| | 92 | 61 | PPQ-226 |
| | 93 | 72 | PPQ-201 |
| | 93 | 53 | PPQ-219 |

TABLE 2-continued
| PPQ Compound | % Inhibition at 25 μM | % Inhibition at 5 μM | PPQ # |
|---|---|---|---|
| 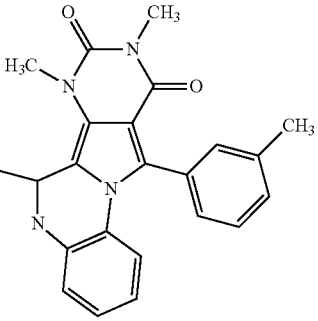 | 94 | 71 | PPQ-209 |
| 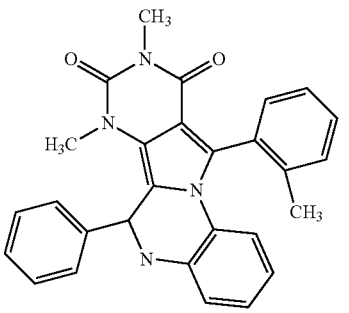 [SMILES: Cc1ccccc1-c1c2c(=O)n(C)c(=O)n(C)c2c2n1-c1ccccc1NC2c1ccccc1] | 94 | 41 | PPQ-218 |
| 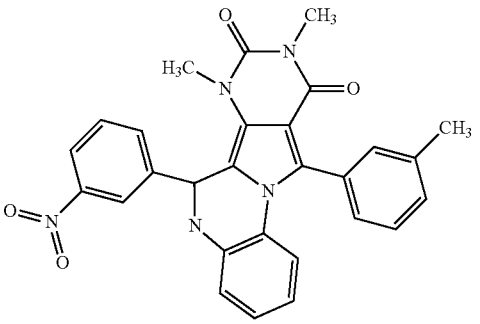 [SMILES: Cc1cccc(-c2c3c(=O)n(C)c(=O)n(C)c3c3n2-c2ccccc2NC3c2cccc([N+](=O)[O-])c2)c1] | 94 | 61 | PPQ-225 |
| 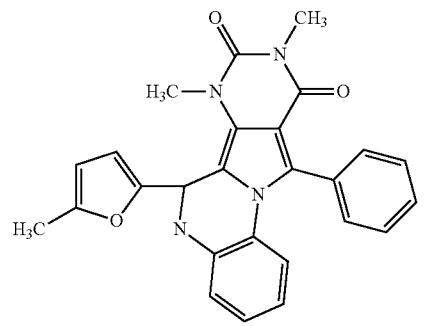 [SMILES: Cc1ccc(C2Nc3ccccc3-n3c(-c4ccccc4)c4c(=O)n(C)c(=O)n(C)c4c32)o1] | 97 | 85 | PPQ-102 |

TABLE 2-continued

| PPQ Compound | % Inhibition at 25 μM | % Inhibition at 5 μM | PPQ # |
|---|---|---|---|
| [structure] | 96 | 49 | PPQ-106 |
| [structure] | 96 | 64 | PPQ-213 |
| [structure] | 47 | <10 | |
| [structure] | 47 | 13 | |

TABLE 2-continued
| PPQ Compound | % Inhibition at 25 μM | % Inhibition at 5 μM | PPQ # |
|---|---|---|---|
| 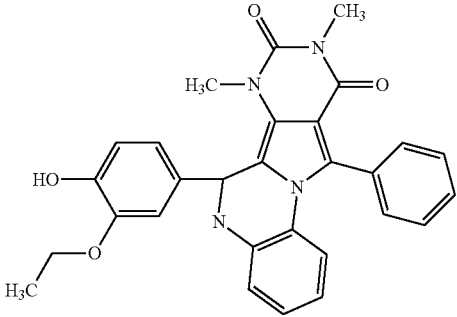 [SMILES: CCOc1cc(C2Nc3ccccc3-n3c(-c4ccccc4)c4c(=O)n(C)c(=O)n(C)c4c32)ccc1O] | 47 | <10 | |
| 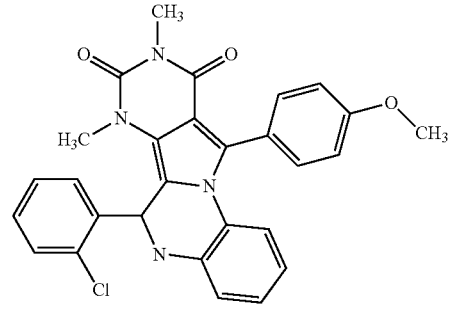 [SMILES: COc1ccc(-c2c3c(=O)n(C)c(=O)n(C)c3c3n2-c2ccccc2NC3c2ccccc2Cl)cc1] | 47 | <10 | |
| 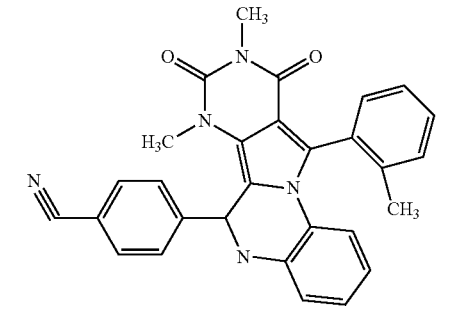 [SMILES: Cc1ccccc1-c1c2c(=O)n(C)c(=O)n(C)c2c2n1-c1ccccc1NC2c1ccc(C#N)cc1] | 45 | <10 | |
| 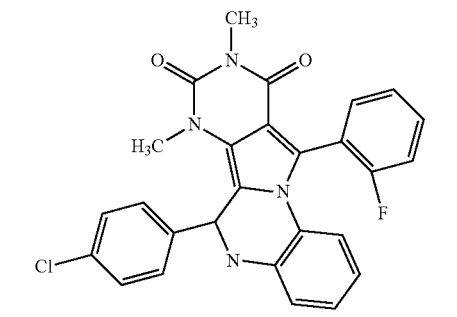 [SMILES: Cn1c(=O)c2c(-c3ccccc3F)n3c(c2n(C)c1=O)C(c1ccc(Cl)cc1)Nc1ccccc1-3] | 44 | <10 | |

TABLE 2-continued

| PPQ Compound | % Inhibition at 25 μM | % Inhibition at 5 μM | PPQ # |
|---|---|---|---|
| | 44 | 41 | |
| | 41 | 13 | |
| | 35 | 23 | |
| | 38 | 13 | |

TABLE 2-continued

| PPQ Compound | % Inhibition at 25 μM | % Inhibition at 5 μM | PPQ # |
|---|---|---|---|
| | 34 | <10 | |
| | 33 | <10 | |
| | 33 | <10 | |
| | 31 | <10 | |
| | >95 | 62 | PPQ-211 |

TABLE 2-continued

| PPQ Compound | % Inhibition at 25 μM | % Inhibition at 5 μM | PPQ # |
|---|---|---|---|
| | 90 | 57 | PPQ-229 |
| | 90 | 60 | PPQ-202 |
| | 90 | 84 | PPQ-104 |
| | 87 | 51 | PPQ-230 |

TABLE 2-continued

| PPQ Compound | % Inhibition at 25 μM | % Inhibition at 5 μM | PPQ # |
|---|---|---|---|
| | 87 | 24 | PPQ-107 |
| | 87 | <10 | PPQ-231 |
| | 86 | 63 | PPQ-204 |
| | 86 | 64 | PPQ-207 |

TABLE 2-continued

| PPQ Compound | % Inhibition at 25 μM | % Inhibition at 5 μM | PPQ # |
|---|---|---|---|
| | 70 | 18 | PPQ-108 |
| | 78 | 78 | PPQ-105 |
| | 67 | 67 | PPQ-232 |
| | 67 | 19 | PPQ-117 |

TABLE 2-continued

| PPQ Compound | % Inhibition at 25 μM | % Inhibition at 5 μM | PPQ # |
|---|---|---|---|
| | 64 | 5 | PPQ-248 |
| | 64 | 21 | PPQ-249 |
| | 64 | 49 | PPQ-250 |
| | 78 | <10 | PPQ-252 |

TABLE 2-continued

| PPQ Compound | % Inhibition at 25 μM | % Inhibition at 5 μM | PPQ # |
|---|---|---|---|
| | 63 | 26 | PPQ-302 |
| | 62 | 13 | PPQ-251 |
| | 31 | 27 | |
| | 33 | <10 | |
| | 32 | <10 | |

TABLE 2-continued

| PPQ Compound | % Inhibition at 25 μM | % Inhibition at 5 μM | PPQ # |
|---|---|---|---|
| (structure) | 41 | <10 | |
| (structure) | 35 | <10 | |
| (structure) | 40 | 12 | |
| (structure) | 39 | <10 | |

TABLE 2-continued
| PPQ Compound | % Inhibition at 25 μM | % Inhibition at 5 μM | PPQ # |
|---|---|---|---|
| 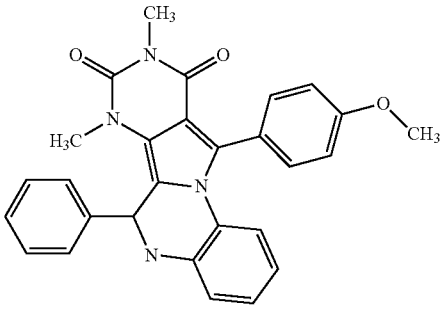 [SMILES: COc1ccc(-c2c3c(=O)n(C)c(=O)n(C)c3c3n2-c2ccccc2NC3c2ccccc2)cc1] | 39 | <10 | |
| 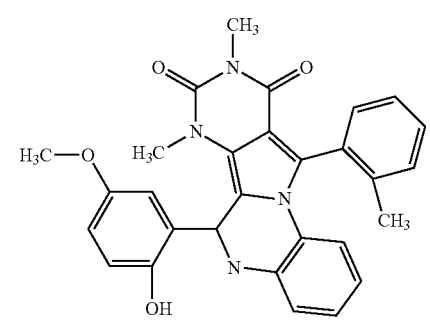 [SMILES: COc1ccc(O)c(C2Nc3ccccc3-n3c(-c4ccccc4C)c4c(=O)n(C)c(=O)n(C)c4c32)c1] | 38 | <10 | |
| 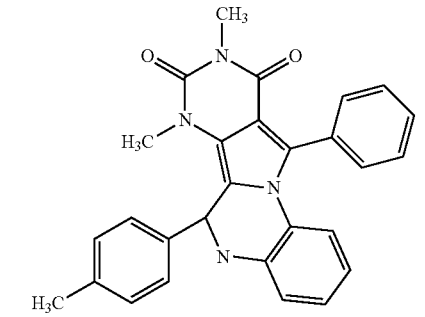 [SMILES: Cc1ccc(C2Nc3ccccc3-n3c(-c4ccccc4)c4c(=O)n(C)c(=O)n(C)c4c32)cc1] | 38 | <10 | |
| 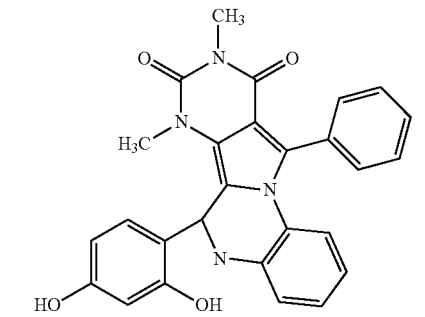 [SMILES: Cn1c(=O)c2c(-c3ccccc3)n3c(c2n(C)c1=O)C(c1ccc(O)cc1O)Nc1ccccc1-3] | 35 | <10 | |
| 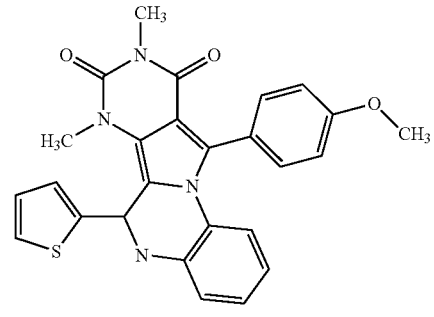 [SMILES: COc1ccc(-c2c3c(=O)n(C)c(=O)n(C)c3c3n2-c2ccccc2NC3c2cccs2)cc1] | 34 | <10 | |

TABLE 2-continued

| PPQ Compound | % Inhibition at 25 μM | % Inhibition at 5 μM | PPQ # |
|---|---|---|---|
| (structure) | 31 | <10 | |
| (structure) | 30 | <10 | |
| (structure) | 31 | <10 | |

Example 5

Inhibition of CFTR-Mediated Chloride Current by PPQ Compounds

This Example describes potency, reversibility, and specificity of an exemplary PPQ compound, PPQ-102 as determined by CFTR chloride conductance.

Figure 3A:
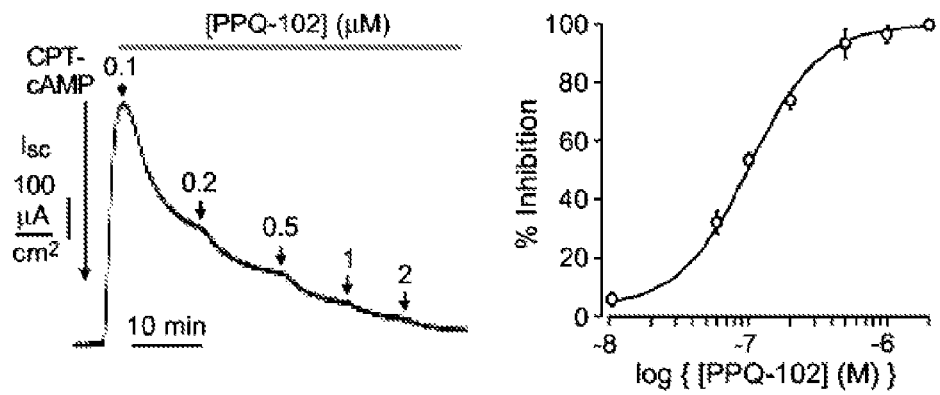
FIGS. 3A-E present data demonstrating CFTR inhibition by PPQ-102.

The most potent CFTR inhibitor confirmed by electrophysiological testing, PPQ-102, was synthesized as described in Example 1, confirmed, and further characterized. Short circuit current analysis was performed as described in Example 2. FIG. 3A (left) shows PPQ-102 inhibition of chloride current in CFTR-expressing FRT cells following CFTR stimulation by the cAMP agonist CPT-cAMP. Measurements were taken in the presence of a transepithelial chloride gradient and following basolateral membrane permeabilization with amphotericin B so that measured current is a direct, quantitative measure of CFTR chloride conductance. PPQ inhibition of CFTR was approximately 100% at higher concentrations, with $IC_{50}$~90 nM (see FIG. 3A, right). Inhibition occurred over several minutes at low PPQ-102 concentrations, suggesting an intracellular site of action. Inhibition was reversible, which was observed by complete restoration of CFTR chloride current after 30 min incubation with 2 μM PPQ-102, followed by 10 min washout.

Figure 3B:
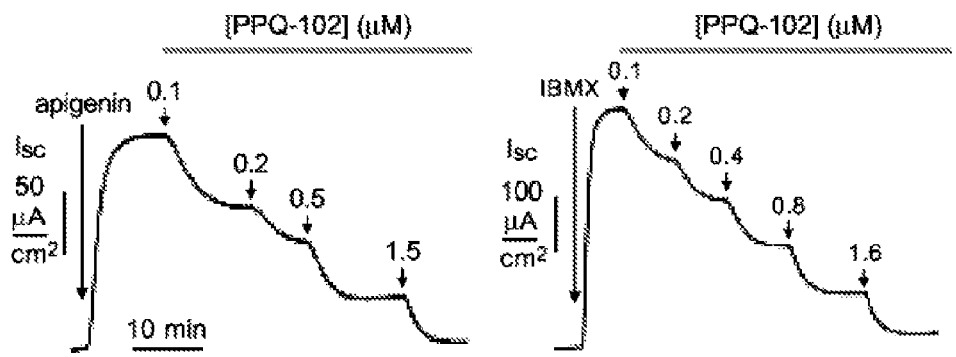
Figure 3C:
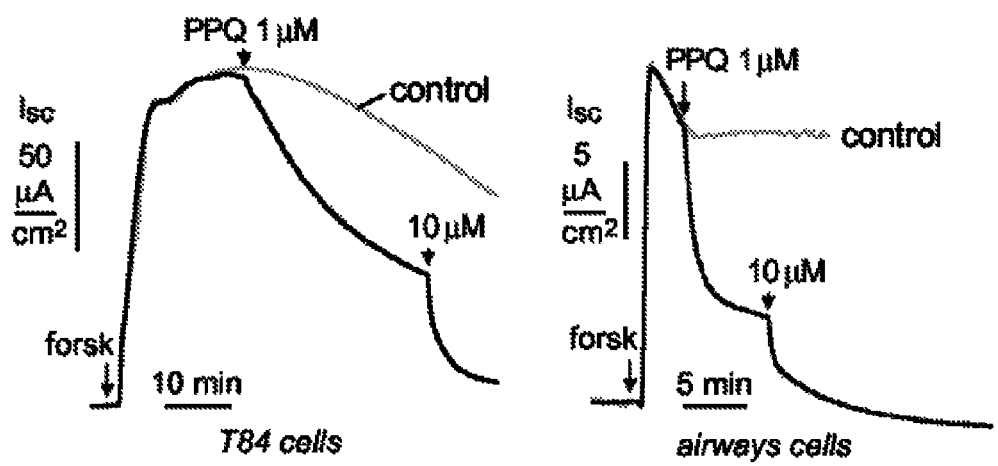

FIG. 3B shows PPQ-102 inhibition of CFTR chloride current following CFTR activation by apigenin, a flavone-type CFTR agonist that acts by directly binding to CFTR, and IBMX, a phosphodiesterase inhibitor that also binds directly to CFTR. The mildly reduced PPQ-102 potency in response to these agonists, compared to a pure cAMP agonist (CPT-cAMP) that activates CFTR by a physiological phosphorylation mechanism, is consistent with PPQ-102 action at nucleotide binding domain(s) on the intracellular CFTR surface. As shown in FIG. 3C, PPQ-102 inhibited short-circuit current in (non-permeabilized) human intestinal (T84) and bronchial cells following maximal CFTR activation by forskolin and IBMX. CFTR inhibition was near 100% at 10 μM PPQ-102 with an $IC_{50}$ significantly below 1 μM. In the non-permeabilized T84 and bronchial epithelial cells, which have a strong interior-negative membrane potential, the $IC_{50}$ for CFTR inhibition by PPQ of <<1 μM was substantially better than that of 3-5 μM previously observed for $CFTR_{inh}$-172 and GlyH-101 (see, e.g., Ma et al., supra; Muanprasat et al., *J. Gen. Physiol.* 124:125-137 (2004)).

Figure 3D:
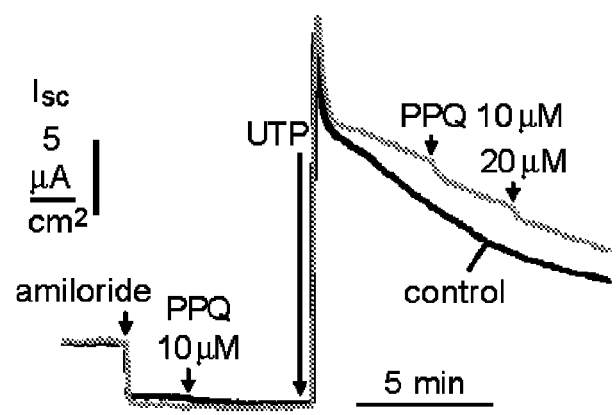
Figure 3E:
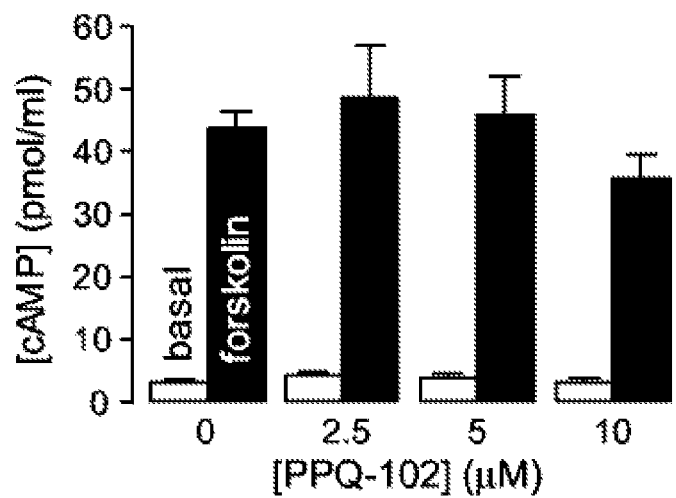

PPQ-102 did not inhibit calcium-activated chloride channels or cellular cAMP production. FIG. 3D shows little inhibition of UTP-induced chloride currents in cystic fibrosis human bronchial cells by 10 or 20 μM PPQ-102. FIG. 3E shows no significant effect of 10 μM PPQ-102 on basal or forskolin-stimulated cAMP production.

Figure 4A:
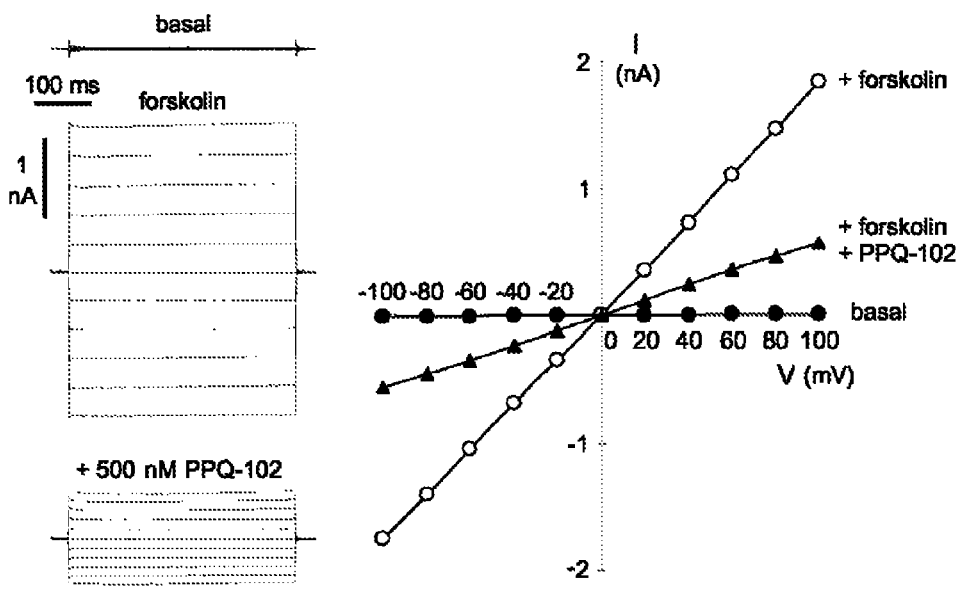
FIGS. 4A and 4B present patch-clamp analysis of PPQ-102 inhibition of CFTR.

Whole-cell membrane current was measured by patch-clamp in CFTR-expressing FRT cells (see Example 2). The results are presented in FIG. 4. Stimulation by 10 μM forskolin produced a membrane current of 172±39 pA/pF (n=4) at +100 mV (total membrane capacitance 13±1 pF) (see FIG. 4A, left). PPQ-102 at 0.5 μM exhibited approximately 65% inhibition of CFTR chloride current. As shown in FIG. 4A (right), an approximately linear current-voltage relationship for CFTR is observed (see also, e.g., Sheppard et al., *Physiol. Rev.* 79:S23-452 (1999); Gadsby et al., *Nature* 40:477-483 (2006)). The CFTR current-voltage relationship remained linear after PPQ-102 addition, indicting a voltage-independent block mechanism, as expected for an uncharged inhibitor.

Figure 4B:
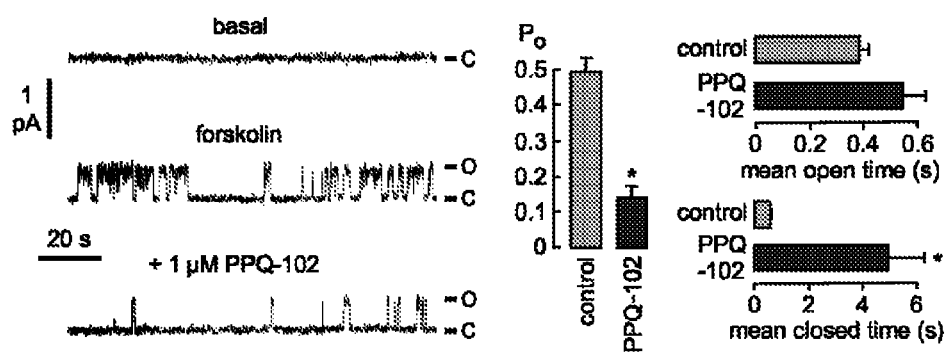

Cell-attached patch recordings were performed to examine single-channel CFTR function. The results are presented in FIG. 4B. Addition of 10 μM forskolin and 100 μM IBMX to the bath resulted in CFTR channel opening. CFTR unitary conductance was 7 pS at +80 mV. Application of 1 μM PPQ-102 did not change unitary conductance, but reduced channel activity markedly as seen by the less frequent channel openings as illustrated in FIG. 4B (left). Channel open probability ($P_o$) was reduced from 0.50±0.04 to 0.14±0.03. Mean channel open time did not significantly change, but mean channel closed time was greatly increased (see FIG. 4B, right). Without wishing to be bound by theory, these results suggest that PPQ-102 inhibits CFTR by an altered channel gating mechanism, with stabilization of the channel closed state.

Example 6

Effectiveness of a PPQ Compound in a Polycystic Kidney Disease Model

This Example describes analysis of the PPQ compound, PPQ-102, in an embryonic kidney culture model of polycystic kidney disease.

Figure 5A:
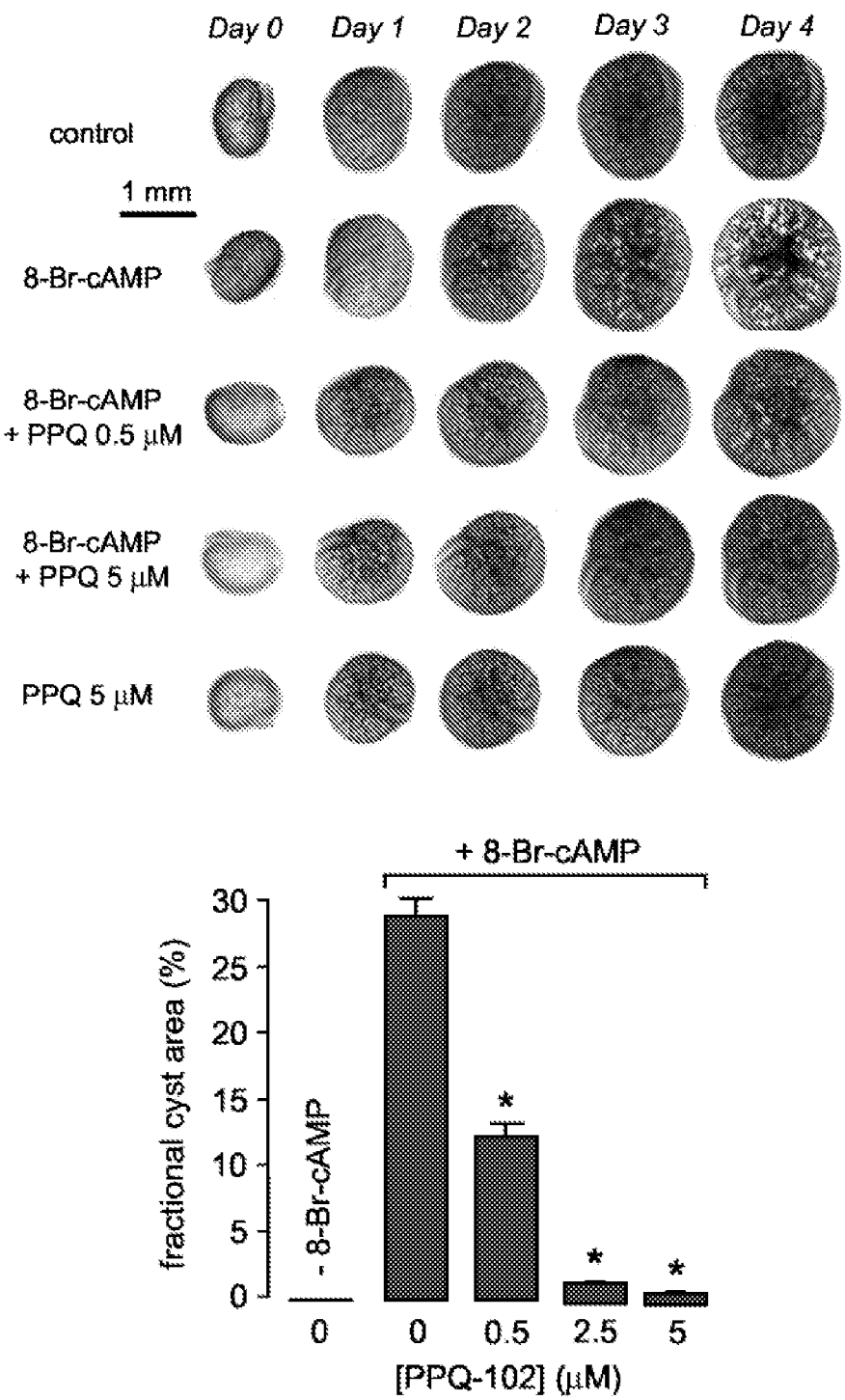
FIGS. 5A-C illustrates that PPQ-102 prevented and reversed renal cyst expansion in an embryonic kidney organ culture model of PKD. E13.5 embryonic kidneys were maintained in organ culture in defined medium.
Figure 5B:
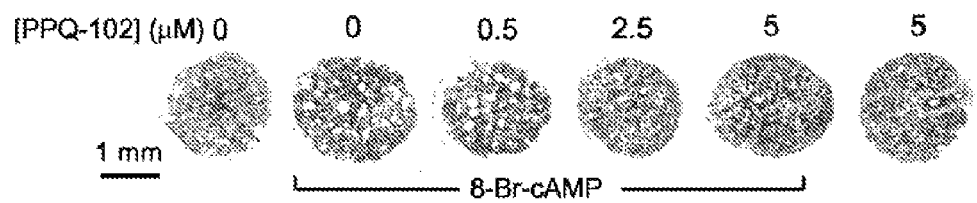

Kidneys were removed from day 13.5 embryonic mice and maintained in organ culture where they continue to grow. Examination of kidneys by transmission light microscopy showed that the kidneys in organ culture did not form cysts under control conditions. Multiple cysts did form and progressively enlarged when the culture medium was supplemented with the CFTR agonist 8-Br-cAMP (see FIG. 5A, left). Inclusion of PPQ-102 in the culture medium did not affect kidney growth, but significantly reduced the number and size of renal cysts formed in the 8-Br-cAMP-containing medium. FIG. 5A (right) summarizes the percentage area occupied by cysts from studies performed on many kidneys, showing approximately 60% inhibition of cyst formation by 0.5 μM PPQ-102 and near complete absence of cysts at 2.5 and 5 μM PPQ-102. In control studies in which 2.5 μM PPQ-102 was removed after 3 days in organ culture, cysts rapidly enlarged in the continued presence of 8-Br-cAMP, indicating that the inhibition effect of PPQ-102 is reversible. FIG. 5B shows representative hematoxylin and eosin-stained paraffin sections of control and 8-Br-cAMP-treated kidneys cultured for 4 day in the presence of indicated concentrations of PPQ-102. In agreement with the transmission light micrographs of intact kidneys, PPQ-102 reduced cyst size.

Figure 5C:
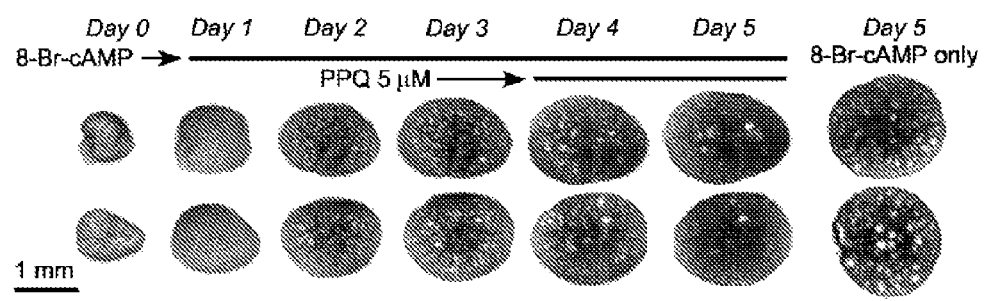
Figure 5C:
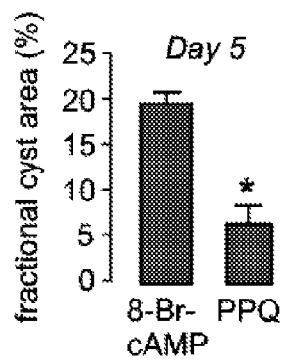

The ability of PPQ-102 to reduce fluid accumulation in pre-formed cysts was tested by adding PPQ-102 to the 8-Br-cAMP-containing medium after kidneys were cultured for 3 days in the presence of 8-Br-cAMP. FIG. 5C shows reduction in cyst size over 1 and 2 days after inclusion of PPQ-102 in the culture medium. Without wishing to be bound by theory, shrinking of pre-formed cysts by PPQ-102 supports that renal cystogenesis involves a balance between active fluid secretion into and absorption from the cyst lumen.

All U.S. patents, U.S. patent application publications, U.S. patent applications, foreign patents, foreign patent applications, and non-patent publications referred to in this specification and/or listed in the Application Data Sheet, are incorporated herein by reference, in their entirety.

From the foregoing, although specific embodiments have been described herein for purposes of illustration, various modifications may be made without deviating from the spirit and scope of the invention. Those skilled in the art will recognize, or be able to ascertain, using no more than routine experimentation, many equivalents to the specific embodiments described herein. Such equivalents are intended to be encompassed by the following claims.

We claim the following:

1. A pharmaceutical composition comprising a physiological acceptable excipient and a compound having the following structure (IA):

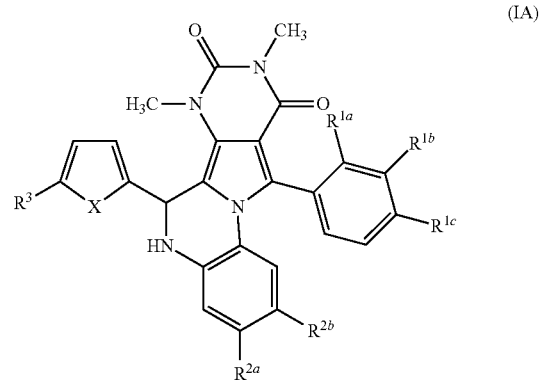

(IA)

as an isolated enantiomer or a racemic mixture of enantiomers, or as a pharmaceutically acceptable salt, hydrate, solvate, or N-oxide thereof, wherein:

$R^{1a}$, $R^{1b}$, and $R^{1c}$ are each the same or different and independently hydrogen, alkyl, halo, or alkoxy;

$R^{2a}$ and $R^{2b}$ are each the same or different and independently hydrogen, alkyl, halo, or alkoxy;

$R^3$ is hydrogen or alkyl, and

X is —O—, or —S—, wherein the compound is capable of inhibiting cystic fibrosis transmembrane conductance regulator (CFTR)-mediated ion transport.

2. The pharmaceutical composition of claim 1, wherein:

X is —O—, $R^{1a}$, $R^{1b}$, and $R^{1c}$ are each the same or different and independently hydrogen, alkyl, halo, or alkoxy;

$R^{2a}$ and $R^{2b}$ are each the same or different and independently hydrogen or alkyl; and $R^3$ is hydrogen or alkyl.

3. The pharmaceutical composition of claim 2, wherein:

$R^{1a}$, $R^{1b}$, and $R^{1c}$ are each the same or different and independently hydrogen, $C_{1-6}$ alkyl, halo, or $C_{1-6}$ alkoxy;

$R^{2a}$ and $R^{2b}$ are each the same or different and independently hydrogen or $C_{1-6}$ alkyl; and $R^3$ is hydrogen or $C_{1-6}$ alkyl.

4. The pharmaceutical composition of claim 3, wherein:
$R^{1a}$, $R^{1b}$, and $R^{1c}$ are each the same or different and independently hydrogen, methyl, chloro, fluoro, or methoxy;
$R^{2a}$ and $R^{2b}$ are each the same or different and independently hydrogen or methyl; and
$R^3$ is hydrogen or methyl.

5. The pharmaceutical composition of claim 4, wherein the compound of structure (IA) is selected from the following:
7,9-Dimethyl-11-(3-methylphenyl)-6-(5-methylfuran-2-yl)-5,6-dihydro-pyrimido[4',5'-3,4]pyrrolo[1,2-a]quinoxaline-8,10-(7H,9H)-dione;
7,9-Dimethyl-11-phenyl-6-(5-methylfuran-2-yl)-5,6-dihydro-pyrimido[4',5'-3,4]pyrrolo[1,2-a]quinoxaline-8,10-(7H,9H)-dione;
7,9-Dimethyl-11-(2-methylphenyl)-6-(5-methylfuran-2-yl)-5,6-dihydro-pyrimido[4',5'-3,4]pyrrolo[1,2-a]quinoxaline-8,10-(7H,9H)-dione;
2,3,7,9-Tetramethyl-11-phenyl-6-(5-methylfuran-2-yl)-5,6-dihydro-pyrimido[4',5'-3,4]pyrrolo[1,2-a]quinoxaline-8,10-(7H,9H)-dione;
2,3,7,9-Tetramethyl-11-(2-fluorophenyl)-6-(5-methylfuran-2-yl)-5,6-dihydro-pyrimido[4',5'-3,4]pyrrolo[1,2-a]quinoxaline-8,10-(7H,9H)-dione;
7,9-Dimethyl-11-(3-methylphenyl)-6-(furan-2-yl)-5,6-dihydro-pyrimido[4',5'-3,4]pyrrolo[1,2-a]quinoxaline-8,10-(7H,9H)-dione;
2,3,7,9-Tetramethyl-11-phenyl-6-(furan-2-yl)-5,6-dihydro-pyrimido[4',5'-3,4]pyrrolo[1,2-a]quinoxaline-8,10-(7H,9H)-dione;
7,9-Dimethyl-11-(2-methylphenyl)-6-(furan-2-yl)-5,6-dihydro-pyrimido[4',5'-3,4]pyrrolo[1,2-a]quinoxaline-8,10-(7H,9H)-dione;
7,9-Dimethyl-11-(4-methoxyphenyl)-6-(5-methylfuran-2-yl)-5,6-dihydro-pyrimido[4',5'-3,4]pyrrolo[1,2-a]quinoxaline-8,10-(7H,9H)-dione;
7,9-Dimethyl-11-(4-methylphenyl)-6-(5-methylfuran-2-yl)-5,6-dihydro-pyrimido[4',5'-3,4]pyrrolo[1,2-a]quinoxaline-8,10-(7H,9H)-dione;
7,9,-Dimethyl-11-(4-chlorophenyl)-6-(5-methylfuran-2-yl)-5,6,-dihydropyrimido[4',5'-3,4]pyrrole[1,2-a]quinoxaline-8,10-(7H,9H)-dione; and
7,9-Dimethyl-11-phenyl-6-(5-furan-2-yl)-5,6-dihydro-pyrimido[4',5'-3,4]pyrrolo[1,2-a]quinoxaline-8,10-(7H,9H)-dione.

6. The pharmaceutical composition of claim 1, wherein:
X is —S—,
$R^{1a}$, $R^{1b}$, and $R^{1c}$ are each the same or different and independently hydrogen, alkyl, halo, or alkoxy;
$R^{2a}$ and $R^{2b}$ are each the same or different and independently hydrogen or alkyl; and
$R^3$ is hydrogen or alkyl.

7. The pharmaceutical composition of claim 6, wherein:
$R^{1a}$, $R^{1b}$, and $R^{1c}$ are each the same or different and independently hydrogen, $C_{1-6}$ alkyl, halo, or $C_{1-6}$ alkoxy;
$R^{2a}$ and $R^{2b}$ are each the same or different and independently hydrogen or $C_{1-6}$ alkyl; and
$R^3$ is hydrogen or $C_{1-6}$ alkyl.

8. The pharmaceutical composition of claim 7, wherein:
$R^{1a}$, $R^{1b}$, and $R^{1c}$ are each the same or different and independently hydrogen, methyl, chloro, fluoro, or methoxy;
$R^{2a}$ and $R^{2b}$ are each the same or different and independently hydrogen or methyl; and
$R^3$ is hydrogen or methyl.

9. The pharmaceutical composition of claim 8, wherein the compound of structure (IA) is selected from the following:
7,9-Dimethyl-11-phenyl-6-(thienyl-2-yl)-5,6-dihydro-pyrimido[4',5'-3,4]pyrrolo[1,2-a]quinoxaline-8,10-(7H,9H)-dione;
7,9-Dimethyl-11-(3-methylphenyl)-6-(thienyl-2-yl)-5,6-dihydro-pyrimido[4',5'-3,4]pyrrolo[1,2-a]quinoxaline-8,10-(7H,9H)-dione;
2,3,7,9-Tetramethyl-11-phenyl-6-(thienyl-2-yl)-5,6-dihydro-pyrimido[4',5'-3,4]pyrrolo[1,2-a]quinoxaline-8,10-(7H,9H)-dione;
7,9-Dimethyl-11-(2-fluorophenyl)-6-(thienyl-2-yl)-5,6-dihydro-pyrimido[4',5'-3,4]pyrrolo[1,2-a]quinoxaline-8,10-(7H,9H)-dione; and
7,9-Dimethyl-11-(2-methylphenyl)-6-(thienyl-2-yl)-5,6-dihydro-pyrimido[4',5'-3,4]pyrrolo[1,2-a]quinoxaline-8,10-(7H,9H)-dione.

10. A method for inhibiting cystic fibrosis transmembrane conductance regulator (CFTR)-mediated ion transport, said method comprising contacting (a) a cell that comprises CFTR and (b) the pharmaceutical composition of claim 1, under conditions and for a time sufficient that permit the CFTR and the compound to interact, thereby inhibiting CFTR-mediated ion transport.

11. A method for inhibiting cyst formation or inhibiting cyst enlargement in a subject who has polycystic kidney disease, said method comprising contacting (a) a cell that comprises CFTR in the subject and (b) the pharmaceutical composition of claim 1 administered to the subject, under condition and for a time sufficient that permit CFTR and the compound to interact, wherein the compound inhibits CFTR-mediated ion transport.

12. A method for treating polycystic kidney disease comprising administering to a subject who has polycystic kidney disease the composition of claim 1.

13. The method of claim 12 wherein polycystic kidney disease is autosomal dominant polycystic kidney disease or autosomal recessive polycystic kidney disease.

14. A method for treating a disease, condition, or disorder that is treatable by inhibiting cystic fibrosis transmembrane conductance regulator (CFTR)-mediated ion transport, wherein the disease, condition, or disorder is secretory diarrhea, said method comprising administering to a subject who has the disease, condition, or disorder the pharmaceutical composition of claim 1, thereby inhibiting CFTR-mediated ion transport.

15. The method of claim 14, wherein secretory diarrhea is (a) caused by an enteric pathogen; (b) induced by an enterotoxin; or (c) a sequelae of ulcerative colitis, irritable bowel syndrome (IBS), AIDS, chemotherapy, or an enteropathogenic infection.

* * * * *

UNITED STATES PATENT AND TRADEMARK OFFICE
CERTIFICATE OF CORRECTION

PATENT NO. : 8,609,661 B2  
APPLICATION NO. : 13/389898  
DATED : December 17, 2013  
INVENTOR(S) : Alan S. Verkman et al.

Page 1 of 1

It is certified that error appears in the above-identified patent and that said Letters Patent is hereby corrected as shown below:

In the Claims

Column 121, Lines 42-44, Claim 5:
"7,9-Dimethyl-11-(4-chlorophenyl)-6-(5-methylfuran-2-yl)-5,6,-dihydropyrimido[4',5'-3,4]pyrrole[1,2-a]quinoxaline-8,10-(7H,9H)-dione; and" should read, --7,9-Dimethyl-11-(4-chlorophenyl)-6-(5-methylfuran-2-yl)-5,6-dihydro-pyrimido[4',5'-3,4]pyrrolo[1,2-a]quinoxaline-8,10-(7H,9H)-dione; and--.

Column 122, Line 36, Claim 11:
"condition and for a time sufficient that permit CFTR and the" should read, --conditions and for a time sufficient that permit CFTR and the--.

Signed and Sealed this  
Seventh Day of October, 2014

Michelle K. Lee  
*Deputy Director of the United States Patent and Trademark Office*